(12) United States Patent
Khan et al.

(10) Patent No.: US 6,844,315 B2
(45) Date of Patent: *Jan. 18, 2005

(54) IMMUNOREGULATOR

(75) Inventors: Nisar Ahmed Khan, Rotterdam (NL); Robbert Benner, Barendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/821,380

(22) Filed: Mar. 29, 2001

(65) Prior Publication Data

US 2002/0064501 A1 May 30, 2002

Related U.S. Application Data

(63) Continuation-in-part of application No. 09/716,777, filed on Nov. 20, 2000, which is a continuation of application No. PCT/NL99/00313, filed on May 20, 1999.

(51) Int. Cl.[7] .............................................. A61K 38/24
(52) U.S. Cl. ............................................ 514/2; 514/21
(58) Field of Search ....................... 514/2, 21

(56) References Cited

U.S. PATENT DOCUMENTS

| 5,958,413 A | * | 9/1999 | Anagnostopulos et al. | .................. 424/178.1 |
|---|---|---|---|---|
| 6,319,504 B1 | | 11/2001 | Gallo et al. | |

FOREIGN PATENT DOCUMENTS

| FR | 2706772 | * 12/1994 |
|---|---|---|
| WO | WO 97/49721 | 12/1997 |
| WO | WO 99/59617 | 11/1999 |
| WO | WO 01/10907 A2 | 2/2001 |
| WO | WO 01/11048 A2 | 2/2001 |
| WO | WO 01/72831 | 10/2001 |

OTHER PUBLICATIONS

Connelly et al., Biphasic Regulation of NF–kB Activity Underlies the Pro– and Anti–inflammatory Actions of Nitric Oxide, The Journal of Immunology, 2001, pp. 3873–3881, 166, The American Association of Immunologists, USA.
Friedlander, Tackling anthrax, Nature, Nov. 8, 2001, pp. 160–161, vol. 414.
Medzhitov, Toll–like Receptors and Innate Immunity, Nature Reviews/Immunology, Nov. 2001, pp. 135–145, vol. 1.
PCT International Preliminary Examination Report, PCT/Nl99/00313. dated Jul. 21, 2000, 6 pages.
PCT International Search Report, PCT/NL99/00313, dated Nov. 29, 1999, 3 pages.
PCT International Search Report, PCT/NL01/00259, dated Dec. 18, 2001, 3 pages.
PCT International Preliminary Examination Report, PCT/NL99/00313. dated Jul. 21, 2000, 6 pages.
PCT International Search Report, PCT/EP99/00313, dated Nov. 29, 1999, 3 pages.
Lang et al., "Induction of apoptosis in Kaposi's sarcoma spindle cell cultures by the subunits of human chorionic gonadotropin", *AIDS* 1997, vol. 11, No. 11, pp. 1333–1340.
Iskandar et al., "Effects of a urinary factor from women in early pregnancy on HIV–1. SIV and associated disease ", *Nature Medicine*, Apr. 1998, vol. 4, No. 4, pp. 428–434.

* cited by examiner

*Primary Examiner*—Jean C. Witz
(74) *Attorney, Agent, or Firm*—TraskBritt

(57) ABSTRACT

The invention relates to the field of immunology. Specifically, the invention relates to the field of immune-mediated disorders such as allergies, auto-immune disease, transplantation-related disease or inflammatory disease. The invention provides for an immunoregulator (IR), use of an IR in preparing a pharmaceutical composition for treating an immune-mediated disorder and a method for treating an immune-mediated disorder.

9 Claims, No Drawings

SEQUENCE LISTING

```
<160> NUMBER OF SEQ ID NOS: 12

<210> SEQ ID NO 1
<211> LENGTH: 17
<212> TYPE: PRT
<213> ORGANISM: Unknown
<220> FEATURE:
<223> OTHER INFORMATION: Peptide immunoregulator

<400> SEQUENCE: 1

Met Thr Arg Val Leu Gln Gly Val Leu Pro Ala Leu Pro Gln Val Val
1               5                   10                  15

Cys

<210> SEQ ID NO 2
<211> LENGTH: 13
<212> TYPE: PRT
<213> ORGANISM: Unknown
<220> FEATURE:
<223> OTHER INFORMATION: Fragment of peptide immunoregulator
```

-continued

```
<400> SEQUENCE: 2

Leu Gln Gly Val Leu Pro Ala Leu Pro Gln Val Val Cys
1               5                   10

<210> SEQ ID NO 3
<211> LENGTH: 10
<212> TYPE: PRT
<213> ORGANISM: Unknown
<220> FEATURE:
<223> OTHER INFORMATION: Fragment of peptide immunoregulator

<400> SEQUENCE: 3

Val Leu Pro Ala Leu Pro Gln Val Val Cys
1               5                   10

<210> SEQ ID NO 4
<211> LENGTH: 10
<212> TYPE: PRT
<213> ORGANISM: Unknown
<220> FEATURE:
<223> OTHER INFORMATION: Fragment of peptide immunoregulator

<400> SEQUENCE: 4

Leu Gln Gly Val Leu Pro Ala Leu Pro Gln
1               5                   10

<210> SEQ ID NO 5
<211> LENGTH: 4
<212> TYPE: PRT
<213> ORGANISM: Unknown
<220> FEATURE:
<223> OTHER INFORMATION: Fragment of peptide immunoregulator

<400> SEQUENCE: 5

Met Thr Arg Val
1

<210> SEQ ID NO 6
<211> LENGTH: 4
<212> TYPE: PRT
<213> ORGANISM: Unknown
<220> FEATURE:
<223> OTHER INFORMATION: Fragment of peptide immunoregulator

<400> SEQUENCE: 6

Gln Val Val Cys
1

<210> SEQ ID NO 7
<211> LENGTH: 4
<212> TYPE: PRT
<213> ORGANISM: Unknown
<220> FEATURE:
<223> OTHER INFORMATION: Fragment of peptide immunoregulator

<400> SEQUENCE: 7

Cys Leu Gln Gly
1

<210> SEQ ID NO 8
<211> LENGTH: 4
<212> TYPE: PRT
<213> ORGANISM: Unknown
<220> FEATURE:
<223> OTHER INFORMATION: Fragment of peptide immunoregulator

<400> SEQUENCE: 8
```

```
Leu Gln Gly Val
1

<210> SEQ ID NO 9
<211> LENGTH: 7
<212> TYPE: PRT
<213> ORGANISM: Unknown
<220> FEATURE:
<223> OTHER INFORMATION: Fragment of peptide immunoregulator

<400> SEQUENCE: 9

Val Leu Pro Ala Leu Pro Gln
1               5

<210> SEQ ID NO 10
<211> LENGTH: 8
<212> TYPE: PRT
<213> ORGANISM: Unknown
<220> FEATURE:
<223> OTHER INFORMATION: Fragment of peptide immunoregulator

<400> SEQUENCE: 10

Gly Val Leu Pro Ala Leu Pro Gln
1               5

<210> SEQ ID NO 11
<211> LENGTH: 7
<212> TYPE: PRT
<213> ORGANISM: Unknown
<220> FEATURE:
<223> OTHER INFORMATION: Fragment of peptide immunoregulator

<400> SEQUENCE: 11

Gly Val Leu Pro Ala Leu Pro
1               5

<210> SEQ ID NO 12
<211> LENGTH: 6
<212> TYPE: PRT
<213> ORGANISM: Unknown
<220> FEATURE:
<223> OTHER INFORMATION: Fragment of peptide immunoregulator

<400> SEQUENCE: 12

Val Leu Pro Ala Leu Pro
1               5
```

IMMUNOREGULATOR

CROSS REFERENCE TO RELATED APPLICATIONS

This application is a continuation-in-part of U.S. patent application Ser. No. 09/716,777, filed Nov. 20, 2000, which is a continuation of co-pending International Application PCT/NL99/00313, filed May 20, 1999, designating the United States of America, which itself claims priority from EP 98201695.8, filed on May 20, 1998, and EP 98202706.2, filed on Aug. 12, 1998, the contents of all these applications are incorporated by this reference in their entirety.

TECHNICAL FIELD

The invention generally relates to the field of immunology, and specifically to the field of immune-mediated disorders such as allergies, auto-immune disease, transplantation-related disease and inflammatory disease.

BACKGROUND

The immune system produces cytokines and other humoral factors to protect the host when threatened by inflammatory agents, microbial invasion, or injury. In most cases, this complex defense network successfully restores normal homeostasis, but at other times, the immunological mediators may actually prove deleterious to the host. Some examples of immune disease and immune system-mediated injury have been extensively investigated including anaphylactic shock, auto-immune disease, and immune complex disorders.

Recent advances in humoral and cellular immunology, molecular biology and pathology have influenced current thinking about auto-immunity being a component of immune-mediated disease. These advances have increased our understanding of the basic aspects of antibody, B-cell, and T-cell diversity, the generation of innate (effected by monocytes, macrophages, granulocytes, natural killer cells, mast cells, γδ T-cells, complement, acute phase proteins, and such) and adaptive (T- and B-cells and antibodies) or cellular and humoral immune responses and their interdependence, the mechanisms of self-tolerance induction and the means by which immunological reactivity develops against auto-antigenic constituents.

Since 1900, a central theme of immunology has been that the immune system does not normally react to itself. However, it has recently become apparent that auto-immune responses are not as rare as once thought, and that not all auto-immune responses are harmful. Some responses play a distinct role in mediating the immune response in general. For example, certain forms of auto-immune response such as recognition of cell surface antigens encoded by the major histocompatibility complex ("MHC") and of anti-idiotypic responses against self idiotypes are important, indeed essential, for the diversification and normal functioning of the intact immune system.

Apparently, an intricate system of checks and balances is maintained between various subsets of cells (i.e., T-cells) of the immune system, thus providing the individual with an immune system capable of coping with foreign invaders. In that sense, auto-immunity plays a regulating role in the immune system.

However, it is now also recognized that an abnormal auto-immune response is sometimes a primary cause of, and at other times a secondary contributor to, many human and animal diseases. Types of auto-immune disease frequently overlap, and more than one auto-immune disorder tends to occur in the same individual, especially in those with auto-immune endocrinopathies. Auto-immune syndromes may be mediated with lymphoid hyperplasia, malignant lymphocytic or plasma cell proliferation and immunodeficiency disorders such as hypogammaglobulinaemie, selective Ig deficiencies and complement component deficiencies.

Auto-immune diseases, such as systemic lupus erythematosis ("SLE"), diabetes, rheumatoid arthritis, postpartum thyroid dysfunction, auto-immune thrombcytopenia, to name a few, are characterized by auto-immune responses, for example, directed against widely distributed self-antigenic determinants, or directed against organ- or tissue-specific antigens. Such disease may follow abnormal immune responses against only one antigenic target, or against many self-antigens. In many instances, it is not clear whether auto-immune responses are directed against unmodified self-antigens or self-antigens that have been modified or resemble any of the numerous agents such as viruses, bacterial antigens and haptenic groups.

As of yet, no established unifying concept exists to explain the origin and pathogenesis of the various auto-immune disorders. Studies in experimental animals support the notion that auto-immune diseases may result from a wide spectrum of genetic and immunological abnormalities which differ from one individual to another and may express themselves early or late in life depending on the presence or absence of many superimposed exogenous (viruses, bacteria) or endogenous (hormones, cytokines, abnormal genes) accelerating factors.

It is evident that similar checks and balances that keep primary auto-immune disease at bay are also compromised in immune mediated disorders, such as allergy (asthma), acute inflammatory disease such as sepsis or septic shock, chronic inflammatory disease (i.e., rheumatic disease, Sjögrens syndrome, multiple sclerosis), transplantation-related immune responses (graft-versus-host-disease, post-transfusion thrombocytopenia), and many others wherein the responsible antigens (at least initially) may not be self-antigens but wherein the immune response to the antigen is in principle not wanted and detrimental to the individual.

Sepsis is a syndrome in which immune mediators, induced by, for example, microbial invasion, injury or through other factors, induce an acute state of inflammation which leads to abnormal homeostasis, organ damage and eventually to lethal shock. Sepsis refers to a systemic response to serious infection. Patients with sepsis usually manifest fever, tachycardia, tachyapnea, leukocytosis, and a localized site of infection. Microbiologic cultures from blood or the infection site are frequently, though not invariably, positive. When this syndrome results in hypotension or multiple organ system failure ("MOSF"), the condition is called "sepsis" or "septic shock".

Initially, micro-organisms proliferate at a nidus of infection. The organisms may invade the bloodstream, resulting in positive blood cultures, or might grow locally and release a variety of substances into the bloodstream. Such substances, when of pathogenic nature, are grouped into two basic categories: endotoxins and exotoxins. Endotoxins typically consist of structural components of the micro-organisms, such as teichoic acid antigens from staphylococci or endotoxins from gram-negative organisms like LPS). Exotoxins (e.g., toxic shock syndrome toxin-1, or staphylococcal enterotoxin A, B or C) are synthesized and directly released by the microorganisms.

As suggested by their name, both of these types of bacterial toxins have pathogenic effects, stimulating the release of a large number of endogenous host-derived immunological mediators from plasma protein precursors or cells (monocytes/macrophages, endothelial cells, neutrophils, T-cells, and others).

It is, in fact, generally these immunological mediators which cause the tissue and organ damage associated with sepsis or septic shock. Some of these effects stem from direct mediator-induced injury to organs. However, a portion of shock-associated-organ dysfunction is probably due to mediator-induced abnormalities in vasculature, resulting in abnormalities of systemic and regional blood flow, causing refractory hypotension or MOSF (Bennett et al.).

The non-obese diabetic ("NOD") mouse is a model for auto-immune disease, in this case insulin-dependent diabetes mellitus ("IDDM"), in which its main clinical feature is elevated blood glucose levels (hyperglycemia). The elevated blood glucose level is caused by auto-immune destruction of insulin-producing β-cells in the islets of Langerhans of the pancreas (Bach et al. 1991, Atkinson et al. 1994). This is accompanied by a massive cellular infiltration surrounding and penetrating the islets (insulitis) composed of a heterogeneous mixture of CD4+ and CD8+ T-lymphocytes, B-lymphocytes, macrophages and dendritic cells (O'Reilly et al. 1991).

The NOD mouse represents a model in which auto-immunity against beta-cells is the primary event in the development of IDDM. Diabetogenesis is mediated through a multi-factorial interaction between a unique MHC class II gene and multiple, unlinked, genetic loci, as in the human disease. Moreover, the NOD mouse demonstrates beautifully the critical interaction between heredity and environment, and between primary and secondary auto-immunity. Its clinical manifestation is, for example, depending on various external conditions, most importantly on the micro-organism load of the environment in which the NOD mouse is housed.

As for auto-immunity demonstrable in NOD mice, most antigen-specific antibodies and T-cell responses are measured after these antigens were detected as self antigens in diabetic patients. Understanding the role these auto-antigens play in NOD mice may further allow to distinguish between pathogenic auto-antigens and auto-immunity that is an epiphenomenon.

In general, T-lymphocytes play a pivotal role in initiating the immune-mediated disease process (Sempe et al. 1991, Miyazaki et al. 1985, Harada et al. 1986, Makino et al. 1986). CD4+ T-cells can be separated into at least two major subsets, Th1 and Th2. Activated Th1 cells secrete IFN-γ and TNF-α, while Th2 cells produce IL4, IL-5 and IL-10. Th1 cells are critically involved in the generation of effective cellular immunity, whereas Th2 cells are instrumental in the generation of humoral and mucosal immunity and allergy, including the activation of eosinophils and mast cells and the production of IgE (Abbas et al. 1996). A number of studies have now correlated diabetes in mice and humans with Th1 phenotype development (Liblau et al. 1995, Katz et al. 1995). On the other hand, Th2 T-cells are shown to be relatively innocuous. Some have even speculated that Th2 T-cells, in fact, may be protective. Katz et al. have shown that the ability of CD4+ T-cells to transfer diabetes to naive recipients resided not with the antigen specificity recognized by the TCR per se, but with the phenotypic nature of the T-cell response. Strongly polarized Th1 T-cells transferred disease into NOD neonatal mice, while Th2 T cells did not, despite being activated and bearing the same TCR as the diabetogenic Th1 T-cell population. Moreover, upon co-transfer, Th2 T-cells could not ameliorate the Th1-induced diabetes, even when Th2 cells were co-transferred in 10-fold excess (Pakala et al. 1997).

The incidence of sepsis or septic shock has been increasing since the 1930's, and all recent evidence suggests that this rise will continue. The reasons for this increasing incidence are many: increased use of invasive devices such as intravascular catheters, widespread use of cytotoxic and immunosuppressive drug therapies for cancer and transplantation, increased longevity of patients with cancer and diabetes who are prone to develop sepsis, and an increase in infections due to antibiotic-resistant organisms. Sepsis or septic shock is the most common cause of death in intensive care units, and it is the thirteenth most common cause of death in the United States. The precise incidence of the disease is not known because it is not reportable; however, a reasonable annual estimate for the United States is 400,000 bouts of sepsis, 200,000 cases of septic shock, and 100,000 deaths from this disease.

Various micro-organisms, such as Gram-negative and Gram-positive bacteria, as well as fungi, can cause sepsis and septic shock. Certain viruses and rickettsiae probably can produce a similar syndrome. Compared with Gram-positive organisms, Gram-negative bacteria are somewhat more likely to produce sepsis or septic shock. Any site of infection can result in sepsis or septic shock. Frequent causes of sepsis are pyelonephritis, pneumonia, peritonitis, cholangitis, cellulitis, or meningitis. Many of these infections are nosocomial, occurring in patients hospitalized for other medical problems. In patients with normal host defenses, a site of infection is identified in most patients. However, in neutropenic patients, a clinical infection site is found in less than half of septic patients, probably because small, clinically in apparent infections in skin or bowel can lead to bloodstream invasion in the absence of adequate circulating neutrophils. Clearly, a need exists to protect against sepsis or septic shock in patients running such risks.

Recently, considerable effort has been directed toward identifying septic patients early in their clinical course, when therapies are most likely to be effective. Definitions have incorporated manifestations of the systemic response to infection (fever, tachycardia, tachyapnea, and leukocytosis) along with evidence of organ system dysfunction (cardiovascular, respiratory, renal, hepatic, central nervous system, hematologic, or metabolic abnormalities). The most recent definitions use the term systemic inflammatory response syndrome ("SIRS") emphasizing that sepsis is one example of the body's immunologically-mediated inflammatory responses that can be triggered not only by infections but also by noninfectious disorders, such as trauma and pancreatitis (for interrelationships among systemic inflammatory response (SIRS), sepsis, and infection, see *Crit. Care Med.* 20:864, 1992; For a review of pathogenic sequences of the events in sepsis or septic shock see *N. Engl J Med* 328:1471, 1993).

Toxic shock syndrome toxin (TSST-1) represents the most clinically relevant exotoxin, identified as being the causative agent in over 90% of toxic shock syndrome cases (where toxic shock is defined as sepsis or septic shock caused by super-antigenic exotoxins). Super-antigens differ from "regular" antigens in that they require no cellular processing before being displayed on an MHC molecule. Instead, they bind to a semi-conserved region on the exterior of the TCR and cause false "recognition" of self-antigens displayed on MHC class II (Perkins et al.; Huber et al. 1993). This results in "false" activation of both the T-cell and APC leading to proliferation, activation of effector functions and cytokine secretion. Due to the super-antigen's polyclonal activation of T-cells, a systemic-wide shock results due to excessive inflammatory cytokine release. (Huber et al. 1993, Miethke et al. 1992).

The inflammatory cytokines involved in sepsis are similar. These immunological mediators are tumor necrosis factor (TNF), interferon gamma (IFN-gamma), nitric oxide (NO) and interleukin 1 (IL-1), which are massively released by monocytes, macrophages and other leukocytes in response to bacterial toxins (Bennett et al., Gutierrez-Ramos et al 1997). The release of TNF and other endogenous mediators may lead to several pathophysiological reactions in sepsis, such as fever, leukopenia, thrombocytopenia, hemodynamic changes, disseminated intravascular coagulation, as well as leukocyte infiltration and inflammation in various organs, all of which may ultimately lead to death. TNF also causes endothelial cells to express adhesion receptors (selectins) and can activate neutrophils to express ligands for these receptors which help neutrophils to adhere with endothelial cell surface for adherence, margination, and migration into tissue inflammatory foci (Bennett et al.). Blocking the adhesion process with monoclonal antibodies prevents tissue injury and improves survival in certain animal models of sepsis or septic shock (Bennett et al.).

These findings, both with auto-immune disease, as well as with acute and chronic inflammatory disease, underwrite the postulated existence of cells regulating the balance between activated Th-sub-populations. Possible disturbances in this balance that are induced by altered reactivity of such regulatory T-cell populations can cause immune-mediated diseases, which results in absence or over-production of certain critically important cytokines (O'Garra et al. 1997). These Th-sub-populations are potential targets for pharmacological regulation of immune responses.

In general, immune-mediated disorders are difficult to treat. Often, broad-acting medication is applied, such as treatment with corticosteroids or any other broad acting anti-inflammatory agent that in many aspects may be detrimental to a treated individual.

In general, there is a need for better and more specific possibilities to regulate the checks and balances of the immune system and treat immune-mediated disorders.

SUMMARY OF THE INVENTION

This invention provides an immunoregulator ("IR"), use of an IR in preparing a pharmaceutical composition for treating an immune-mediated disorder, a pharmaceutical composition and a method for treating an immune-mediated disorder.

"Immune mediated disorders" as described herein include chronic inflammatory disease, such as diabetes type I or II, rheumatic disease, Sjögrens syndrome, multiple sclerosis, transplantation-related immune responses such as graft-versus-host-disease, post-transfusion thrombocytopenia, chronic transplant rejection, pre-eclampsia, atherosclerosis, asthma, allergy and chronic auto-immune disease, and acute inflammatory disease, such as (hyper)acute transplant rejection, septic shock and acute auto-immune disease. Auto-immune diseases are a group of disorders of, in general, unknown etiology. In most of these diseases, production of autoreactive antibodies and/or autoreactive T lymphocytes can be found. An auto-immune response may also occur as manifestation of viral or bacterial infection and may result in severe tissue damage, for example destructive hepatitis because of Hepatitis B virus infection.

Auto-immune diseases can be classified as organ specific or non-organ specific depending on whether the response is primarily against antigens localized in particular organs or against wide-spread antigens. The current mainstay of treatment of auto-immune diseases is immune suppression and/or, because of tissue impairment, substitution of vital components like hormone substitution. However, immunosuppressive agents, such as steroids or cytostatic drugs, have significant side effects which limits their application. Now, the use of more specific immunoregulatory drugs is provided by the invention in the treatment of auto-immune disease and other inflammations. Based on the immunoregulatory properties as described below, e.g., by regulating the Th1/Th2 ratio, modulating dendritic cell differentiation, the low side-effect profile, the initial clinical observations, etc., it shows these preparations to be very helpful in the treatment of patients with immune-mediated inflammation, such auto-immune disease.

A non-limiting list of auto-immune diseases includes: Hashimoto's thyroditis, primary mysxoedema thyrotoxicosis, pernicious anaemia, auto-immune atrophic gastritis, Addison's disease, premature menopause, insulin-dependent diabetes mellitus, stiff-man syndrome, Goodpasture's syndrome, myasthenia gravis, male infertility, pemphigus vulgaris, pemphigoid, sympathetic ophthalmia, phacogenic uveitis, multiple sclerosis, auto-immune hemolytic anaemia, idiopathic thrombocytopenic purpura, idiopathic leucopenia, primary biliary cirrhosis, active chronic hepatitis, cryptogenic cirrhosis, ulcerative colitis, Sjögren's syndrome, rheumatoid arthritis, dermatomyositis, polymyositis, scleroderma, mixed connective tissue disease, discoid lupus erythematosus, and systemic lupus erythematosis.

The invention further provides a method for selecting an immunoregulator. The method comprises determining the therapeutic effect of an immunoregulator by subjecting an animal prone to show signs of diabetes to a composition comprising a peptide fraction thereof, and determining or monitoring the animal for the development of diabetes.

Similarly, a method for selecting an immunoregulator comprises determining the therapeutic effect of an immunoregulator by subjecting an animal prone to show signs of septic shock to a composition comprising a peptide fraction thereof, and determining or monitoring the animal for the development of septic shock. The septic shock model also being a fast read-out model for the determination of anti-diabetic activity.

Preferably, the peptide or peptides in the composition tested in a method or methods according to the invention are obtained from a peptide having at least 10 amino acids such as a peptide having an amino acid sequence MTRVLQGV-LPALPQVVC (SEQ ID NO 1) or a functional fragment (e.g., a breakdown product having similar efficacy) or a functional analogue thereof. As used herein, "functional fragments" relates to the immunoregulatory effect or activity as, for example, can be measured in the septic shock or non-obese diagnostic ("NOD") mouse diabetes experimental model. Fragments can be somewhat (e.g., 1 or 2 amino acids) smaller or larger on one or both sides.

Surprisingly, it has been found in the test systems provided herein, that a range of beta-hCG breakdown products provides a cascade of peptide immunoregulators with a host of functions. Even more surprisingly, the immunoregulator peptides are interrelated and derived from one another and can also be produced synthetically. The invention provides for the use of such an immunoregulating peptide ("IR") in preparing a pharmaceutical composition for treating an immune-mediated disorder, the resulting pharmaceutical composition, and a method for treating an immune-mediated disorder.

A useful peptide found in a method according to the invention can be further modified or improved for one or more characteristics by known peptide synthesis skills, for example by identifying functional analogues with replacement mapping techniques, by binding-site (PEPSCAN) detection technology and so on, and can comprise D- or L-amino acids or modified amino acids at one or more (or all) places in the desired sequence. Also, peptide derivatives can be made, such as by circularization (for example by providing with (terminal) cysteines, dimerization or multimerization, by linkage to lysine or cysteine or other side-chains that allow linkage or multimerization, repeated, brought in tandem configuration, conjugated or otherwise linked to carriers known in the art, if only by a labile link that allows dissociation). Of course, newly developed peptide compositions or derivatives can be tested according to the methods provided herein.

Immune-mediated disorders as described herein include chronic inflammatory disease, such as diabetes type I or II, rheumatic disease, Sjögrens syndrome, multiple sclerosis, transplantation-related immune responses such as graft-versus-host-disease, post-transfusion thrombocytopenia, chronic transplant rejection, pre-eclampsia, atherosclerosis, asthma, allergy and chronic auto-immune disease, and acute inflammatory disease, such as (hyper)acute transplant rejection, septic shock and acute autoimmune disease. Autoimmune diseases are a group of disorders of generally unknown etiology. In most of these diseases, production of autoreactive antibodies and/or autoreactive T lymphocytes can be found. An autoimmune response may also occur as manifestation of viral or bacterial infection and may result in severe tissue damage, for example destructive hepatitis due to Hepatitis B virus infection. It is preferred that the therapeutic effect is further measured by determining relative ratios and/or cytokine activity of lymphocyte subset-populations in the animal, or wherein the therapeutic effect is further measured by determining enzyme levels in the animal. Using a selection method as provided herein, the invention also provides an immunoregulator and a pharmaceutical composition comprising an immunoregulator.

The invention provides among others an immunoregulator (IR) obtainable or derivable from a urinary metabolite of hCG, in particular from (nicked) forms of beta-hCG or breakdown products thereof, or (synthetic) peptide homologues or analogues thereof.

Autoimmune diseases can be classified as organ specific or non-organ specific depending on whether the response is primarily against antigens localized in particular organs, or against wide-spread antigens. The current mainstay of treatment of autoimmune diseases is immune suppression and/or (because of tissue impairment) substitution of vital components like hormone substitution. However, immunosuppressive agents such as steroids or cytostatic drugs have significant side effects, which limit their application. Now, the use of more specific immunoregulatory drugs is provided by the invention in the treatment of autoimmune disease and other inflammations based on the immunoregulatory properties, for example, the capacities to regulate the Th1/Th2 ratio, to modulate dendritic cell differentiation, their low side-effect profile, and the beneficial clinical effects, etc. It shows these urinary metabolite preparations or synthetic analogues thereof to be very helpful in the treatment of patients with immune-mediated inflammation, such as autoimmune disease.

In one embodiment, the invention provides an immunoregulator capable of down-regulating Th1 cell levels and/or up-regulating Th2 cell levels, or influencing their relative ratio in an animal. A preferred immunoregulator is obtainable from urine or other sources of bodily products, such as serum, whey, placental extracts, cells or tissues. As used herein, "obtainable" refers to directly or indirectly obtaining the IR from the source, an IR is, for example, obtained via chemical synthesis or from animal or plant sources in nature.

In a preferred embodiment, the invention allows for the regulation of relative ratios and/or cytokine activity of lymphocyte subset-populations in a diseased animal (e.g., human), preferably where these lymphocyte subset-populations comprise Th1 or Th2 populations. In general, naive $CD4^+$ helper T lymphocytes (Th) develop into functionally mature effector cells upon stimulation with relevant antigenic peptides presented on the major histocompatibility complex ("MHC") class II molecules by antigen-presenting cells ("APC").

Based on the characteristic set of cytokines produced, Th cells are commonly segregated into at least two different sub-populations: Th1 cells producing exclusively interleukin-2 (IL-2), interferon-gamma (IFN-$\gamma$), and lymphotoxin, and Th2 cells which produce IL-4, IL-5, IL6, IL10, and IL-13. These Th1 and Th2 subsets appear to be extremes in cytokine production profiles and, within these polarized subsets, individual Th cells exhibit differential rather than co-ordinated cytokine gene expression. These subsets develop from common Th precursor cells (Thp) after triggering with relevant peptides into Th0 cells producing an array of cytokines, including IL-2, IL-4, IL-5 and IFN-$\gamma$. These activated Th0 cells subsequently polarize into the Th1 or Th2 direction based on the cellular and cytokine composition of their micro-environment.

Antigen-presenting cells, like the various subsets of dendritic cells besides subsets of macrophages, largely determine this polarization into Th1 or Th2 subset development. The Th1-Th2 subsets appear to cross-regulate each other's cytokine production profiles, mainly through IFN-$\gamma$ and IL-10, and, from this concept, it was rationalized that disturbances in the balance between these two subsets may result in different clinical manifestations [5]. IL-12 is a dominant factor promoting Th1 subset polarization and dendritic cells and macrophages produce IL-12. Moreover, IL-12 induces IFN-$\gamma$ production by T cells and natural killer ("NK") cells. Recently, it was reported that IL-18 acts synergistically with IL-12 to induce Th1 development. Polarization of Th2 cells is critically dependent on the presence of IL-4 produced by T cells or basophils and mast cells. APC-derived IL-6 has also been shown to induce small amounts of IL-4 in developing Th cells. IL-10 and APC-derived prostaglandin $E_2$ ($PGE_2$) inhibit IL-12 production and Th1 priming.

The Th1-Th2 paradigm has been useful in correlating the function of Th1 cells with cell-mediated immunity (inflammatory responses, delayed type hypersensitivity, and cytotoxicity) and Th2 cells with humoral immunity. In general, among infectious diseases, resistance to intracellular bacteria, fungi, and protozoa is linked to mounting a successful Th1 response. Th1 responses can also be linked to pathology, like arthritis, colitis and other inflammatory states. Effective protection against extracellular pathogens, such as helminths, mostly requires a Th2 response, and enhanced humoral immunity may result in successful neutralization of pathogens by the production of specific antibodies.

In another embodiment, the invention provides an immunoregulator capable of modulating dendritic cell differentiation. The selective outgrowth of Th1 vs. Th2 type cells is dependent on the interaction of precursor Th cells with antigen-presenting cells (APC) carrying the relevant peptide in conjunction with their MHC class II molecules. Cytokines released by the APC and present during the initial interaction between dendritic cells and the pertinent T cell receptor carrying T cells drive the differentiation in to Th1 vs. Th2 subsets. Recently, two different precursors for DC (myeloid vs. lymphoid) have been described in man. Selective development of DC1 from myeloid precursors occurs after stimulation with CD40 ligand or endotoxin, and results in high production of IL-12. Lymphoid precursors give rise to DC2 cells after CD40 ligand stimulation, and produced IL-1, IL-6 and IL-10. These cytokines are of prime importance in driving the development of the activated Th cell: IL-4 is required for the outgrowth of Th2 type cells which can be greatly enhanced by the presence of IL-10, while selective differentiation to Th1 type cells is exclusively dependent on the presence of IL-12. Since DC1 are characterized by the production of IL-12, they will primarily induce outgrowth of Th1 type cells, while DC2 produce IL-10 and selectively promote Th2 development in the presence of exogenous IL-4. It is shown herein, that an IR as provided by the invention is capable of regulating or modulating DC activity and differentiation, thereby allowing selective differentiation and activity of Th1 and/or Th2 cells.

In one embodiment, the invention provides an immunoregulator comprising an active component obtainable from a mammalian chorionic gonadotropin ("CG") preparation or a (synthetic) peptide analogue thereof. The active component is capable of stimulating splenocytes obtained from a NOD mouse. The active component can be functionally related to the screened active compound, for example, allowing regulating or modulating DC activity and differentiation, or allowing selective differentiation and activity of Th1 and/or Th2 cells, in case of chronic inflammation (e.g., diabetes or chronic transplant rejection) as shown, for example, later herein wherein stimulated splenocytes delay the onset of diabetes in a NOD-severe-combined-immunodeficient mouse reconstituted with the splenocytes, or wherein the active component inhibits gamma-interferon production of splenocytes obtained from a NOD mouse, or wherein the active component stimulates interleukin-4 production of splenocytes obtained from a NOD mouse.

In another embodiment, the invention provides an immunoregulator comprising an active component obtainable from a mammalian CG preparation, the active component capable of protecting a mouse against a lipopolysaccharide induced septic shock. This allows for regulating or modulating DC activity and differentiation. It also allows for selective differentiation and activity of Th1 and/or Th2 cells and, in case of acute inflammation, such as seen with shock or (hyper)acute transplantation rejection, the active component reduces ASAT or other relevant plasma enzyme levels during or after organ failure, as commonly seen with shock.

Although the immunoregulator according to the invention is easily obtained as an urinary gonadotropin metabolite, or a breakdown product from urine, (e.g., when the mammalian CG preparation is urine derived), other sources, such as serum, cells, or tissues comprising gonadotropin are applicable as well. Also, an immunoregulator according to the invention capable of regulating Th1 and/or Th2 cell activity, and/or capable of modulating dendritic cell differentiation, can be provided from the sources. In particular, the immunoregulator can be provided and derived from beta-hCG, preferably from nicked beta-hCG chains. Of course, such a peptide, or functional equivalent thereof is obtainable or derivable from other mammalian gonadotropins, as explained herein previously. One such peptide is for example capable of protecting against septic shock or other immune-mediated disorders. Preferably, the peptide immunoregulator is obtained from a peptide having at least 10 amino acids such as a peptide having an amino acid sequence MTRVLQGVLPALPQVVC (SEQ ID NO 1) or functional fragment (e.g., a breakdown product) or functional analogue thereof. As used herein, the "functional" in "functional fragments" relates to the immunoregulatory effect or activity as for example can be measured in the septic shock or NOD mouse experimental model. Fragments can be somewhat smaller or larger on one or both sides (e.g, 1 or 2 amino acids), while still providing functional activity.

As used herein, a "functional analogue" not only relates to analogues or homologous peptides from MIF or MIF-like proteins, but includes LH, PMSG, or gonadotropin-like proteins, be it modified by glycosylation or modification with unidentified amino acids or non-protein amino acids, and also includes synthetic peptide analogues that can be made with known peptide synthesis skills, for example, by identifying functional analogues with replacement mapping techniques, PEPSCAN detection technology, and so on. It can also comprise D- or L-amino acids or modified amino acids at one or more (or all) places in the desired sequence. Also, peptides can be circularized (for example, by providing the peptide with (terminal) cysteines), dimerized or multimerized (e.g., by linkage to lysine or cysteine or other side-chains that allow linkage or multimerization), repeated, brought in tandem configuration, conjugated or otherwise linked to carriers known in the art, if only by a labile link that allows dissociation.

Preferably, an immunoregulator as provided by the invention is obtained or derived from a gonadotropin from a pregnant mammal, such as a human. It may be obtained, for example, from a pharmacological preparation prepared to contain (placental) gonadotropins such as pregnant mare serum gonadotropin (PMSG), or pregnant mouse uterus extract (PMUE) extracted from uteri of gravid mice, or human chorionic gonadotropin ("hCG or HCG") found in the blood or urine of a pregnant woman. An IR as provided by the invention can, but need not be, associated with gonadotropin as, for example, is present in the urine of the first trimester of pregnancy (IR) and in commercial hCG preparations.

In particular, IR can inhibit or regulate auto-immune and acute- and chronic-inflammatory diseases. TNF and IFN-γ are pathologically involved in acute inflammatory disease such as sepsis or septic shock, and also in auto-immune and chronic inflammatory diseases. Since IR has the ability to regulate T-cell sub-populations and inhibit TNF and IFN-gamma, IR can be used to treat, suppress or prevent immune mediated disorders such as sepsis or septic shock (acute inflammatory disease) as well as auto-immune diseases or chronic inflammatory diseases such as, for example, SLE, diabetes, rheumatic disease, Sjögrens syndrome, multiple sclerosis, post-partum thyroid dysfunction, thyroid dysfunction related to dementias such as Alzheimer's disease, auto-immune thrombocytopenia, allergies, chronic inflammatory disease, and transplantation related immune responses.

Furthermore, the invention provides for the detection of the genetic predisposition for immune-mediated disorders, wherein individuals with particular isoforms or amino acid variations in hCG or hCG derived peptides or immunoregulators are predisposed to certain disorders. Once this information is known, the invention provides the genetically predisposed individual with the proper peptide immunoregulator via, for example, gene therapy.

In particular, an immunoregulator according to the invention is provided wherein the functional fragment comprises a peptide having at least 10 amino acids and having an amino acid sequence LQGVLPALPQVVC (β45+β48) (SEQ ID NO 2), or VLPALPQVVC (β48) (SEQ ID NO 3) or LQGVLPALPQ (β45) (SEQ ID NO 4), or a functional analogue thereof, herein also called "immunoregulating peptide-K" or "IR-K". The immunoregulator comprising the peptide (or mixtures of peptides) having the desired length of about at least 10 amino acids (and especially when bound to a larger molecule such as when bound via its cysteine to another β-hCG fragment) generally regulates Th1/Th2 balance as well as innate immunity during an immune mediated disorder. For example, in septic shock LPS induced proliferation of splenocytes or diabetes may be accelerated or aggravated. Similar activity is provided by the relative short-chain peptide (third immunoregulator, 3–5 amino acids long) that comprises MTRV (SEQ ID NO 5) or MTR or QVVC (SEQ ID NO 6) or VVC or CLQG (SEQ ID NO 7) or LQGV (SEQ ID NO 8) or LQG (and optionally when bound to a larger molecule such as when bound via its cysteine to another beta-HCG fragment).

More in particular, a first immunoregulator is provided comprising a functional fragment comprising an amino acid sequence VLPALPQVVC (SEQ ID NO 3) or LQGVLPALPQ (SEQ ID NO 4) or functional analogue thereof which counteracts the regulatory activities of another. A second immunoregulator according to the invention comprises a functional fragment of an amino acid sequence of from 6 to 9 amino acids (herein also called IR-Kb), such as VLPALPQ (SEQ ID NO 9) or GVLPALPQ (SEQ ID NO 10) or GVLPALP (SEQ ID NO 11) or VLPALP (SEQ ID NO 12) or functional analogue thereof. These sequences are capable of regulating Th1/Th2 balance as well as innate immunity during an immune mediated disorder. Thus, it is capable to reduce the clinical symptoms seen with immune-mediated disorders, such as septic shock or LPS induced proliferation of splenocytes or diabetes, instead of accelerating or aggravating these symptoms of immune-mediated disease. Examples of accelerating or aggravating are shown in the detailed description where the IR-Kb is capable of protecting a mouse against a lipopolysaccharide induced septic shock, or other acute or chronic immune-mediated disorder as explained herein. As there is an overlap between β45 and β48 peptide (β45; LQGVLPALPQ (SEQ ID NO 4) β48: VLPALPQVVC (SEQ ID NO 3)), we also tested denatured β45+β48 (LQGVLPALPQVVC (SEQ ID NO 2)) peptide for its effect on LPS induced proliferation (in vitro) and anti-shock activity (in vivo) in BALB/c mice. The results showed that denatured β45+β48 peptide inhibits LPS induced proliferation and in vivo septic shock. Breakdown products are generated via proteolysis, for example by lysis with leucocyte elastase, and can undergo further notification such as by the activity of (glutathione) transferases. One possible breakdown product of β45+β48 peptide is LQG which resembles glutathione (tripeptide of G, C, and Q with L-glutamate having an isopeptide bond with the amino moiety of L-cysteine). We have shown that an IR also inhibits (toxin) streptozotocin (SZ) induced diabetes in mice through destruction of beta-cells. One of the mechanisms involved in the destruction of pancreatic beta cells is the formation of reactive radicals (ROS, NO etc.) that also play an important role in the pathogenesis of many other diseases like nephropathy, obstructive nephropathy, acute and chronic renal allograft rejection, auto-immune diseases (like SLE, rheumatoid arthritis, diabetes, MS), AIDS, diseases related to angiogenesis, atherosclerosis, thrombosis and type II diabetes mellitus. So, it is likely that IR also acts as an 'anti-oxidant'. For example, breakdown products of β45+β48 such as LQG or CLQG (SEQ ID NO 7) peptides alone or in combination with certain carbohydrates or modified with unidentified amino acids or with non-protein amino acids such as β-alanine, γ-aminobutyric acid, ornithine, etc. possess immunomodulatory activity (IR).

Not intending to be bound by theory, the following may help explain the results obtained with the invention. IR-K and IR-Kb activity can be described as maintaining a Th1/Th2 balance, wherein the IR-K acts as if it is binding to an appropriate receptor, but not activating it, whereas IR-Kb binds to the receptor and activates it to modulate the Th1/Th2 balance in a beneficial way. IR-K and IR-Kb are therein both ligands of the same (or at least a conformationally similar or alike) receptor molecule. The receptor molecule is now also provided, since it and its activity are defined herein by the ligands.

For example, our results show that IR-Kb inhibits sepsis or septic shock caused by endotoxin or by exotoxin. IR-Kb, as provided by the invention, inhibits or counters immune mediated auto-immune diseases, chronic inflammatory diseases as well as acute inflammatory diseases.

The invention provides a pharmaceutical composition for treating an immune-mediated disorder such as an allergy, auto-immune disease, transplantation-related disease or acute or chronic inflammatory disease. Alternatively, or in addition, the invention provides an immunoregulator (IR) for, stimulating or regulating lymphocyte action. In one case, the immunoregulator comprise an active component capable of stimulating splenocytes obtained from a 20-week-old female NOD mouse, the stimulated splenocytes delay the onset of diabetes in a NOD-severe-combined-immunodeficient (NOD.scid) mouse reconstituted at 8 weeks old with the splenocytes, or comprise an active component functionally related thereto.

In one embodiment, the invention provides a pharmaceutical composition or immunoregulator wherein the active component is capable of inhibiting gamma-interferon production or stimulating interleukin-4 production of splenocytes obtained from a 20-week-old female NOD mouse. Clinical grade preparations of gonadotropins (such as hCG and PMSG) have long been used to help treat reproductive failure in situations where follicular growth or stimulation of ovulation is desired. The preparations are generally obtained from serum or urine, and often vary in degree of purification and relative activity, dependent on the initial concentration in serum or urine and dependent on the various methods of preparation used. In a particular embodiment, the invention provides an immunoregulator comprising an active component obtainable or derivable from a mammalian CG preparation, the active component of which is capable of stimulating splenocytes obtained from a NOD mouse, or comprising an active component functionally related to the active compound, for example wherein the stimulated splenocytes are capable of delaying the onset of diabetes in a NOD-severe-combined-immunodeficient mouse reconstituted with the splenocytes.

The invention also provides an immunoregulator wherein the active component is capable of inhibiting gamma-interferon production obtained from a NOD mouse. The invention also provides an immunoregulator wherein the active component is capable of stimulating interleukin-4 production of splenocytes obtained from a NOD mouse.

An immunoregulator as provided by the invention (IR) has immune regulatory effects. In particular, IR can inhibit or regulate auto-immune and acute- and chronic-inflammatory diseases. TNF and IFN-gamma are pathologically involved in acute inflammatory disease such as sepsis or septic shock, and also in auto-immune and chronic inflammatory diseases. Since the IR has the ability to regulate T-cell sub-populations and inhibit TNF and IFN-gamma, the IR can be used to treat, suppress, or prevent immune mediated disorders such as sepsis or septic shock (acute inflammatory disease) as well as auto-immune disease or chronic inflammatory diseases such as SLE, diabetes, rheumatoid arthritis, post-partum thyroid dysfunction, auto-immune thrombocytopenia, allergies, chronic inflammatory disease (e.g., rheumatic disease, Sjögrens syndrome, multiple sclerosis), and transplantation related immune responses. The results provided herein show that IR-Kb inhibits sepsis or septic shock caused by endotoxin or by exotoxin. IR-Kb as provided herein inhibits or counters immune mediated auto-immune diseases, chronic inflammatory diseases, and acute inflammatory diseases.

The invention thus includes the use of an immunoregulator of the invention for the production of a pharmaceutical composition for treating an immune-mediated-disorder. The immune-mediated disorder may be chronic inflammation, diabetes, multiple sclerosis chronic transplant rejection, acute inflammation, septic shock, anaphylactic shock, acute or hyper acute transplant rejection, auto-immune disease, SLE, or rheumatoid arthritis, allergy, asthma, parasitic disease, in particular wherein the immune-mediated disorder comprises an overly strong immune response directed against an infectious agent, such as a virus or bacterium or wherein the immune-mediated disorder comprises pre-eclampsia or another pregnancy related immune-mediated disorder.

Use of IR-K as a contraceptive (e.g., as a "morning after" pill or contraceptive vaccine eliciting contraceptive or sterilizing antibodies in the vaccinated female mammal) is also provided. Use of IR-Kb is provided for facilitating fertility, especially in case where improved implantation is required. Especially, use is provided wherein the treatment comprises regulating innate immunity and/or relative ratios and/or cytokine activity of lymphocyte subset-populations in a treated individual, in particular wherein the subset populations comprise Th1 or Th2 cells. Thus, the invention provides a method for treating an immune-mediated-disorder comprising subjecting an animal to treatment with at least one immunoregulator according to the invention, in particular wherein the disorder comprises diabetes or sepsis.

The invention also provides a method for diagnosing or determining the risk of non-pregnancy related immune disorders associated with Th1/Th2 imbalance as demonstrated by an imbalance between IR-K and IR-Kb, as, for example, produced or derived from pituitary derived gonadotropin, especially in age-related disease such as auto-immune and chronic inflammatory disease (e.g., type II diabetes, rheumatic disease, thyroid dysfunction related mental disease such as dementias like Alzheimer's and others, and atherosclerosis and related disease). The method comprises determining the relative ratio of a relative long-chain peptide versus a relative short-chain peptide. The peptides derivable from breakdown of β-hCG, in particular, comprise determining the relative ratio of a relative long-chain peptide versus a relative short-chain peptide derived from breakdown a peptide having an amino acid sequence MTRVLQGVLPALPQVVC (SEQ ID NO 1). Examples include the relative long-chain peptide comprises an amino acid sequence LQGVLPALPQ (SEQ ID NO 4) or GVLPALPQ (SEQ ID NO 10) or VLPALPQ (SEQ ID NO 9) or GVL-PALP (SEQ ID NO 11), and the relative short-chain peptide may comprises MTRV (SEQ ID NO 5) or MTR or QVVC (SEQ ID NO 6) or VVC or LQGV (SEQ ID NO 8) or LQG. Detection of the long-chain peptides and short chain peptides is preferably achieved by immunological detection methods as known in the art. It does not matter if the peptides are modified by glycosylation or other modification with unidentified amino acids or non-protein amino acids.

The invention also provides a method for diagnosing or determining the risk of a pregnancy related immune-mediated disorder such as pre-eclampsia. It also relates to the outcome of pregnancy and/or pregnancy related immune disease (such as gestation diabetes mellitus (GDM)). The method comprises determining in a sample, preferably a urine sample, the relative ratio of a relative long-chain peptide versus a relative short-chain peptide. These peptides are derivable from breakdown of beta-HCG and, in particular, comprise determining the relative ratio of a relative long-chain peptide versus a relative short-chain peptide derived from breakdown a peptide having an amino acid sequence MTRVLQGVLPALPQVVC (SEQ ID NO 1), for example wherein the relative long-chain peptide comprises an amino acid sequence LQGVLPALPQ (SEQ ID NO 4) or GVLPALPQ (SEQ ID NO 10) or VLPALPQ (SEQ ID NO 9) or GVLPALP (SEQ ID NO 11), and wherein the relative short-chain peptide comprises MTRV (SEQ ID NO 5) or MTR or QVVC (SEQ ID NO 6) or VVC, or LQGV (SEQ ID NO 8) or LQG.

Anecdotal observations and laboratory studies indicated previously that hCG might have an anti-Kaposi's sarcoma and anti-human-immunodeficiency-virus effect (*Treatment Issues*, p. 15 (July/August 1995)). It has been observed that hCG preparations have a direct apoptotic (cytotoxic) effect on Kaposi's sarcoma (KS) in vitro and in immunodeficient patients and mice, a prohematopoetic effect on immunodeficient patients (Lunardi-Iskandar et al., *Nature* 375, 64–68; Gill et al., *New. Eng. J. Med.* 335, 1261–1269, 1996; U.S. Pat. No. 5,677,275), and a direct inhibitory antiviral effect on human and simian immunodeficiency virus (HIV and SIV respectively) (Lunardi-Iskandar et al., *Nature Med.* 4:428–434 (1998), U.S. Pat. No. 5,700,781).

The cytotoxic and anti-viral effects have also been attributed to an unknown hCG mediated factor ("HAF"), present in clinical grade preparations of hCG. However, commercial hCG preparations (such as CG-10, Steris Profasi, PREGNYL®, Choragon, Serono Profasi, APL), have various unintended effects. Analysis of several of these effects, (*AIDS*, 11: 1333–1340, 1997) showed that only some (such as CG-10, Steris Profasi) were KS-killing, whereas others (PREGNYL®, Choragon, Serono Profasi) were not. Also, recombinant subunits of (α or β) hCG were killing, but intact recombinant hCG was not. It was also found that the killing effect was also seen with lymphocytes. Therapy of KS has recently been directed to using beta-hCG for its anti-tumor effect (*Eur. J. Med Res.* 21:155–158 (1997)), and it was reported that the beta-core fragment isolated from urine had the highest apoptotic activity on KS cells (*AIDS*, 11:713–721 (1997)).

Recently, Gallo et al. reported the anti-Kaposi's Sarcoma, anti-HIV, anti-SIV and distinct hematopoietic effects of clinical grade crude preparations of human chorionic gonadotropin (hCG) (Lunardi-Iskandar et al. 1995, Gill et al. 1996, Lunardi-Iskandar et al. 1998). In contrast to previous studies, it was also claimed that the anti-tumor and anti-viral activity of hCG preparation was not due to the native hCG heterodimer (including its purified subunits or its major degradation product, the β-core). Instead the active moiety resided in an as yet unidentified hCG mediated factor (HAF). Whatever the true factor may be, these unidentified factors in several hCG preparations have anti-tumor activity through the selective induction of apoptosis, besides direct cytotoxic effects on the tumor cells. Furthermore, it was postulated that the anti-tumor activity could not be due to an immune-mediated response, since there was no infiltration of the tumor by mononuclear cells.

Moreover, the reported pro-hematopoietic effect of clinical grade hCG was noted in clinical studies in humans infected with HIV, (Lunardi-Iskandar et al. 1998) indicating that the hematopoietic effect is indirect, and caused by rescuing CD4+ cells otherwise killed by HIV through the anti-HIV activity of hCG.

The invention also provides an immunoregulator or a pharmaceutical composition for treating an immune-mediated disorder obtainable from an hCG preparation or a fraction derived thereof. The effects of the immunoregulator include a stimulating effect on lymphocyte populations (such as found in peripheral lymphocytes, thymocytes or splenocytes), instead of cytotoxic or anti-viral effects. The invention provides a method for treating an immune-mediated-disorder comprising subjecting an animal to treatment with at least one immunoregulator obtainable from a pregnant mammal. The treatment can be direct. For example, treatment can comprise providing the individual with a pharmaceutical composition, such as a hCG or PMSG preparation, comprising an immunoregulator as provided by the invention. It is also possible to provide the pharmaceutical composition with a fraction or fractions derived from a pregnant animal by, for example, sampling urine or serum or placental (be it of maternal or foetal origin) or other tissue or cells and preparing the immunoregulator comprising the active component from the urine or serum or tissue or cells by fractionation techniques known in the art (for example by gel permeation chromatography) and testing for its active component by stimulating a NOD mouse or its splenocytes as described. In particular, the preparation or component is preferably derived from a pregnant animal since an embryo has to survive a potentially fatal immunological conflict with its mother: developing as an essentially foreign tissue within the womb without triggering a hostile immune attack. Thus, to prevent this rejection "allograft", the immunological interaction between mother and fetus has to be suppressed, either for instance through lack of fetal-antigen presentation to maternal lymphocytes, or through functional "suppression" of the maternal lymphocytes. If fetal antigens are presented, maternal immune responses would be biased to the less damaging, antibody-mediated T helper 2 (Th2)-type. This would suggest that pregnant women are susceptible to overwhelming infection, which is not the case. Female individuals during pregnancy maintain or even increase their resistance to infection. Moreover, while the female individuals normally are more susceptible to immune diseases than male individuals, especially autoimmune diseases during pregnancy they are more resistant to these diseases.

The invention also provides a method for in vitro stimulation of lymphocytes and transferring the stimulated lymphocytes as a pharmaceutical composition to an animal for treating the animal for an immune mediated disorder. In a particular embodiment of the invention, a pharmaceutical composition is provided comprising lymphocytes stimulated in vitro with an immunoregulator provided by the invention.

In a preferred embodiment, the disorder is diabetes, yet other immune mediated disorders, such as acute and chronic inflammation, can also be treated. In yet another preferred embodiment, the disorder is sepsis or septic shock. The invention provides a method of treating an subject, preferably a mammal, such as a human.

In one embodiment, the invention provides a method comprising regulating relative ratios and/or cytokine activity or cytokine expression or marker expression of lymphocyte subset-populations in the animal, such as subset-populations that comprise Th1 or Th2 cells, or Th3 or Th8 cells, or other effector or regulatory T-cell populations.

The invention also provides an immunoregulator for use in a method according to the invention, and the use of the immunoregulator (preferably obtainable from a pregnant mammal) for producing a pharmaceutical composition for treating an immune-mediated-disorder, such as one selected from the group consisting of allergies, auto-immune disease (such as SLE or rheumatoid arthritis), transplantation-related disease and acute (such as septic or anaphylactic shock or acute or hyper acute transplant rejection) and chronic inflammatory disease (such as atherosclerosis, diabetes, multiple sclerosis or chronic transplant rejection). Furthermore, the invention provides for a use wherein the immune-mediated disorder comprises allergy, such as asthma or parasitic disease, or use wherein the immune-mediated disorder comprises an overly strong immune response directed against an infectious agent, such as a virus or bacterium. Often, in most of these diseases, production of autoreactive antibodies and/or autoreactive T lymphocytes can be found mounting or being part of a too strong immune response. This is for example seen with parasitic disease, where IgE production is overly strong or which disease is Th2 dependent, and detrimental for the organism, but also with (myco)bacterial infections such as TBC or leprosy. An autoimmune response may also occur as manifestation of viral or bacterial infection and may result in severe tissue damage, for example destructive hepatitis due to Hepatitis B virus infection, or as seen with lymphocytic choriomeningitis virus (LCMV) infections. The overly strong immune response is kept at bay with an immunoregulator as provided by the invention. Yet, another use provided by the invention, relates to the treatment of vascular disease, wherein radical damage (damage caused by free radicals) to cells and tissue is prevented or repaired by treatment with IR according to the invention and wherein the IR also acts as anti-oxidant directly or indirectly. For example, a determining event in the pathogenesis of diabetes I is the destruction of insulin-producing pancreatic beta cells. Strong evidence exists that the progressive reduction of the beta-cell mass is the result of a chronic autoimmune reaction. During this process, islet-infiltrating immune cells, islet capillary endothelial cells and the beta cell itself are able to release cytotoxic mediators. Cytokines, and NO, are potent beta-cell toxic effector molecules. The reactive radical NO mediates its deleterious effect mainly through the induction of widespread DNA strand breaks and other radicals, such as oxygen, through their effects on lymphocyte sub-populations such as Th1 and Th2 cells. This initial damage triggers a chain of events terminating in the death of the beta cell and disarray of the immune response.

Furthermore, an immunoregulator according to the invention is capable of regulating radical induced or directed cell-cell interactions or cell responses, specifically those interactions or responses of an immunological nature, for example, related to regulating interactions of the innate or adaptive immune system.

Again, not being bound by a theory of the invention, the following may help explain its beneficial aspects. Two arms of the immune system exist: the innate (non-specific) and adaptive (specific) systems, both of which have cellular and humoral components. Examples of cellular components of the innate immune system are monocytes, macrophages, granulocytes, NK cells, mast cells, gd T cell etc., while, examples of humoral components are lysozyme, complement, acute phase proteins and mannose-binding lectin (MBL). The major cellular components of the adaptive immune system are T and B cells, while examples of humoral components are antibodies. The adaptive system has been studied most because of its specificity, effectiveness at eliminating infection, and exclusive presence in higher multicellular organisms. The innate system is often considered primitive and thought to be 'unsophisticated'. However, the innate system not only persists but could also play a critical role in one of the most fundamental immune challenges—viviparity.

The innate system instigates an immune response by processing and presenting antigen in association with major histocompatibility complex (MHC) class I and II molecules to lymphocytes. A full response often requires an adjuvant (such as endotoxin) that, through interaction with the innate immune system, produces co-stimulatory surface molecules or cytokines. This determines the biological significance of antigens and communicates this information to the adaptive system. So, it instructs the adaptive system to either respond or not. So, these two great arms of the immune system not only influence each other, but also regulate each other at least at the cellular level through, for example, cytokines and co-stimulatory molecules etc.

Many physiological conditions and immune pathologies exist where these two systems are involved separately or in combination. For example, it has been shown that, in pregnancy, the maternal innate immune system is more stimulated, or for it has been proposed that type II diabetes mellitus is a disease of a chronic hyperactive innate immune system. Another example is the involvement of the innate immune system in listeriosis. Misregulation in the adaptive immune system may also lead to immune diseases like systemic or organ-specific autoimmunity, allergy, asthma etc, but it can also play a role in the maintenance of pregnancy and in the prevention of "allograft" rejection.

As previously mentioned, between the two, the adaptive system has been studied the most. Its regulation has also been studied the most. For example, it is known that the cytokine micro-environment plays a key role in T helper cell differentiation toward the Th1 or Th2 cell type during immune responses. IL-12 induces Th1 differentiation, whereas IL-4 drives Th2 differentiation. Recently, it has also been shown that subsets of dendritic cells (DC 1, DC2) provide different cytokine microenvironments that determine the differentiation of either Th1 or Th2 cells. In addition, negative feedback loops from mature T helper cell responses also regulate the survival of the appropriate dendritic cell subset and thereby selectively inhibit prolonged Th1 or Th2 responses. Moreover, development of Th1 responses can be antagonized directly by IL-4 and indirectly by IL-10, which inhibits the production of IL-12 and interferon-γ-inducing factor (IGIF) by macrophages stimulated by the innate immune response. Th2 cells dependent on IL-4 to proliferate and differentiate have been implicated in allergic and atopic manifestations, and in addition through their production of IL-4 and IL-10, have been suggested to play a role in tolerance. Specifically, it has been suggested that Th1 to Th2 switch may prevent the development of organ-specific autoimmune pathologies and required for the maintenance of pregnancy. Recently, it has become clear that distinct subsets of regulatory T cells are responsible for regulating both Th1 and Th2 responses and prevent the development of immune pathologies. One of the common features of many of these regulatory T cells is that their function is at least in part due the action of TGF-beta; this would be in keeping with the ability of TGF-beta to inhibit both Th1 and Th2 development while IL-10 could preferentially inhibit Th1 alone.

Furthermore, the invention provides an immunoregulator selected by a method according to the invention, a pharmaceutical composition comprising such a selected immunoregulator, and the use of the for the preparation of a pharmaceutical composition for the treatment of an immune-mediated disorder.

Purified IR is used to produce monoclonal antibodies and/or other specific reagents thereby facilitating the design of an IR-specific quantitative immunoassay. Also, single chain $F_v$ fragments are isolated by using the phage display technology with the use of a phage library containing a repertoire comprising a vast number of different specificities.

The present invention also encompasses the use of a combination of two or more immunoregulators, particular in the field of treatments for immune-mediated disorders such as auto-immune diseases and diabetes. The combination of two or more immunoregulators is intended to encompass combinations of all immunoregulators and peptides disclosed herein, as well as functional fragments (e.g breakdown products) or functional analogues thereof.

It is believed that peptides may act in concert to maintain homeostasis in immunoregulation to prevent or control imbalances in the immune system. For instance, a combination of peptide 1 (VLPALPQVVC) (SEQ ID NO 3) with recombinant hCG is able to inhibit the development of dominant Th1 CD4+ T cells. Alone, peptide and recombinant hCG are less desirable. This strongly suggests the need of an additional factor from hCG in order to achieve this effect. Other factors could be derived from different parts of hCG or from their homologous fragments that are known to exist, such as residues beta-CG6–40, beta-CG41–55, beta-CG55–92 and beta-CG90–110. In both the present application and International Patent Publication WO9959617, the NMPF activities demonstrated regulatory effects on innate and adoptive immune responses and are present in variable ratios. This helps explain the heterogeneity in results with commercial hCG preparations derived from pregnancy urine, even with a single commercial manufacturer.

DETAILED DESCRIPTION OF THE INVENTION

The immune system has two arms: the non-specific (innate) and specific (adaptive) immune defense, both of which have cellular and humoral components. T and B cells account for the antigen-specific cellular and humoral (antibodies) immune defense. On the other hand, monocytes/macrophages, granulocytes, NK cells, mast cells and likely also gd T cells are the cellular components of the innate immune system, while complement, acute phase proteins, lysozyme and mannose-binding lectin (MBL) are major humoral components of the innate immune system. The innate system is thought to play a critical role in the most fundamental immune challenge in mammals: viviparity.

The innate system instigates an immune response by processing and presenting antigen in association with major histocompatibility complex (MHC) class I and II molecules to lymphocytes, the so called signal 1. Full responses often require adjuvants (such as endotoxin), which, through interaction with the innate immune system, produce signal 2, in the form of co-stimulatory surface molecules or cytokines. Signal 2 appears to determine the biological significance of antigens and communicates this information to the adaptive system. In fact, it is believed that this signal 2 instructs the adaptive system to either respond or not (*Immunology Today* 20, 114–118). So, the innate system is an integral part of the specific immune defense.

During pregnancy, there are increased numbers of monocytes and granulocytes from the first trimester onwards. It has been found that, in normal pregnancy, circulating monocytes and granulocytes have activated phenotypes, in some ways comparable with changes observed in systemic sepsis (*Am. J. Obstet. Gynecol.* 179, 80–86). Others have shown increased monocyte phagocytosis and respiratory burst activity. Monocyte surface expression of the endotoxin receptor CD14 is increased, and in response to endotoxin monocytes from normal pregnant women produce more of the proinflammatory type I cytokine IL-12 (*Immunology Today*, 20:114–118). Other studies have similarly found granulocyte activation in pregnancy as well as changes in plasma levels of soluble innate factors typical of an acute phase response (*Am. J. Reprod. Immunol. Microbiol.* 15:19–23).

During pregnancy, the maternal immune system is modulated, resulting in suppression of maternal immune responses against the fetus, while maintaining the mother's resistance to infection. These factors include, but are not limited to, commercial hCG preparations derived from human pregnancy urine, β-hCG preparations, certain peptides of β-hCG, certain combinations of β-hCG peptides and certain gel filtration chromatography fractions of commercial hCG preparations and human pregnancy urine. Balance in these factors is crucial for proper regulation of the maternal immune system. For example, the over-activation of the innate system can cause problems in the progression of the pregnancy itself. Pre-eclampsia is one such condition characterized by hyperactivation of the innate immune system. Recently, it has been also suggested that the chronic imbalance between the two immune systems could be the basis of type II diabetes (non-insulin dependent diabetes mellitus) and other diseases as well (International Patent Application WO99-59617).

Several cytokines have been proposed to play an important role in balancing the immune system. One such cytokine which plays an important role in the innate immune defense and in the regulation of inflammatory responses is macrophage migration inhibitory factor (MIF).

MIF was originally identified by its ability to prevent the migration of macrophages out of capillary tubes. Since then, the expression of MIF activity has been found at a variety of inflammatory loci, suggesting its role in regulating the function of macrophages in host defense (*Science* 153:80–82; *J. Exp. Med.*, 137:275–288). First described as a T-cell cytokine, MIF was identified to be a peptide also released by pituitary cells in response to infection and stress (*Nature* 365, 756–759; *Nature* 377, 68–71). Originally considered to be the target of MIF action, monocytes and macrophages have been found to be a main source of MIF that is released after exposure to bacterial endo- and exotoxins and to cytokines. Once released, MIF induces the expression of proinflammatory mediators by macrophages and activated T cells, thereby strongly promoting inflammatory and immune responses (*Nature Medicine*, 6:164–170). The critical regulatory role of MIF within the immune system is further underscored by the finding that MIF is induced by glucocorticoids and has the unique ability to override the anti-inflammatory and immunosuppressive effects of glucocorticoids on macrophages and T cells. Thus, MIF and glucocorticoids function as a physiological counter-regulatory dyad that controls host inflammatory and immune responses (*Proc. Natl. Acad. Sci. (USA)* 93:7849–7854). Anti-MIF antibodies reduce the inflammation in experimental models of glomerulonephritis, arthritis, and allograft rejection, confirming the role of MIF in the regulation of inflammatory responses. Elevated concentrations of MIF have also been detected in alveolar air spaces of patients with the adult respiratory distress syndrome (ARDS). Recent studies have also shown that MIF is an important mediator of lethal endotoxemia and staphylococcal toxic shock, playing a critical role in the pathogenesis of septic shock. Besides the functions in the immune system, MIF has also other activities. For instance, MIF mRNA and protein are expressed in brain, embryonic eye lens and differentiating epidermal cells, suggesting its pivotal role in the regulation of the neuroendocrine system, cell growth and differentiation. A number of reports showed the presence of MIF in various organs and tissues: dermal vessels constitutively express MIF and can be strongly activated to express MIF in acute/chronic inflammations such as eczema and psoriasis. MIF expression on endothelium may provide an important differentiogenic signal for mononuclear phagocytes on their way to the tissue site.

One of the mechanisms of immune regulation that we detect during pregnancy is through modulation of the innate and adaptive immune defenses by IR. By way of example, but not limited to, acting directly or indirectly on regulatory cells of the APC compartment (such as DC1, DC2) or on lymphocytes (regulatory T cells), IR biases activated T lymphocytes towards Th2 immune response. The suppression of Th1 immune responses may be compensated by the stimulation of the innate immune defense by IR which could explain the maintenance of maternal resistance to infection. Recently, it has been shown that in some instances such compensatory mechanism (stimulation of innate immunity) could be more dominant and may account for abnormal pregnancy: pre-eclampsia.

Pre-eclampsia is a common, pregnancy-specific syndrome defined by clinical findings of elevated blood pressure combined with proteinuria and edema. The incidence has been reported to be between two and seven percent of all pregnancies. The clinical findings become manifested mostly late in pregnancy. The disease can progress rapidly, at times without warning, to a life-threatening disease. Expedient delivery initiates the resolution of pre-eclampsia but is a major cause of fetal and maternal morbidity and mortality.

Roberts et al. in their classic article gathered the evidence to invoke activation of maternal endothelium as an underlying process. Generalized maternal endothelial cell dysfunction allowed most, if not all, clinical aspects to be potentially explained by a single, unifying process: hypertension through disturbed endothelial control of vascular tone, fluid retention by increased endothelial permeability, and clotting dysfunction resulting from abnormal endothelial expression of procoagulant. Eclampsia can be ascribed to focal cerebral ischemia resulting from vasoconstriction, consistent with the evidence of changes detected by new cerebral imaging techniques. The liver dysfunction intrinsic to the HELLP (hemolysis, elevated liver enzymes, and low platelet count) syndrome could also be attributed to the effects of acute under perfusion.

Endothelial cells can be activated in several different ways that are potentially relevant to the origins of pre-eclampsia, and several candidate factors have emerged, including free fatty acids, lipoproteins, oxidized lipoproteins or lipid peroxides, tumor necrosis factor alpha (TNF-a), fibronectin degradation products, and deported syncytiotrophoblastic microvillous fragments. The source of the factors that lead to endothelial cell dysfunction has not been determined with certainty, but the evidence points to the placenta.

In addition to endothelial dysfunction, substantial published evidence exists that there is systemic activation of the maternal inflammatory cell responses in pre-eclampsia. Both granulocytes and monocytes are activated. There is increased release of the proinflammatory cytokines TNF-a and its 2 soluble receptors, interleukin 6 (IL-6) and soluble phospholipase A2 (an important mediator of inflammatory reactions) into the circulation. It is well known that the clotting system is abnormally activated, and complement systems are similarly affected. Postmortem observations indicate that in some circumstances the lethal pathologic condition resembles that of the Shwartzmann reaction, a particular form of inflammatory response to endotoxin that has been characterized in experimental animals.

Since these characteristics of pre-eclampsia resemble that of septic shock, we identified that also immunoregulating peptide (IR) factor(s) are involved in pre-eclampsia that can worsen septic shock or sepsis. We addressed this by using a high dose LPS animal model for septic shock. Since in the urine of pre-eclamptic patients high levels of nicked hCG b-subunits are present, we also tested these nicked subunits to find out whether they worsen septic shock and so behave like MIF, which is an important mediator of lethal endotoxemia and staphylococcal toxic shock.

EXAMPLES

Material and Methods

Immunoregulating peptide purification: To analyze the immunoregulating peptide from commercial hCG preparations, we used a Shimadzu HPLC system equipped with Alltech macrosphere size exclusion (GPC) column of 60 Å, 100 Å or 300 Å (250×4.6 mm and 300×7.5 mm). The separation ranges of the columns were 28,000–250, 2500–350,00 and 1,200,000–7,500 Dalton, respectively. External molecular weight standards were employed to calibrate the column elution positions. The markers used were: aprotinin (6,500 Da), cytochrome C (12,400), carbonic anhydrase (29,000), albumin (66,000) and blue dextran (2,000,000).

To analyze immunoregulating peptide, three different hCG preparations were used: immunoregulating peptide-PG (PREGNYL® Organon International, Oss, NL), immunoregulating peptide-A (APL; Weyth Ayerst; Philadelphia, US) and immunoregulating peptide-PR (Profasi; Serono, Rome, Italy). As running buffer 50 mm ammonium bicarbonate buffer containing ethanol (5%, vol/vol) was used. Sample load volume was 10–50 ml for the 250×4.6 mm column and 50–200 ml for the 300×7.5 mm column. The flow rate for the 250×4.6 mm and 300×7.5 mm columns were 0.5 ml/min for 45 min. And 1–2 ml/min for 45 min, respectively.

First trimester pregnancy urine (2 liters) was collected in a bottle from a healthy volunteer and was refrigerated until delivered at the laboratory within 2 days. Upon delivery, 1 gram per liter of sodium azide was added and the ph was adjusted to 7.2–7.4 with sodium hydroxide and allowed to sediment for 1 hour (h) at room temperature (RT). Approximately, 75% of the supernatant was decanted and the remainder close to the precipitate was centrifuged (10 min at 25,000 rpm at 40° C.) to remove sediment and added to the rest of the supernatants. The supernatants were filtered through 0.45 mm in a Minitan (Millipore) transversal filtration set-up. Subsequently, the filtrate (2 liter) was concentrated in an Amicon ultrafiltration set-up equipped with an YM Diopore membrane with a 10 kDa cut-off. The final volume (250 ml) was dialyzed against 2 changes of 10 liters of Milli Q water. Next the sample was further concentrated by 10 kDa cut-off in an Amicon ultrafiltration system to a final volume of 3 ml.

Mice used in sepsis or septic shock experiments: Female BALB/c mice of 8–12 weeks of age were used for all experiments. The animals were bred under specific pathogen-free conditions according to the protocols described in the Report of European Laboratory Animal Science Associations (FELASA), Working group on Animal Health, (*Laboratory Animals* 28: 1–24, 1994).

Injection protocols: For the endotoxin model, BALB/c mice were injected i.p. With 150–300 µg LPS (*E. coli* 026:B6; Difco Lab., Detroit, Mich., USA). Control groups were treated with PBS i.p. only. To test the effect of immunoregulating peptide, we treated BALB/c with an optimized dose of 700 IU of different hCG preparations, thereof derived fractions (10–50 mg) or from first trimester pregnancy urine (immunoregulating peptide-U) for 3 days and then injected with LPS intraperitoneally.

In order to determine whether immunoregulating peptide inhibited shock even after the shock induction, we also treated BALB/c mice with immunoregulating peptide i.p. After 3, 12, 24 and 36 h of injection with LPS. At different time points semi-quantitative sickness scores and survival rates were noted.

Semi-quantitative sickness measurements: Mice were scored for sickness severity using the following measurement scheme:

1 Percolated fur, but no detectable behavior differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund, sacrificed).

β-hCG Peptide and Anti-MIF Treatment:

Most urinary metabolites of hCG are a nicked form of beta-hCG. These forms of beta-hCG have peptide bond cleavages within the b-subunit. B48 (VLPALPQVVC) (SEQ ID NO 3) is one such peptide which has been shown to be associated with a natural urinary metabolite of hCG. To test the effect of this peptide on septic shock, we injected BALB/c mice with LPS and treated them 2 h later i.p. with b48-peptide (100 mg). In order to see whether possible breakdown products also have effect on septic shock, we incubated b48-peptide at 37° C. for three hours before testing the peptide in the septic shock model in BALB/c mice.

Previously (International Patent Application WO 99-59617), it was illustrated that immunoregulating peptide (IR) has an anti-diabetic effect. In order to test whether β48 peptide has an anti-diabetic effect, we performed transfer experiments. Total spleen cells were recovered from diabetic NOD mice and stimulated in vitro in RPMI+ supplemented with 10% FBS with coated anti-CD3 (145-2c11; 25 mg/ml) and IL-2 (50 U/ml) along with 300 IU/ml immunoregulating peptide (PREGNYL®) or b48 peptide (20 mg/ml). Culture flasks were then incubated at 37° C. in 5% of $CO_2$ in air for 48 h. After 48 h cells were twice washed with PBS and $20\times10^6$ cells were i.p. transferred into an 8-wk-old NOD-scid mouse (n=4).

In vitro/ex vivo LPS Stimulated Proliferation of Splenocytes:

After 48 h of septic shock induction in BALB/c mice by high dose LPS injection, spleen cells ($1\times10^6$ cells/ml) were recovered and restimulated in vitro with LPS (10 U/ml) in 96-well plates (round bottom). After 24 hours of culture, the LPS stimulated proliferation of splenocytes was measured via [$^3$H]tdr incorporation during the last 16 hours in culture. In other experiments splenocytes from non-treated BALB/c mice were isolated and in vitro stimulated ($1\times10^6$ cells/ml) with LPS in the presence or absence of different sources of immunoregulating peptide (37.5–600 IU/ml)(PREGNYL®, APL, Wyeth Ayerst; Profasi, Serono), immunoregulating peptide fractions (10–20 mg/ml), b-48 peptide or its breakdown products, anti-MIF or combinations of these products each at 10 mg/ml. After 24 hours of culture, the LPS stimulated proliferation of splenocytes was measured.

Results: Immunoregulating peptide purification: Samples of immunoregulating peptide from different sources (PREGNYL®, APL, PROFASI, pregnancy urine) were applied on the Macroshere GPC 300 Å column and eluted with ammonium bicarbonate. Three selected areas were fractionated, immunoregulating peptide-1 which elutes apparently with molecular weight of >25 kDa, immunoregulating peptide-2 which elutes apparently with molecular weight between the 25 kda–6 kda, and immunoregulating peptide-3 which elutes apparently with molecular weight <6 kda. All these fractions were lyophilized and were tested for anti-shock activity (shown elsewhere in this document). The lower molecular weight fraction (immunoregulating peptide-3) which elutes after the column volume was further fractionated on the Macrosphere GPC 60 Å column. All fractions were lyophilized and were also tested for anti-shock activity.

Immunoregulating peptide treatment in LPS-induced septic shock: To determine the effect of high-dose LPS treatment in immunoregulating peptide treated mice, BALB/c mice (n=6) were injected intraperitoneally with LPS (150 mg/kg) and survival was assessed daily for 5 days. PBS-treated BALB/c mice succumbed to shock from day 1 after high-dose LPS injection, with lower than 10% of mice alive on day 5. In contrast, 100% of the mice treated with immunoregulating peptide from source PREGNYL®, or its fractions immunoregulating peptide-1 or immunoregulating peptide-3 obtained from GPC 300 Å column, were alive on day 5 (P<0.001). While groups of mice treated with immunoregulating peptide-2 from source PREGNYL® or dexamethasone (data not shown) demonstrated around 25% of survivors. Not all commercial hCG preparations showed immunoregulating peptide activity. For example, immunoregulating peptide from source Profasi showed only partial anti-shock activity (around 40% survival). In addition, variability in immunoregulating peptide activity between different batches of the same source as well as variability of activity of same batch in time was observed. Treatment of BALB/c mice with APL before or after the shock induction, showed in a number of experiments acceleration of shock and early death.

In order to determine whether there are factor(s) present in hCG preparation that also accelerate shock and inhibit or counteract immunoregulating peptide activity, we further fractionated immunoregulating peptide-3 from a pretested active batch (containing anti-shock activity) and a non-active batch from source PREGNYL® on GPC 60 Å column. Three selected areas were fractionated, immunoregulating peptide-3.1 which elutes apparently with molecular weight of >2000 Da, immunoregulating peptide-3.2 which elutes apparently with molecular weight between 2000–300 Da and immunoregulating peptide-3.3 elutes apparently with molecular weight lower then 300 Da. All fractions were tested for anti-shock activity.

Results from these experiments revealed that anti-shock activity in a pretested active batch resided in a fraction immunoregulating peptide-3.2, while immunoregulating peptide-3.3 fraction from both (active and non-active) batches accelerated shock.

In order to determine whether immunoregulating peptide-3.3 inhibits the anti-shock activity of immunoregulating peptide-3.2, we added immunoregulating peptide-3.3 into immunoregulating peptide-3.2 in 10:1 ratio (100:10 mg) and injected the mixture i.p. in mice two hours after LPS injection (n=6). Data from these experiments showed that in all mice treated with immunoregulating peptide-3.2 fraction alone, septic shock was inhibited and they had sickness scores lower than 2, while this anti-shock activity of immunoregulating peptide-3.2 fraction was inhibited with immunoregulating peptide-3.3. Immunoregulating peptide-3.3 treatment alone accelerated shock and the treated mice died even earlier than PBS treated mice. Same trend of results were obtained in experiments, in which active and non-active batches from PREGNYL® were mixed and injected in BALB/c mice after septic shock induction (data not shown).

Ratio between immunoregulating peptide-3.2 and immunoregulating peptide-3.3: Next, we further purified immunoregulating peptide-3.2 and immunoregulating peptide-3.3 on GPC 60 Å column from active and non-active PREGNYL® batches, and from first trimester pregnancy urine and determined the ratio. We found that first trimester pregnancy urine having anti-shock activity had around 1:2.2 ratio (immunoregulating peptide-3.2: immunoregulating peptide-3.3). And non-active batch of PREGNYL® had 1:3.4 ratio, while the active batch of PREGNYL® had around 1:1 ratio.

Ex vivo LPS stimulated splenocytes proliferation: After 48 hours of LPS shock induction, splenocytes from PBS treated and immunoregulating peptide treated mice(from mice treated with either active PREGNYL(®, thereof derived immunoregulating peptide-3.2 or immunoregulating peptide-3.3 fractions, or APL preparation) were isolated and restimulated with LPS. After 24 hours of culture, LPS stimulated proliferation of splenocytes was measured. Reduction in LPS induced proliferation was observed after culture of splenocytes from immunoregulating peptide (active batch of PREGNYL® and thereof derived immunoregulating peptide-3.2 (1600 vs 1350 cpm) fraction treated BALB/c mice as compared to PBS treated mice (3500 cpm), while treatment by immunoregulating peptide(APL) or immunoregulating peptide-3.3 increased the LPS stimulated proliferation (6000 vs 7200 cpm). Comparable results were obtained when splenocytes from untreated BALB/c mice were in vitro stimulated with LPS in the presence of above mentioned additions(data not shown).

In vitro treatment with immunoregulating peptide from different sources, β48 peptide, denatured β48 peptide and anti-MIF: The major characteristics of pre-eclampsia resemble that of septic shock. Therefore we hypothesized that there might be also immunoregulating peptide (IR) factor(s)that are involved in pre-eclampsia and also worsen septic shock or sepsis. Above we have shown that immunoregulating peptide-3.3 is one such fraction which accelerates septic shock and increases in vitro/ex vivo LPS induced splenocytes proliferation, which is correlated with increase in the disease severity. In the urine of pre-eclamptic patients high levels of nicked hCG b-subunits are present. Therefore, we also tested whether these nicked subunits worse septic shock and so resemble immunoregulating peptide-3.3 fraction. Furthermore, MIF is an important mediator of lethal endotoxemia and staphylococcal toxic shock, so we also compared the effects of b-48 peptide and immunoregulating peptide on proliferation with anti-MIF and MIF.

These experiments revealed that anti-MIF has a trend to decrease LPS induced proliferation, similar as a pretested PREGNYL® batch that shows anti-shock activity (immunoregulating peptide-PG$^+$). Moreover, anti-MIF and immunoregulating peptide-PG$^+$ together work synergistically and decrease proliferation. Immunoregulating peptide from APL (immunoregulating peptide-A), non-active PREGNYL® batch (immunoregulating peptide-PG$^-$; without anti-shock activity) and b-48 peptide (immunoregulating peptide-K) increased the LPS induced proliferation as compared to LPS only. On the other hand, immunoregulating peptide-PG+ or denatured b-48 peptide (immunoregulating peptide-Kb) inhibited and decreased the LPS induced proliferation at least till the level of anti-MIF treatment alone. In vivo treatment of BALB/c mice with immunoregulating peptide-PG$^-$, immunoregulating peptide-K or immunoregulating peptide-A after septic shock induction accelerated the disease severity (at t=48 hrs 0–25% survival rate) as compared to PBS treated mice (at t=72 hrs 15% survival rate), while septic shock in BALB/c mice was completely inhibited by immunoregulating peptide-PG$^+$ or immunoregulating peptide-Kb.

In addition, our NOD spleen cells transfer experiments revealed that 22 days after transferring, NOD.scid mice receiving beta 48-peptide and PBS treated spleen cells were positive for diabetes and within a week they reached a blood glucose level above 30 mmol/l, while NOD.scid mice receiving immunoregulating peptide (PREGNYL®) treated spleen cells remained normal (blood glucose <8 mmol/l). 6 weeks after transferring, the PBS and b48 reconstituted NOD.scid mice looked very uncomfortable, while immunoregulating peptide mice group remained healthy. Mice from all groups were euthanized at this time.

Many physiological conditions and immune pathologies exist where adaptive and innate immune systems are involved separately or in combination. For example, it has been shown that in pregnancy the maternal innate immune system is more stimulated, and it has been proposed that type II diabetes mellitus is due to chronic hyperactivation of the innate immune system. Another example is the involvement of the innate immune system in listeriosis. Dysregulation in the adaptive immune system may also lead to immune diseases like systemic or organ-specific autoimmunity, allergy, asthma etc, and the adaptive immune system can also play a role in the maintenance of pregnancy and in the prevention of "allograft" rejection and chronic inflammation, presumably including atherosclerosis and related diseases.

While immunoregulating peptide and several of its fractions are able to inhibit the production of IFN-gamma in vitro and in vivo, this was not observed for immunoregulating peptide-3 (IR-P3) and recombinant hCG (rhCG). immunoregulating peptide-3 (IR-P3) and rhCG separately show no to moderate inhibition of the IFN-gamma production, but the combination of immunoregulating peptide-3 and rhCG gives a strong inhibition of the IFN-gamma production. This implies the need of immunoregulating peptide-3 for rhCG for at least its IFN-gamma inhibition capacity in these models, while NPMPF-1 and immunoregulating peptide-2 alone are capable to inhibit IFN-gamma production. This holds also for the anti-CD3 stimulated spleen cells obtained from in vivo treated NOD mice and for the polarization of T-helper cells to the Th2 phenotype. In our previous work we have also shown that IR has the potential to inhibit acute inflammatory responses, like in sepsis or septic shock. Thus, chronic as well as acute immune responses are modulated by immunoregulating peptide.

By way of example and not wishing to bound to theory, in pregnancy, a fetus has to survive potential maternal immune rejection, which is in part achieved through deviation of the maternal immune system towards Th2-type immune responses. But in this way, maternal immune suppression carries the attendant risk of infection, as is observed in transplant patients receiving corticosteroids or other immunosuppressive therapy. IR factor(s) obtainable at least from pregnancy urine and derived hCG preparations have the potential to modulate immune responses in such a way that the maternal rejection of the fetus is suppressed and that the mother maintains or even increases her resistance to infection. These and related factors are also responsible for the inhibition of immune diseases, particularly Th1-mediated immune diseases, during pregnancy.

By way of example and not wishing to be bound to theory, pregnancy apparently demands incompatible immune adjustments. On the one hand, adaptive immune responses during pregnancy are modulated at different cellular levels towards immune tolerance state (such as Th2-type) and, on the other hand, the maternal innate immune system is modulated for resistance to infection. The evidence is that components of the maternal innate immune system are systemically activated. There are increased numbers of monocytes and granulocytes from the first trimester onwards. It has also been found that in normal pregnancy circulating monocytes and granulocytes in the maternal blood have an activated phenotype, in some ways comparable with changes observed in systemic sepsis. Others have shown increased monocyte phagocytosis and respiratory burst activity, and an increased expression of endotoxin receptor CD14 on monocytes as well as an increased response to endotoxin: monocytes from normal women produce more of the proinflammatory cytokines like in septic shock. Many studies have similarly found granulocyte activation in pregnancy as well as changes in plasma levels of soluble innate factors typical of an acute phase response. Not all components of the innate system are activated in the maternal circulation. Most notably, cytotoxic activity and IFN-gamma production by NK cells are suppressed.

By way of example and not wishing to bound to theory, we propose that one of the mechanisms of immunoregulating peptide to modulate the immune response during pregnancy is the following: some IR factors during pregnancy can ensure that if T cells are activated, there is a bias to a Th2 response. This could be achieved by effecting different cell populations like macrophages, DC, T cells and their regulatory subsets. Other or similar IR factors could activate monocytes and hence other innate cells. So, the balance between different IR factors is crucial for a balanced regulation of different immune responses. We propose that in pre-eclampsia there is a imbalance between different IR factors. Over-activation of innate cells by IR factor(s) and/or a decrease in adaptive immune response (particularly Th1- type) inhibiting IR factor(s) could cause Th1/Th2 imbalance towards the Th1 phenotype, in some ways comparable with changes observed in systemic sepsis. Our results showed that there are also IR factor(s) (IR-3.3) that can stimulate innate immunity and accelerate septic shock, while other IR factor(s) like IR-3.2 inhibit septic shock and the activity of IR-3.3. IR-3.2 factor(s) present in IR-3 fraction in combination with for example hCG modulate the adaptive immune response towards Th2-type (International Patent Appln. WO99-596 17; inhibition of IFN-gamma by IR-3 (IR-P3) in combination with hCG) and is essential for normal pregnancy and inhibition of Th1 autoimmune diseases, induction of tolerance, etc.

Analysis of hCG preparation (PREGNYL®) and pregnancy urine have shown that hCG preparation and pregnancy urine having anti-shock activity contain IR-3.2 and IR-3.3 fractions in about an 1:2 ratio or higher, while hCG preparations without anti-shock activity or that worse septic shock have an IR-3.2 and IR-3.3 ratio of 1:3 or lower. This also explains why not all commercial hCG preparations have anti-shock activity. Moreover, we showed that hCG preparation possessing a high ratio of IR-3.3 :IR-3.2 and so having no anti-shock activity, mixed with an active hCG preparation could gain anti-shock activity. Thus, the ratio between different IR factors or fractions like IR-3.2 and IR-3.3 can be used as a diagnostic marker not only for the prediction of successful pregnancy, but also for different immunopathology such as pre-eclampsia, sepsis or septic shock etc. In addition, in abnormal pregnancy like pre-eclampsia, one can also use IR factor(s) or IR-fraction(s) (e.g., IR-3.2) as a treatment. The experiments also showed that IR (IR-3.2) inhibited septic shock even 30 hours after shock induction, this shows that IR not only inhibits early mediators of endotoxin lethality like TNF-alpha, IL-1b, MIF, but also inhibits late mediators such as recently characterized high mobility group-1 (HMG-1) protein (*Science* 285: 248–251).

hCG is a member of the structural superfamily of cysteine knot growth factors like NGF, PDGF-B and TGF-beta and a members of the glycoprotein hormone family which also includes LH, FSH and TSH. They each consist of two non-covalently associated protein subunits, a common 15 kd alpha chain and a hormone specific 23 kd beta chain (*Ann. Rev. Biochem.*, 50:465–495). hCG is produced by placental trophoblasts of normal pregnancy, and in gestational trophoblastic disease. It is also produced in much smaller quantities by the pituitary (*Endocrinology*, 137:1402–1411) in both pre- and postmenopausal women and in men (*Trends in Endocrinology and Metabolism*, 1:418–421), in many non-gestational malignant tumors and other tissues. hCG possesses a complex structure as a family of isoforms with structural, immunological and biological differences. The chemical basis for this heterogeneity is not known with certainty but differences in the amino acid composition, carbohydrate residues or both have been proposed. More recently it was also shown that oxidation of specific methionine residues may also be responsible. Different forms of hCG, alpha and beta-subunits, their nicked fragments, beta-core fragment and multiple isoforms of hCG have been reported in different tissues and body fluids (*Journal of Endocrinology*, 161:99–106; *Endocrinology*, 129:1541–1550; *Obstet. Gynecol*, 77:53–59; *Journal of Biochemistry*, 107, 858–862; *Obstet. Gynecol.*, 80:223–228; *Endocrinology*, 133:985–989 (1993); *Endocrinology*, 129:1551–1558; *Endocrinology*, 130:2052–2058; *Journal of Endocrinology*, 135:175–188; *Endocrinology*, 139, 519–532; *Molecular and Cellular Endocrinology*, 125:93–131).

Since all commercial hCG preparations are derived from pregnancy urine and contain different breakdown products of hCG, it is assumed these also products have IR activity. The most known breakdown products of hCG are beta-core hCG, a peptide bond nick in the beta-subunit between residues 44–45, 46–47 and 47–48. B48 (IR-K) is found in approximately 10–20% of the molecules in pregnancy urine and is associated with a natural urinary metabolite of hCG. Our experiments showed that IR-K accelerates septic shock (like MIF) and LPS induced proliferation of splenocytes alone or in combination with a non-active hCG preparation. This effect is inhabitable with anti-MIF, active hCG preparation, IR-3.2 and denatured b48 (IR-Kb) peptide. This shows that IR-K activity resembles with IR-3.3 and the IR-Kb activity resembles to IR-3.2. In addition, there are also other peptide bond cleavages in hCG and its subunits as well as heterogeneity of the beta-core fragment. For example, b45 bond cleavage, mainly found in hCG preparation and in urine, possibly derive from the action of bacterial proteases. In addition, Medeiros et al. Showed that HPLC separation of beta-core in its reduced and S-carboxymethylated forms showed three peptides, but only two of them could be sequenced and was demonstrated to be the previously reported b6–40 and b55–92 peptides of bhCG, while the third peak did not give any clear sequence because of the low signal due to several unidentified amino acids. It was illustrated that breakdown products of IR-K share activity with IR-3.2. This IR-K peptide lies between two beta-core fragments (b6–40 and b55–92) and partially derived from beta-core b55–92 fragment. It is possible that there are also other single and/or double cleavage products of beta-core fragments or of not yet identified beta-core peptides (like Medeiros et al., showed beta-core faction with unidentified amino acids) responsible for IR activity in hCG preparations and pregnancy urine. Breakdown products of b48-peptide with additional unidentified amino acids from beta-core and/or with additional glycosylation possess among other anti-diabetic and anti-chronic inflammatory activity.

In short, the invention provides among other things an immunoregulator (IR) obtainable or derivable from a urinary metabolite of hCG, in particular from (nicked) forms of beta-hCG chains or breakdown products thereof, or (synthetic) peptide homologues or analogues thereof. These forms of beta-hCG have peptide bond cleavages within the beta-subunit (Birken et al, *Endocrinology* 133:1390–1397 (1993)), and herein it is provided that the breakdown products, especially those from the β44 to β49 regions provide significant immunoregulatory effects, for example demonstrated by using the animal model test systems as provided.

It was found for example herein in animal experiments as described below that peptides obtainable from hCG react in a septic shock model with strong immunoregulatory effects.

Table 1: Immunoregulatory peptides and their effects on septic shock.

TABLE 1

Immunoregulatory peptides and their effects on septic shock.

| Peptides | EFFECTS ON SHOCK | |
|---|---|---|
| | Decreases | Enhances |
| Peptides with essentially balancing effects | | |
| VLPALPQVVC (SEQ ID NO 3) | ** | * |
| MTR | * | * |

TABLE 1-continued

Immunoregulatory peptides and their effects on septic shock.
EFFECTS ON SHOCK

| Peptides | Decreases | Enhances |
|---|---|---|
| LQGVLPALPQVVC (SEQ ID NO 2) | ** | ** |
| (CYCLIC) LQGVLPALPQVVC (SEQ ID NO 2) | ** | ** |
| GVLPALPQ (SEQ ID NO 10) | * | * |
| LQGVLPALPQ (SEQ ID NO 4) | * | ** |
| Peptides with essentially shock decreasing effects | | |
| LQGV (SEQ ID NO 8) | ** | |
| VLPALP (SEQ ID NO 12) | ** | |
| GVLPALP (SEQ ID NO 11) | * | |
| VVC | * | |
| MTRV (SEQ ID NO 5) | * | |
| Peptides with essentially shock enhancing effects | | |
| LQG | | ** |
| VLPALPQ (SEQ ID NO 9) | | ** |

Table 2 shows the survival percentages of mice over 72 hours. These data are representative of at least 10 different experiments. For the endotoxin model, BALB/c mice were injected intraperitoneally with 8–9 mg/kg LPS (*E. coli* 026:B6; Difco Lab., Detroit, Mich., US). Control groups (PBS) were treated with PBS intraperitoneally only. We treated BALB/c with a dose of 300–700 IU of different hCG preparations (PG23; PREGNYL® batch no. 235863, PG25; PREGNYL® batch no. 255957) or with peptides (5 mg/kg) after 2 h of LPS injection.

In these experiments, it is shown that peptides 4 and 6 inhibited shock completely, while peptide 2, 3 and 7 accelerated shock. In addition, 1, 5, 8, 9 11, 12, 13 and 14 showed in number of different experiments variability in effectiveness as well as in the kind (inhibitory vs accelerating) of activity.

and promote the IL-10 and TGF-beta production, in contrast to IL-4 production, which indicates the induction of regulatory cells like Th3 and Th1 by IR. These regulatory cells may play a role in the therapeutic effects of IR in immune and inflammatory diseases and immune tolerance. We have also shown that IR and its fractions are able to inhibit the production of IFN-gamma in vitro and in vivo except for the fraction IR-P3 and rhCG that separately show no to moderate inhibition of the IFN-gamma production. The combination of IR-P3 and rhCG gives a stronger inhibition of the IFN-gamma. This implies the need of IR-P3 for rhCG for its at least its IFN-gamma inhibition in these models. This implies also to the anti-CD3 stimulated spleen cells obtained from in vivo treated NOD mice and also to polarization of T-helper cells to Th2 phenotype.

Moreover, IR-P, its fractions (IR-P1, IR-P2, IR-P3) and IR-P3 in combination with rhCG are all able to inhibit the class switch of B-cells to IgG2a, while IR-P2 and rhCG give nothing to moderate inhibition. Our results on IFN-gamma production and proliferation showed that IR-P3 alone +did not have the maximum effect as compared to IR-P, whereas, for IgG2a inhibition, we see that IR-P3 does not need rhCG to give the maximum results. However, the increase in production of IL-10 under the influence of IR-P3 is less than for IR-P1. This suggests that for maximum production of IL-10, hCG, a breakdown product thereof, or a yet unknown sub-fraction of IR-P1 in combination with IR-P3, is needed. Because IR-P3 alone is already able to promote IL-10 production, it does not need any other fraction or component to inhibit the production of IgG2a.

Also shown is that IR as provided by the invention is able to inhibit the IFN-gamma production and the promotion of IL-10, TGF-beta, IL-4 and IL-6 in the BALB/c animal model (in vitro as well as ex vivo). So it is clear that at least these cytokines are involved in the regulation of immune responses by IR and in the induction of regulatory cells. Remarkably, IR promotes the proliferation of anti-CD3

TABLE 2

| | | % SURVIVAL TIME (HRS) | | | |
|---|---|---|---|---|---|
| Test substance | | 0 | 16 | 40 | 72 |
| PBS | | 100 | 100 | 67 | 17 |
| PG23 | | 100 | 100 | 100 | 100 |
| PG25 | | 100 | 83 | 83 | 83 |
| PEPTIDE NO. | SEQUENCE | | | | |
| 1 | VLPALPQVVC (SEQ ID NO 3) | 100 | 100 | 50 | 17 |
| 2 | LQGVLPALPQ (SEQ ID NO 4) | 100 | 67 | 0 | 0 |
| 3 | LQG | 100 | 83 | 20 | 17 |
| 4 | LQGV (SEQ ID NO 8) | 100 | 100 | 100 | 100 |
| 5 | GVLPALPQ (SEQ ID NO 10) | 100 | 100 | 80 | 17 |
| 6 | VLPALP (SEQ ID NO 12) | 100 | 100 | 100 | 100 |
| 7 | VLPALPQ (SEQ ID NO 9) | 100 | 83 | 0 | 0 |
| 8 | GVLPALP (SEQ ID NO 11) | 100 | 100 | 83 | 67 |
| 9 | VVC | 100 | 100 | 50 | 50 |
| 11 | MTRV (SEQ ID NO 5) | 100 | 100 | 67 | 50 |
| 12 | MTR | 100 | 100 | 67 | 50 |
| 13 | LQGVLPALPQVVC (SEQ ID NO 2) | 100 | 100 | 100 | 100 |
| 14 | (Cyclic) LQGVLPALPQVVC (SEQ ID NO 2) | 100 | 83 | 83 | 83 |

Not intending to be bound by one theory of the invention, the results also show that IR as provided by the invention is able to regulate the Th1/Th2 balance in vivo (BALB/c, NOD) and in vitro. In dominant Th1 phenotype models like NOD, IR (like IR-P and its fractions, amongst others, down-regulates the IFN-gamma production (in vivo/in vitro)

stimulated spleen cells (ex vivo) in BALB/c mice in contrast to NOD. This might reflect the difference in NOD which is an auto-immune disease model and BALB/c which is an animal model without distinct immunopathology. In both animal models (NOD/BALB/c) IR promotes LPS stimulated proliferation of spleens (in vitro and ex vivo).

Our DC experiments with NOD and BALB/c mice show that IR does not just regulate T-cell responses, but can also regulate DC maturation and function. DC that functions as professional antigen processing cells (APC) can play an important role in immune tolerance. Treatment of C57B/6 DC with IR in allo-MLR is able to down-regulate T-cell proliferation. This shows that IR can also facilitate the induction of a state of tolerance. On the basis of these data we performed MHC and non-MHC incompatible skin (C57BL/6) transplantation to recipients (BALB/c) treated with IR. The data showed that in the control group the allograft (skin) was completely rejected within 15 days, while the skin graft of recipient mice treated with IR three times was rejected after 21 days. Accordingly, IR is able to delay graft rejection. IR, as provided by the invention, is able to inhibit the immunopathology in numerous animal models for immune diseases. IR inhibits the immunopathology and clinical symptoms in the NOD model (for diabetes), and the EAE model (for MS), inhibits allograft rejection, and delays SZT-induced diabetes. Our data also shows that IR has effects on different cell populations. IR affects T-cells and thereby regulates Th1/Th2 balance and induce regulatory cells that in turn not only just regulate T-cells but also have effects on the APC compartment. In addition, IR can regulate the APC compartment directly and can influence the innate and adaptive immune responses. By doing so, IR not only can influence diseases caused by imbalance of the adaptive immune system, but can also influence the diseases due to the imbalance of the innate immune system or of both systems. For example, the role of cytokines and the innate immune system in the etiology of Type II diabetes is likely important. Recently it is has been suggested that unknown factors, like age and over nutrition, in genetically or otherwise predisposed subjects, cause increased secretion of cytokines from cells such as macrophages and further cytokine secretion from atherosclerotic plaques. The acute-phase response induced by cytokines includes a characteristic dyslipdaemia (raised VLDL triglyceride and lowered HDL cholesterol) and other risk factors for atherosclerosis, such as fibrinogen. Cytokines also act on the pancreatic beta cell (contributing to impaired insulin secretion), on adipose tissue (stimulating leptin release) and on the brain, stimulating corticotropin-releasing hormone, ACTH and thus cortisol secretion. The latter may contribute to central obesity, hypertension and insulin resistance. A further cause of insulin resistance is the cytokine TNF-alpha, which inhibits the tyrosine kinase activity of the insulin receptor. Type II diabetic patients without microvascular or macrovascular complications have a high acute-phase response but tissue complications further increase stress reactants in Type II diabetes. In non-diabetic subjects with atherosclerosis, a "hematological stress syndrome" has been recognized for many years, consisting of high acute-phase reactants such as fibrinogen, increased blood viscosity and increased platelet number and activity. Cytokines produced by endothelium, smooth muscle cells and macrophages of the atherosclerotic plaque could contribute to this acute-phase response seen in atherosclerosis. Apart from the acute-phase proteins which are established or putative risk factors for cardiovascular disease such as fibrinogen, serum amyloid A, PAI-1, Lp(a) lipoprotein and VLDL triglyceride, pro-inflammatory cytokines produced at the sites of diabetic complications or by the diabetic process itself may also exacerbate atherosclerosis by acting on the endothelium, smooth muscle cells and macrophages. Thus, there is likely positive feedback involving cytokines and atherosclerosis, perhaps accounting for the acceleration of arterial disease in diabetes. The plaque produces cytokines, which further exacerbate the process of atherosclerosis locally but also cause an increase in circulating acute-phase proteins, many of which are themselves risk factors for atherosclerosis.

In summary, cytokines and the innate immune system play a central role in the pathophysiology of Type II diabetes and atherosclerosis. Since IR has the ability to regulate such a response, it is also beneficial to type II diabetes and atherosclerosis and its complications. In addition, IR can delay the induction of disease such as diabetes in the HD-STZ model where reactive oxygen species (ROS) play an important role, so IR can also act as an anti-oxidant directly or indirectly. Also for that reason, it is beneficial in the treatment and prevention of diabetes and related diseases. Furthermore, the invention provides an immunoregulator selected by a method according to the invention, a pharmaceutical composition comprising such a selected immunoregulator, and the use of it for the preparation of a pharmaceutical composition for the treatment of an immune-mediated disorder.

Fractions containing bioactive IR are purified to homogeneity by liquid chromatography. The direct analysis by mass spectrometry combined with database screening, using MALDI-TOF (matrix assisted laser mass desorption/ionization-time of flight), permits the characterization of IR or fractions thereof in multimolecular complexes. Nuclear magnetic resonance spectroscopy provides information on the types of bonding to the hydrogen atoms in the IR and the molecular structure of the IR. Infrared and near-ultraviolet spectroscopy aids in structural determination of the IR. MALDI-TOF and NMR analysis complements separation, if needed, and subsequent sequencing and synthesis of the bioactive IR. Chemical mutagenesis is employed to mutate the chemical composition of IR, permitting fine mapping of the interaction site with the receptor/acceptor by performing qualitative and quantitative binding analysis in appropriate detection systems like a biosensor system.

Derivatives of IR by chemical and genetic modification are again tested for bioactivity in the above methods or assays demonstrating activity of IR or IR containing mixtures. Furthermore, the present invention provides verification of the presence of a receptor of IR. Various fractions of pregnancy urine, commercial hCG preparations or fragments thereof, and recombinant hCG or fragments thereof are spiked with known amounts of IR. The mixtures are analyzed by gel permeation chromatography and compared to the mentioned samples without spiked IR and free IR. Shifts in IR peak(s) to higher molecular weight fractions indicates the presence of a receptor/acceptor. Analyzing the fractions for IR activity (after IR has been displaced from the receptor/acceptor) validates this elution profile containing the shifted IR peaks. From the fraction containing the shifted IR activity, the receptor/acceptor is purified by liquid chromatography and validated for IR function by displacement. The IR is, in addition, iodinated and spiked to fractions of first trimester pregnancy urine, commercial hCG preparations or fragments thereof, and recombinant hCG or fragments thereof and the mixtures are evaluated in appropriate detection systems like SDS-PAGE (sodium dodecyl sulfate-polyacrylamide gel electrophoresis) under reducing and nonreducing conditions. Blots of such gels are analyzed by systems like quantitative phosphorimaging analysis using STORM technology. IR is immobilized, to e.g., Affigel by the use of a chemical linker or carrier protein permitting the isolation of binding moieties by means of affinity chromatography. Subsequent elution provides purified receptor/acceptor molecules. The receptor/acceptor isolated from extracellular and intracellular sources in soluble or in membrane-bound form are immobilized to an activated biosensor surface. The IR in various concentrations will then probe this sensor surface and from the resulting binding profiles, the association rate and dissociation rate constants are determined and the affinity constant is calculated. By probing with different mixtures of IR and receptors/acceptors, epitope mapping is evaluated to obtain information on the nature of binding epitope. IR is labeled (e.g., fluorescent and radioactively) to permit detection of IR receptors in membrane-bound form to assess cellular expression and tissue distribution under nondiseased states and during the various immune and related disorders pertinent to the activity of IR. Using labeled IR and having available purified receptor, monoclonal antibodies and other specific reagents are generated allowing the design of a quantitative immuno-assay for the measurement of soluble IR receptors. Recombinant DNA technology is used to generate IR producing prokaryotic and eukaryotic expression systems. Site-directed mutagenesis is used to produce IR variants with altered binding profiles permitting the fine identification of the interaction site with the receptor/acceptor. Upon the cloning of the gene, transgenic mice with constitutive and inducible expression of the IR, as well as IR gene-deficient mice, are generated permitting the entry into the field of biotechnology and gene therapy.

Purified IR is used to produce monoclonal antibodies and/or other specific reagents, thereby facilitating the design of an IR-specific quantitative immuno-assay. Also, single chain $F_v$ fragments are isolated by using the phage display technology with the use of a phage library containing a repertoire comprising a vast number of different specificities.

Immunoregulator (IR): IR-U Purification from First Trimester Pregnancy Urine

Method 1: First trimester pregnancy urine (2 liters) was collected in a bottle from a healthy volunteer and was refrigerated until delivered at the laboratory within 2 days. Upon delivery, 1 gram per liter of sodium azide was added and the pH was adjusted to 7.2–7.4 with sodium hydroxide and allowed to sediment for 1 hour (h) at room temperature (RT). Approximately, 75% of the supernatant was decanted and the remainder close to the precipitate was centrifuged (10 min at 25000 rpm at 40C) to remove sediment and added to the rest of the supernatants. The supernatants were filtered through 0.45 (m in a Minitan) (Millipore) transversal filtration set-up. Subsequently, the filtrate (2 liter) was concentrated in an Amicon ultrafiltration set-up equipped with a YM Diopore membrane with a 10 kDa cut-off. The final volume (250 ml) was dialyzed against 2 changes of 10 liters of Milli Q water. Next, the sample was further concentrated by 10 kDa cut-off in an Amicon ultrafiltration to a final volume of 3 ml.

Gel permeation: A Pharmacia FPLC system equipped with a Superdex 75 gel permeation column was used to analyze the treated urine sample (IR-U) and commercial hCG preparation (IR-P) (PREGNYL). The running conditions are shown elsewhere in this document:

IR-U Purification from First Trimester Pregnancy Urine

Method 2: In order to purify lower molecular weight fractions from first trimester pregnancy urine, 50 ml of urine was directly desalted with an FPLC system equipped with an FDC®G25 in 50 mM ammonium bicarbonate. The running conditions used are shown below:

| | | |
|---|---|---|
| 0.0 | CONC % B | 0.0 |
| 0.0 | ML/MIN | 0.50 |
| 0.1 | ML/MIN | 1.00 |
| 0.2 | ML/MIN | 2.00 |
| 0.3 | ML/MIN | 3.00 |
| 0.4 | ML/MIN | 4.00 |
| 0.5 | ML/MIN | 5.00 |
| 0.5 | CM/MIN | 1.00 |
| 1.5 | VALVE.POS | 1.2 |
| 1.5 | CLEAR DATA | |
| 1.5 | MONITOR | 1 |
| 1.5 | LEVEL % | 2.0 |
| 1.5 | MIN/MARK | 2.0 |
| 1.5 | INTEGRATE | 1 |
| 1.8 | VALVE.POS | 1.1 |
| 2.3 | PORT.SET | 6.1 |
| 6.6 | FEED TUBE | |
| 10.8 | PORT.SET | 6.0 |
| 10.8 | INTEGRATE | 0 |
| 10.8 | FEED TUBE | |
| 12.8 | CONC % B | 0.0 |

IR-U Purification from First Trimester Pregnancy Urine

Method 3: To analyze the IR-U (first trimester urine) obtained from method 1 and 2, we also used a Shimadzu HPLC system equipped with Alltech macrosphere size exclusion (GPC) column 60 Å or 300 Å (250×4.6 mm) in 50 mM ammonium bicarbonate. The separation range for both columns was 28,000–250 and 1,200,000–7,500 Dalton, respectively. Sample load volume was 10–50 ml. The flow rate was 0.3 ml/min for 25 minutes. External molecular weight standards were also employed to calibrate the column elution positions. The markers used were: aprotinin (6,500 Da), cytochrome C (12,400), carbonic anhydrase (29,000), albumin (66,000) and blue dextran (2,000,000).

To analyze IR further, two different hCG preparations, IR-P (PREGNYL) and IR-A (APL; Weyth Ayerst; Philadelphia, USA), were used. IR-P was further separated by two methods. A Pharmacia FPLC system equipped with a Superdex 75 gel permeation column (HR 5/30) (Pharmacia, Sweden) was used to analyze the IR-P. For the running buffer 50 mM ammonium bicarbonate was used. The separation range of this column was 100,000–3,000 Da for globular proteins. Sample load volume was 1 ml and the flow rate was 0.5 ml/min for 45 min. In addition, Macrosphere GPC 60 Å (250×4.6 mm) was also used. This column separates proteins, peptides, and other water-soluble macromolecules by size exclusion chromatography. The separation range of this column was 28,000–250 Dalton. Three selected areas were fractionated, IR-P1 which elutes apparently with molecular weight of >10 kDa, IR-P2 which elutes apparently with molecular weight between the 10 kDa-1 kDa, and IR-P3 which elutes apparently with molecular weight <1 kDa.

Purification of IR from Lower Molecular Fraction First Trimester Pregnancy Urine (IR-U/LMDF) and Commercial hCG Preparations (PREGNYL, APL):

Method 4: Procedure: The lyophilized low molecular mass fraction (<2 KDa) obtained from first trimester pregnancy urine and from commercial hCG preparations (PREGNYL, APL) by method 3 were further analyzed by gel filtration chromatography on a Bio-Gel P-2 column (96×1.5 cm). Fraction (13–17 mg) was suspended in bi-distilled water (8–12 ml). The material was not completely dissolved. The sediment (8–11 mg) was separated from the supernatant by centrifugation (Sigma 201, 10 min, 3000 rpm). The supernatant (6–8 ml) was fractionated by gel filtration chromatography on a Bio-Gel P-2 column. The column was eluted with water at a flow rate of 15 ml/min. The elution was monitored with an LKB 2142 differential refractometer and an LKB 2238 Uvicord SII (206 nm). Fractions (20 min) were collected by a Pharmacia Frac 100 fraction collector. Definite fractions were pooled and lyophilized. These fractions were further tested for anti-shock activity.

Gel permeation: A Pharmacia FPLC system equipped with a Superdex 75 gel permeation column was used to analyze the treated urine sample (IR-U) and commercial hCG preparation (IR-P) (PREGNYL). The running conditions used are shown below:

| 0.0 | CONC % B | 0.0 |
|---|---|---|
| 0.0 | ML/MIN | 0.20 |
| 0.5 | ML/MIN | 0.50 |
| 0.5 | CM/ML | 0.50 |
| 0.8 | ML/MIN | 1.00 |
| 0.8 | CM/ML | 1.00 |
| 2.0 | CLEAR DATA | |
| | HOLD | |
| 2.0 | VALVE.POS | 1.2 |
| 2.0 | MONITOR | 1 |
| 2.0 | LEVEL % | 5.0 |
| 2.0 | ML/MARK | 2.0 |
| 2.0 | INTEGRATE | 1 |
| 4.0 | VALVE.POS | 1.1 |
| 6.0 | PORT.SET | 6.1 |
| 50.0 | INTEGRATE | 0 |
| 52.0 | CONC % B | 0.0 |

Anion exchange chromatography: In order to further separate the overlapping fractions, 1 ml MONO Q HR 5/5 FPLC anion exchange column was used. The running conditions are shown below and the buffer combination consisted of 10 mM PBS, pH 7.3 as buffer A and PBS containing 1 M NaCl as buffer B:

| 0.0 | CONC % B | 0.0 |
|---|---|---|
| 0.0 | ML/MIN | 1.00 |
| 0.0 | CM/ML | 1.00 |
| 1.0 | ALARM | 0.1 |
| 1.0 | HOLD | |
| 1.0 | CLEAR DATA | |
| 1.0 | MONITOR | 1 |
| 1.0 | LEVEL % | 5.0 |
| 1.0 | ML/MARK | 2.0 |
| 1.0 | INTEGRATE | 1 |
| 1.0 | PORT.SET | 6.0 |
| 1.0 | VALVE.POS | 1.2 |
| 6.0 | CONC % B | 0.0 |
| 6.0 | PORT.SET | 6.0 |
| 11.0 | CONC % B | 50.0 |
| 14.0 | CONC % B | 50.0 |
| 16.0 | CONC % B | 100 |
| 16.0 | PORT.SET | 6.0 |
| 18.0 | CONC % B | 100 |
| 18.0 | CONC % B | 0.0 |
| 18.0 | INTEGRATE | 0 |
| 25.0 | CONC % B | 0.0 |

Further treatment of the IR-U and IR-P: To reduce covalent binding between protein species present in the urine sample, we treated the urine (IR-U) and hCG preparation (IR-P) sample with 60 mM 2-mercaptoethanol for 3 min at 100° C. Subsequently, the treated IR-U and IR-P sample were applied to the Superdex 75 column under identical running conditions.

Activity Determination of FPLC Fractions of IR-U: The protein concentration of urine fractions was determined by OD280 nm divided by 1.4. From this value, the amount of hCG units was calculated using 5000 IU/ml PREGNYL preparation of hCG corresponded to 100 µg.

Alternative methods for purifying and/or isolating IR comprise gel filtration on, for example, a Superdex 75 column in an FPLC system using PBS with or without ethanol to increase resolution and disrupt hydrophobic interactions, optionally followed by cationic exchange. Samples can be submitted in reduced or unreduced form. Another method comprises lectin affinity chromatography to better separate carbohydrate containing components from other components, whereby the effluent is further subjected to gel filtration. It is, of course, possible to derive at synthetic or recombinant (poly) peptide sequences with methods known in the art, and to select (synthetic) antibodies, i.e., phage-derived, to further select IR.

Auto-Immune Disease Experiments

The non-obese diabetic (NOD) mouse is a model for auto-immune disease, in this case insulin-dependent diabetes mellitus (IDDM), which main clinical feature is elevated blood glucose levels (hyperglycemia). The elevated blood glucose levels are caused by the immune-mediated destruction of insulin-producing β cells in the islets of Langerhans of the pancreas (Bach et al. 1991, Atkinson et al. 1994). This destruction is accompanied by a massive cellular infiltration surrounding and penetrating the islets (insulitis) by a heterogeneous mixture composed of a CD4+ and CD8+ T-lymphocytes, B-lymphocytes, macrophages and dendritic cells (O'Reilly et al. 1991). The easiest and most reliable way to detect the onset of diabetes in these mice is to test for glucose levels in the blood.

The NOD mouse represents a model in which auto-immunity against beta-cells is the primary event in the development of IDDM. In general, T-lymphocytes play a pivotal role in initiating the disease process (Sempe et al. 1991, Miyazaki et al. 1985, Harada et al. 1986, Makino et al. 1986). Diabetogenesis is mediated through a multifactorial interaction between a unique MHC class II gene and multiple, unlinked, genetic loci as in the human disease. Moreover, the NOD mouse demonstrates beautifully the critical interaction between heredity and environment. Differences between the cleanliness of the housing conditions illustrates how environmental factors can affect the action of diabetes-mediated genes (Elias et al. 1994).

As for the auto-immunity recorded in NOD mice, most antigen-specific antibodies and T-cell responses have been studied after these antigens were detected as self-antigens in diabetic patients. Understanding the role that these auto-antigens play in NOD diabetes may allow to distinguish between primary pathogenic auto-antigens and auto-immunity that is an epiphenomenon. Moreover, one should bear in mind that IDDM patients are genetically and pathogenically heterogeneous.

A typical longitudinal histological examination of the NOD pancreas demonstrates infiltrating cells surrounding the blood vessels at 3–4 weeks of age, but the islets are typically still clear at 6–7 weeks. Infiltrating cells than reach the islets, either surrounding them or accumulating at one pole. Between 10 and 12 weeks, the infiltrating cells penetrate into the islets and the islets become swollen with lymphocytes. As mentioned above, differences between the housing conditions and microbiological and environmental factors can affect the penetrance of diabetes-susceptible genes.

In the study, typically between 14 and 17 weeks, NOD mice become diabetic. However, this varies from lab to lab (average 14–19 weeks) (Elias et al. 1994). CD4+ T-cells can be separated into at least two major subsets Th1 and Th2.

Activated Th1 cells secrete IFN-γ and TNF-α, while Th2 cells produce IL-4, IL-5 and IL-10. Th1 cells are critically involved in the generation of effective cellular immunity, whereas Th2 cells are instrumental in the generation of humoral and mucosal immunity and allergy, including the activation of eosinophils and mast cells and the production of IgE (Abbas et al. 1996). A number of studies have now correlated diabetes in mice and humans with Th1 phenotype development (Liblau et al. 1995, Katz et al. 1995).

Th2 T-cells are shown to be relatively innocuous. Some have even speculated that Th2 T-cells, in fact, may be protective. But Katz et al. have shown the ability of CD4+ T-cells to transfer diabetes to naive recipients resided not with the antigen specificity recognized by the TCR, per se, but with the phenotypic nature of the T-cell response. Strongly polarized Th1 T-cells transferred disease into NOD neonatal mice, while Th2 T-cells did not, despite being activated and bearing the same TCR as the diabetogenic Th1 T-cell population. Moreover, upon co-transfer, Th2 T-cells could not ameliorate Th1-induced diabetes, even when Th2 cells were co-transferred in 10-fold excess (Pakala et al. 1997).

Th1-polarized T-cells can transfer disease in neonatal NOD mice, something Th2-polarized T-cells fail to do. Both Th1- and Th2-polarized T-cells can transfer disease in NOD-.scidmice and other immune-compromised recipients. Th2-mediated diabetes in NOD.scid recipients exhibited a longer pre-diabetic phase and a lowered overall-incidence. Moreover, the diabetic lesion created by Th2 cells is unique and quite unlike the lesion found in spontaneously diabetic or Th1 T-cell-induced diabetes in either neonates or NOD-.scid mice (Pakala et al. 1997).

In addition, IFN-γ correlates with diabetes (in NOD as well as in humans) and anti-IFN-γ prevents disease; under disease, IFN-γ+ cells are present in islets and antigen-specific Th1 clones accelerate the onset of diabetes (Pakala et al. 1997, O'Garra et al. 1997). Furthermore, Th2 cells only induce insulitis in neonatal NOD, but have the capacity to induce diabetes in immuno-compromised NOD.scid; also, disease is inhibitable by anti-IL-10, but not by anti-IL-4 (Pakala et al. 1997). This suggests that non-Th2 type regulator T-cells are present in normal mice, but these are absent in immunodeficient mice. These results stress the existence of cells regulating the balance between activated Th-sub-populations. Possible disturbances in this balance induced by altered reactivity of such regulatory T-cell populations can cause immune-mediated diseases, which results in absence or over-production of certain critically important cytokines (O'Garra et al. 1997).

Some auto-immune diseases, in particular Th1 mediated diseases, like rheumatoid arthritis (RA) (Grossman et al. 1997, Russel et al. 1997, Buyon et al. 1998, Hintzen et al. 1997) can remit during pregnancy. Furthermore, successful pregnancy is a Th2 type phenomenon (Raghupath et al. 1997). We tested hCG preparation and its fractions from PREGNYL on the development of diabetes in NOD mice and in an in vitro model.

Surprisingly, we found that intraperitoneal treatment of NOD mice of age 15 weeks, with an hCG preparation for three times a week for a month can delay or inhibit the onset of diabetes. In addition, transfer of total spleen cells from these treated NOD mice into NOD.scid mice can delay or prevent diabetes in NOD.scid whereas transfer of nontreated spleen cells cannot. This anti-diabetic effect resides in a fraction obtainable from a pregnant woman but not in hCG.

Mice. NOD mice were bred in our facilities under specific pathogen-free conditions. The spontaneous incidence of diabetes in our colony is 85% in females at 15 weeks of age. NOD.scid mice were also bred in our facilities under specific pathogen-free conditions. Transfer of diabetogenic cells from NOD to NOD.scid at the age of 8 weeks induces diabetes after 22 days.

Diabetes. Diabetes was assessed by measurement of venous blood using an Abbott Medisense Precision Q.I.D. glucometer and also monitored for glucosuria (Gluketur Test; Boehringer Mannheim, Mannheim, Germany). Animals were considered diabetic after two consecutive glucose measurements of higher than 13.75 mmol/l (250 mg/dl) Onset of diabetes was dated from the first consecutive reading. In instances of sustained hyperglycemia of >33 mmol/l animals were killed to avoid prolonged discomfort.

Immunohistochemistry. Mice were euthanized by $CO_2$ asphyxiation. The entire pancreata were removed and snap frozen in OCT compound (Tissue-tek) for cry-sectioning. 5-μm cryo-sections were obtained, air dried, and stored at −20° C. until used. Formalin-fixed sections were deparaffinised in xylene and alcohol, and stained with hematoxylin and eosin for general morphology. Immunohistochemistry for insulin was then performed using a two-step protocol. Endogenous peroxidase activity was blocked, and slides were incubated with a rabbit antiserum to insulin (Dako Corp., Carpenteria, Calif.; 1:500 in 5% normal mouse serum for 30 min). After washing steps, staining was revealed with horseradish peroxidaseconjugated anti-rabbit Ig (Dako; 1:500 in 5% NMS for 30 min), developed with amino-ethyl-carbazole (AEC; Pierce) for 10 min and mounted in crystal mount.

in vivo anti-diabetic effect: NOD mice at the age of 15 weeks were treated with PBS (n=4), 300 IU PREGNYL (n—4), or 600 IU PREGNYL (n=4) i.p., 3 times a week for four weeks and diabetes was assessed as mentioned above. After four weeks, the treatment was stopped and the PBS and the 600 IU PREGNYL group were killed after one week. The 300 IU PREGNYL group was left alive until the age of 28 weeks. Spleen cell transfer. The spleen was removed from 600 IU PREGNYL treated NOD and PBS control treated NOD mice, and total spleen cells were recovered. These cells were washed twice with PBS and 20×10⁶ cells were i.p. transferred into an 8-wk-old NOD.scid mouse.

Transfer Experiments

Total spleen cells were recovered from 9-wk-old NOD mice and stimulated in vitro in RPMI supplemented with 10% FBS with coated anti-CD3 (145–2C11; 25 mg/ml) and IL-2 (50U/ml) along with 300 IU/ml IR-P, 100 mg/ml IR-U3–5 or IR-U/LMDF. Plates were then incubated at 37° C. in 5% of $CO_2$ in air for 48 hrs. After 48 hrs, cells were twice washed with PBS and 20×10⁶ cells were i.p. transferred into an 8-wk-old NOD.scid mouse.

In vitro restimulation. Total spleen cells (1×10⁶ cells/ml) from 20-wk-old NOD were stimulated in RPMI+ supplemented with 10% FBS with LPS (E. coli; 10 μg/ml) or coated anti-CD3 (145–2c11;25 μg/ml) with different doses of hCG-PREGNYL (50, 100, 300, 600, 800 IU/ml), Fraction 1–2 (200) μg/ml), Fraction 3–5 (200(g/ml), human recombinant hCG, α-hCG, and β-hCG (each at 200 μg/ml) in flat bottom 96-well plates. Wells with anti-CD3 coating were implemented with IL-2 (40 IU/ml). Plates were incubated at 37° C. in 5% CO2 in air for 48 hrs. After 48 hrs of incubation the supernatants were collected for cytokine analyzes.

CD4+ T-cells were isolated from total spleen cells of 20-wk-old NOD and stimulated as mentioned above with anti-CD3 at different conditions. These wells were implemented with IL-2 (40 μg/ml) and anti-CD28 (10 μg/ml). After 48 hrs of incubation the supernatants were also collected for cytokine analyzes.

To determine the effect of IR on the potential of CD4 cells to differentiate into Th1 or Th2 cytokine-producing effector cells, Th polarization assay was performed in the presence or absence of IR. Total spleen cells from 8-wk-old female NOD were used as a source to purify CD4+ cells. Purified CD4+ T-cells from the spleen were obtained by negative selection due to complement depletion with antibodies specific for B-cells, NK-cells, monocytes/macrophages and granulocytes. Cells were further purified using magnetic activated cell sorting with a cocktail of biotinylated mAbs against CD 11b, B220, CD8 and CD40, followed by incubation with streptavidin conjugated microbeads (Milteny Biotech, Bergisch Gladbach, DE). CD4+ cells used for experiments were always 90–95% purified as determined by flow cytometry. For primary stimulation, purified CD4+ T-cells were cultured at $1\times10^5$ cells/well in flat bottom 96-well plates (Nalge Nunc Int., Naperville, Ill., USA), and stimulated with plate-bound anti-CD3 mAb (145–2C11, 25 mg/ml), anti-CD28, and IL-2 (50 U/ml). For differentiation of Th1 cells, anti-IL-4 mAb (11B11; 10 mg/ml) and IL-12 (10 ng/ml) were added to the cultures. Priming for Th2 cells was with IL-4 (35 ng/ml) and antiIFN-g mAb (XMG 1.2; 5 mg/ml). Furthermore, in Th1 and Th2 priming conditions, also 300 IU/ml IR-P and 100 mg/ml IR-U/LMDF in the presence or absence of blocking anti-IL-10 (10 mg/ml), anti-TGF-b (10 mg/ml), and VitD3 (10 mg/ml). Unprimed cultures contained only anti-CD3, anti-CD28 and IL-2. All doses were optimized in preliminary experiments. After 4 days of culture, the cells were washed 3 times and transferred to new anti-CD3-coated 96-well plates and restimulated in the presence of IL-2 (50 U/ml) and anti-CD28 (10 mg/ml). Forty-eight hours later, supernatants were collected and assayed for IL-4, IFN-g and IL-10 production by ELISA as a readout for Th1 versus Th2 polarization.

Ex Vivo NOD Cytokines Experiment:

In rodents, the switch in the production of antibodies from IgM to IgG and other classes appears to be largely under T-cell control mediated by cytokines. Dominant Th1 polarization mediate switching B-cells from IgM production to IgG2a under the influence of massive production of IFN-gamma, while Th2 polarization induces isotype switching in B-cells to IgG1 production. We treated NOD mice at the age of 8–10 weeks with PBS (n=5) or IR-P and its fractions IR-P1, IR-P2, IR-P3, or recombinant hCG (rhCG) and rhCG in combination with IR-P3, each with 200 mg i.p. for three days. Total spleen cells were isolated from all groups and stimulated with LPS or coated anti-CD3 as mentioned before. At different time points, cytokines and proliferation was measured as follows: anti-CD3 stimulated proliferation (t=12, 24, 48 h), anti-CD3 stimulated IFN-gamma (t=24, 30, 48 h), LPS stimulated IgG2a production (t=7 days). In order to determine the effect of IR treatment on Th1 polarization, we isolated CD4+ cells and performed Th1 polarization assays as mentioned before.

BALB/c Experiments:

To separate the immune-modulating activity of IR from its beneficial clinical effects, we treated healthy BALB/c mice i.p. with 300 IU IR-P or 100 mg/ml of IRU/LMDF (n=5). This strain is generally considered to react upon stimulation with a Th2 driven immune response. After four days of treatment with IR, purified CD4+ spleen cells from control and IR-P treated mice were analyzed for Th polarization as mentioned above.

In order to determine the effect of IR-P on cytokine levels produced by splenic APCs, spleen cells from control and IR-P treated BALB/c mice were stimulated in vitro with LPS (E. coli 026:B6; 10 mg/ml, Difco Laboratories, Detroit Mich., US). After 48 hours of incubation, supernatants were collected for cytokine analysis (IL-12p70, IL-6).

IL-10 Knockout Mice Experiment:

To determine the in vivo effect of IR-P in IL-10 gene targeted (IL-10KO) mice, we treated such mice (n=2) i.p. with 300 IU IR-P/day for 4 consecutive days. After 4 days of treatment spleen and lymph nodes cells were recovered and tested for their ability to proliferate in response to LPS and anti-CD3. In addition, CD4+ cells were purified from control and IR-P treated mice and analyzed for Th polarization potential as mentioned above.

NOD Bone Marrow Cell Suspensions:

In order to determine IR-induced effects on dendritic cells (DC) derived from bone marrow (BM), BM of 9-wk-old female NOD mice (n=2) were isolated and incubated with 20 ng/ml GM-CSF ($2.0\times10^5$ cells/ml) for 6 days and at day 7 co-cultured with 300 IU/ml IR-P or 100 mg/ml IR-U (IR-U, IR-U-F3–5 [superdex 75-derived], or IR-U/LMDF [FDC-derived]) for an additional 24 hrs. Briefly, femora and tibiae were cleaned of muscles and tendons and ground in a mortar using DBSS-FCS. Single cell suspensions were obtained by aspiration through a 22 gauge needle into a 2 ml syringe, followed by sieving the cell suspension twice over nylon filters (mesh size 100 and 30 mm respectively; Polymon PES, Kabel, Amsterdam, NL). Furthermore, in order to know whether IR also has an effect on the maturation of DC, BM from NOD mice were also directly co-cultured with GM-CSF and IR for 7 days. At day 8, all cells were analyzed by a flow cytometer for expression of the following markers: CD1d, CD11c, CD14, CD31, CD40, CD43, CD80, CD86, CD95, ER-MP20, ER-MP58, F4/80, E-cad, MHC II, MHC I, RB6 8C5.

A similar experiment was performed with BM cells from a 9-wk-old female BALB/c mice (n=3).

Allo-Mixed Lymphocyte Reaction (MLR):

In order to test the immunosuppressive activity of IR on transplantation rejection, we performed allo-MLR. BM cells from 9-wk-old female BALB/c (n=3) were isolated as mentioned above and treated with (recombinant mouse) rmGM-CSF (20 ng/ml) and IR (IR-P; 300 IU/ml, IR-U; 300 mg/ml, IR-U3–5; 300 mg/ml, IR-U/LMDF; 300 mg/ml) for 7 days. After 7 days, the DC generated were irradiated (2,000 rad) and co-cultured with splenic CD3+ cells isolated from 9-wk-old female C57BL6/Ly. These CD3+ and DC cells were cultured at various ratios and T-cell proliferation was measured via [$^3$H]TdR incorporation (0.5 mCi/well during the last 16 hrs in culture).

Cytokine ELISA. IL-4 was detected using monoclonal anti-IL-4 antibody (11B11) as the capture antibody and revealed with biotinated-conjugated rat anti-mouse IL-4 monoclonal antibody (BVD6 24G2.3). IFN-$\gamma$ was detected using monoclonal anti-IFN-$\gamma$ antibody (XMG1.2) as the capture antibody and revealed with biotinylated conjugated rat anti-mouse IFN-$\gamma$ monoclonal antibody (R46A2). In both cases, ABTS substrate was used for detection.

Flat bottom microplates (96-wells, Falcon 3912, Microtest II Flexible Assay Plate, Becton Dickinson, Oxnard, USA) were coated with cytokine-specific capture antibodies for IL-6, IL-10, IL-4 and IFN-g diluted in PBS (1 mg/ml 20F3 and SXC-1; 5 mg/ml 11B11 and XMG 1.2, respectively) at 4° C. for 18 hrs. After coating, plates were washed (PBS, 0.1% BSA, 0.05% Tween-20) and blocked with PBS supplemented with 1% BSA at room temperature for 1 hr. After washing, samples and standards were added and incubation was continued for at least 4 hrs at room temperature. Thereafter, plates were washed and biotinylated detection antibodies were added (1 mg/ml 32C11

(IL-6) and R46A2 (IFN-g); 0.1 mg/ml 2A5.1 (IL-10) and BVD6.24G2 (IL-4)) and incubated overnight at 4° C. After washing, streptavidin-peroxidase (1/1500 diluted, Jackson Immunoresearch, West Grove, Pa., USA) was added. After 1 hr, plates were washed and the reaction was visualized using 2,2'-azino-bis-3-ethylbenz-thiazoline-6-sulfonic acid (ABTS, 1 mg/ml, Sigma, St. Louis, Mo., US). Optical density was measured at 414 nm, using a Titertek Multiscan (Flow Labs, Redwood City, Calif., US). The amounts of IL-12p70, TNF-a and TGF-b were measured with commercially available ELISA kits (Genzyme Corp, Cambridge, Mass.) according to the protocols provided by the manufacturer.

Sepsis or septic shock experiments. There are three common mouse models used to investigate sepsis or septic shock: high dose LPS, low dose LPS with D-Galactosamine sensitization and low dose superantigen with D-Galactosamine.

One of the first models used for investigating sepsis or septic shock involved treatments with rather large doses of LPS in the inter-peritoneal cavity (between 300–1200 µg). Mice are quite resistant to bacterial toxins, yet succumb to this high dose. It has been suggested that a high dose of LPS in mice might correlate with a lower dose in humans (Mietheke et al.). Approximately 70% of sepsis or septic shocks in humans are caused by Gram-negative bacterial endotoxin and up to 30% are created by exotoxins released from Gram-positive bacteria. The traditional endotoxin, the distinctive lipopolysaccharide (LPS), is associated with the cell membrane of the Gram-negative organism and represents the most common initiator of the sepsis or septic shock pathogenetic cascade. The endotoxin molecule consists or an outer core with a series of oligosaccharides that are antigenically and structurally diverse, an inner oligosaccharide core that has similarities among common gram-negative bacteria, and a core lipid A that is highly conserved across bacterial species. The lipid A is responsible for many of the toxic properties of endotoxin. The systemic effects of endotoxins, such as LPS, seem to be largely mediated by macrophages, since adoptive transfer of endotoxin-sensitive macrophages renders previously endotoxin-resistant mice sensitive to the toxin (Freudenberg et al. 1986).

The more commonly used model of endotoxin sepsis or septic shock takes advantage of the increased susceptibility of BALB/c mice to low doses of LPS after being simultaneously treated with Galactosamine (D-Gal sensitized). This D-Gal treatment dramatically sensitizes animals to the toxic effect of LPS, so that nanogram amounts induce a liver toxicity that is lethal for wild-type animals in a period of 6–7 h. This systemic effect of endotoxin seems to be largely mediated by macrophages. (Gutierrez-Ramos et al. 1997). Although certain mediators are undoubtedly more important than others in producing sepsis, probably dozens of organism- and host-derived mediators interacting, accelerating, and inhibiting one another, are responsible for the pathogenesis of sepsis or septic shock.

On response to LPS, TNF, and other mediators, endothelial cells and macrophages can release a potent vasodilator agent, endothelial-derived relaxing factor (EDRF), which has recently been identified as NO. This molecule causes smooth muscle cell relaxation and potent vasodilatation. Inhibiting NO production with competitive inhibitors of NO synthase results in increased blood pressure in animals with endotoxin shock. This suggests that NO may be partially responsible for the hypotension associated with sepsis. Although inhibition of NO restores blood pressure, such inhibition may reduce tissue blood flow. (Bennett et al.)

Endotoxin can also activate the complement cascade, usually via the alternative pathway. This results in the release of the anaphylotoxins C3a and C5a, which can induce vasodilatation, increase vascular permeability, platelet aggregation, activation and aggregation of neutrophils. These complement-derived mediators may be responsible in part for the microvascular abnormalities associated with sepsis or septic shock. Further, endotoxin can result in the release of bradykinin via the activation of Factor XII (Hageman factor), kallikrein, and kiniogen. Bradyinin is also a potent vasodilator and hypotensive agent. LPS activation of factor XII also leads to intrinsic and (through macrophage and endothelial cell release of tissue factor) extrinsic coagulation pathway activation. This results in consumption of coagulation factors and DIC. TNF also activates the extrinsic pathway and may contribute to these coagulation abnormalities.

Different metabolism of the arachidonic acid cascade are also known to cause vasodilatation (prostacyclins), vasoconstriction (thromboxanes), platelet aggregation, or neutrophil activation. In experimental animals, inhibiting cyclooxygenase or thromboxane synthase has protected against endotoxin shock. Elevated levels of thromboxane B2 (TBX2) and 6-ketoprostaglandin F1 (the end product of prostacylin metabolism) are present in patients with sepsis. A number of cytokines can cause release of these arachidonic acid metabolites from endothelial cells or leukocytes.

In a similar fashion, exotoxin shock model D-Gal sensitized BALB/c mice are treated with low doses of TSST-1 or SEB. These superantigens stimulate the proliferation and activation of a large proportion of T-cells. In fact, the T-cell activation induced by these super-antigens can almost be viewed as a polyclonal T-cell activation in that T-cells expressing a specific Vbeta family are all activated through nonantigen-specific binding of the TCR/MHCII/and a superantigen.

D-Galactosamine has been shown to be a transcription inhibitor which targets the liver, interfering with the synthesis of acute phase proteins. It is believed that these acute phase proteins, in fact, help the liver detoxify or deactivate TNFα. In fact D-Galactosamine treatment in the low dose endotoxin or exotoxin models is accompanied by TNFα mediated hepatic apoptosis. D-galactosamine treatment alone does not result in hepatic apoptosis, and these organ damaging effects can be neutralized in both low dose models by neutralizing anti-TNFα antibodies (Gutierrez-Ramos et al. 1997).

Mice used in sepsis or septic shock experiments: Female BALB/c and SJL mice between 8–12 weeks of age were used for all experiments. The animals were bred in our facility under specific pathogen-free conditions according to the protocols described in the Report of European Laboratory Animal Science Associations (FELASA) Working group on Animal Health (Laboratory Animals 28: 1–24, 1994).

Injection Protocols: Toxic Shock (TSST-1 & D-Galactosamine) (n=6).

For the exotoxin model, BALB/c mice were injected with 20 mg D-Galactosamine dissolved in 100 µl sterile saline solution (9%) intraperitoneally. They were then given 4 µg of TSST-1 dissolved in 100 µl sterile saline solution (9%) injected subcutaneously in two sites approximately 0.5 cm below each shoulder blade. Control groups were injected with either 4 µg TSST-1 subcutaneously without D-Galactosamine, or treated with D-Galactosamine alone. A group of D-Galactosamine sensitized BALB/c mice were also pre-treated i.p. with 700 IU IR-P for 3 days before the treatment of TSST-1. LPS model (n=6)

For the endotoxin model, BALB/c and SJL mice were treated i.p. with 600 µg LPS. Control groups were treated only with PBS i.p. To test the effect of IR-P, we also pre-treated BALB/c and SJL mice with 700 IU for 3 days and then injected with 600 µg of LPS. Moreover, a group of BALB/c mice was also pre-treated with IR-U fractions (IR-U1, IR-U2, IR-U3–5), each with the same doses of 200 µg i.p. for 3 days and then injected with 600 µg of LPS.

In order to test low molecular weight fraction, we tested IR-U/LMDF (which also contains IR-U5 [<10 Kda] fraction), IR-P3 (obtained by method 3), IR-A and IR-A3 (obtained by method 3), and their fractions obtained by method 4 for anti-shock activity. In addition, we also tested three fractions from peptide column (F1–3) for anti-shock activity (methods are shown elsewhere in this document). We also treated BALB/c mice with 700 IU IR-P twice i.p. after 1 and 2 hours of injection with LPS, respectively.

Semi-Quantitative Sickness Measurements: Mice were scored for sickness levels using the following measurement scheme:

1 Percolated fur, but no detectable behavior differences from normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund, sacrificed).

WBC and Platelets Counts: 100 µl of blood was obtained from 2 randomly selected mice per group utilizing a tail bleed method at the 24 hour time-point from TSST-1 model. Whole blood was collected in EDTA tubes and analyzed in an automated blood hematology analyzer.

Data on Shock Animals and Treatments: 8–10-wk-old female BALB/c mice obtained from Harlan were used in this study. Animals were killed and livers and spleens were excised for further study as indicated below. Mouse handling and experimental procedures were conducted in accordance with the American Association of Accreditation of Laboratory Animal Care guidelines for animal care and use.

Injection protocols: LPS from *E. coli* (Sigma Chemical Co) was administered intraperitoneally at 150 mg/kg for the high-dose LPS shock model. To test the effect of IR, mice were pre-treated with IR-P (PREGNYL) and its fractions, IR-PI, IR-P2, IR-P3 and with IR-A3 (APL) for 3 days (t=−3, t=−2, t=−1) each with the same dose of 200 mg i.p. and then LPS was injected at t=0h. A group of mice was also treated with IR-P or Dexamethasone twice i.p. after 1 and 2 hours of injection with LPS, respectively.

Blood test: From each group blood was withdrawn by a tail bleed of 3 mice at each time point (t=−72 h, −1 h and 48 h) and pooled for routine measurement of leukocytes, platelets, plasma enzymes LDH, ALAT and ASAT. Mice were then sacrificed and liver and spleens were excised and studied as indicated below.

Transplantation model: Animals and treatment: In order to determine whether IR-P is able to protect allograft, we treated BALB/c mice (n=5) with 600 I.U. IR-P/day i.p. or PBS for two days. On day 3, tail skin of C57BL/6 donors was grafted to the dorsar thorax of IR-P or PBS treated BALB/c recipients using a modification of the method of Billingham and Medawar. Grafts were considered rejected when no viable donor skin/hair was detectable. After transplantation, IR-P pre-treated BALB/c recipients were treated for an additional two days.

EAE Model (MS) Induction of EAE. 8–12 week-old female SJL mice (n=5) were immunized s.c. with 50 ml (0.5 mg/ml) of PLP-peptide at four different places (t=0). After 24 hours, $10^{10}$ *Bordetella pertussis* was injected i.v. in tail. Subsequently, after 72 (t=3) hours mice were again immunized with *Bordetella pertussis*. From day 7, mice were weighted and clinical signs of EAE were graded daily on a scale of 0 to 5 as follows:

| EAE score | symptoms |
| --- | --- |
| 0 | no signs |
| 0.5 | paresis or partial tail paralysis |
| 1 | complete tail paralysis |
| 2 | paraparesis; limb weakness and tail paralysis |
| 2.5 | partial limb paralysis |
| 3 | complete hind or front limb paralysis |
| 3.5 | paraplegia |
| 4 | quadriplegia |
| 5 | death |

IR treatment: A group of mice were also treated from day 8 with 600 I.U. IR-P/day i.p. three times a week for two weeks, while control group was treated with same volume of PBS.

Streptozotocin Model: Streptozotocin injections. For multiple dose streptozotocin (MD-STZ) model, 25 mg/kg of STZ (Sigma) were dissolved in citrate buffer (pH 4.2) and injected intraperitoneally within 5 min of solubilization as described previously. Male mice were injected on 5 consecutive days (experiment day 1 through day 5) at 6–9 weeks of age. After 5 consecutive days of STZ, mice were treated with IR-P (600 I.U. i.p.) (n=5) or citrate buffer (n=5) four times a week for three weeks. For high dose streptozotocin (HD-STZ) model, hyperglycemia was induced in mice by a single intraperitoneal injection of streptozotocin (160 mg/kg). Mice in the control group received a corresponding volume of citrate buffer alone.

Results: hCG Fraction Preparation and Characterization. Gel filtration of the solution of 1 or 2 vials of commercial grade hCG-PREGNYL (5,000 IU/vial) was performed on a Pharmacia FPLC system equipped with a Superdex 75 column (HR 5/30) (Pharmacia, SE) in PBS. Sample load volume was 1 ml. The flow rate was 0.5 ml/min for 45 min followed. The 1 minute flow rate of 0.2 ml/min was implemented because of the viscosity of the commercial grade hCG solution which has a high lactose content. hCG and a very low amount hCG core fragment were present in the relatively purified PREGNYL preparation of hCG and their positions were used as internal size markers. hCG eluted as 78 kDa molecules and the hCG β-core eluted as 19 kDa molecules on gel filtration. There were 1–5 fractions collected whereby fraction 1–2 contained hCG and fraction 5 contained the hCG (-core fragments). Fraction 1–2 and fraction 3–5 were tested for anti-diabetic effect by treating in vitro total spleen cells of 20-wk-old NOD and transferring them into NOD.scid. In this way, human recombinant hCG, α-hCG, and β-hCG (Sigma, St. Louis, Mo., US) were also tested.

Anion Exchange Chromatography and Further Treatment of IR-U and IR-P:

Further separation of the overlapping fractions, was done on a 1 ml MONO Q HR 5/5 anion exchange column. Two major protein peaks eluted at 43% and 55% buffer B, but were not separated suggesting covalent binding between these protein species. Even using a discontinuous elution gradient with a 50% buffer B hold did not result in separation of these peaks (data not shown). Therefore, we concluded that ion exchange chromatography could not be used for further purification due to covalent binding of protein species present in the urine sample.

To reduce the presumed covalent binding between the important protein species present in the IR-U sample, we treated the sample with 60 mM 2-mercaptoethanol for 3 min at 100° C. and the sample was then applied to the Superdex 75 column under identical conditions. The elution profile showed that peak 1 (70 kDa) remains present, fraction 2 (representing hCG, 37 kDa) nearly disappeared and resulted in two new peaks of a low molecular weight (<10 kDa). Peak 3 remained present and, therefore, is likely to contain isolated beta-core and monomeric proteins is excess. Peak 4 (10 kDa) also disappeared due to the reducing treatment.

A similar reducing treatment was applied to a sample of IR-P (PREGNYL). Like the profile of the IR-U sample also treated, hCG displayed the decrease in peak 2, increase in peak 3, while a new protein peak appeared between peaks 1 and 2. Moreover, an increase in the breakdown product peak (<10 kDa) was apparent.

Transfer Experiments: Total spleen cells were recovered from 9-wk-old NOD and stimulated in vitro in RPMI+ supplemented with 10% FBS with coated anti-CD3 (145–2c11; 25 mg/ml) and IL-2 (50 U/ml) along with 300 IU/ml IR-P, 100 mg/ml IR-U3–5 or IRU/LMDF. Plates were then incubated at 37° C. in 5% of $CO_2$ in air for 48 hrs. After 48 hrs, cells were twice washed with PBS and $20 \times 10^6$ cells were i.p. transferred into an 8-wk-old NOD.scid mouse.

In vivo Anti-diabetic Effect of IR: Four 15-wk-old NOD female mice (n=4) were treated with PBS, 300 IU PREGNYL, or 600 IU PREGNYL intraperitoneally, 3 times a week for four weeks. After the treatment, all mice in the PBS group were diabetic (blood glucose >33 mmol/l), they lost weight and looked uncomfortable, while the 300 IU PREGNYL and 600 IU PREGNYL groups remained free of disease. Their blood glucose levels never exceeded 6 mmol/l and they looked very healthy. In order to assess possible infiltrations and intact insulin-producing cells in the pancreas, mice from the PBS and the 600 IU PREGNYL groups were killed after treatment and entire pancreata were removed for immunohistochemistry for insulin. Pancreas sections from the PBS group showed many infiltrating cells in the pancreas and these cells penetrated the islets. There were also a large number of B-lymphocytes and T-lymphocytes present in the pancreata of the PBS-group. This finding was consistent with our other finding of an elevated ratio of splenic CD8/CD4 cells due to a selective reduction in the number of CD4+ cells and a decrease in the number of B lymphocytes in the spleen of these mice (data not shown). In the 600 IU PREGNYL group, pancreata were free of infiltration and, surprisingly, a number of new insulin-producing islets were seen. There was also a decrease in the number of B-lymphocytes and T-lymphocytes in the pancreas, which was consistent with normal levels of the CD8/CD4 ratio and the number of B-lymphocytes in the spleens of these mice. Mice from the 300 IU PREGNYL group were kept alive until the age of 28 weeks. They appeared healthy, did not lose their weight and never had blood glucose levels above 8 mmol/l. Immunohistochemistry for the presence of insulin was also performed. There were still infiltrating cells present and some insulin-producing islets in the pancreas. These mice were treated for four weeks with PREGNYL along with the 600 IU PREGNYL group and from wk 20 until 28 they were left untreated.

In order to determine whether the spleen cells of treated and untreated NOD mice still had the potential to induce diabetes in NOD.scid, we transferred spleen cells from the PBS and the 600 IU PREGNYL group into NOD.scid mice. 22 days after transferring, the PBS NOD.scid group were positive for diabetes and within a week they reached a blood glucose level above 33 mmol/l, while NOD.scid mice receiving spleen cells from the 600 IU PREGNYL group remained normal (blood glucose <7 mmol/1). 7 weeks after transferring, the PBS group looked very uncomfortable, while the 600 IU PREGNYL NOD.scid group still had blood glucose levels less than 9 mmol/l and remained healthy. Mice from both groups were killed at this time.

In vitro restimulation. Since high levels of IFN-γ, IL-1, and TNF-α were reported during the course of disease in NOD and this cytokine profile fits in a selective activation of the Th1 subset, we tested in vitro the effect of PREGNYL on cytokine production by total spleen cells and purified CD4+ cells from 20-wk-old NOD female mice. In order to assess whether the anti-diabetic effect resides in hCG or in one of its subunits or in other factors contained in the preparation used, we also tested the effect of different fractions obtained by gel permeation chromatography from PREGNYL and human recombinant hCG and its subunits on cytokine production. The effect of these fractions were also tested in vivo on blood glucose levels in reconstituted NOD.scid mice.

A strong inhibition of IFN-γ production by spleen cells obtained from mice treated with 50–600 IU/ml of PREGNYL, F3–5 (58–15 KDa) and to a lesser extent with human recombinant-βCG was observed (See, FIGS. 4-6 of the incorporated International Patent Publication PCT/NL99/00313 and associated text). There was only a moderate increase in IFN-γ production splenocytes from mice treated with 800 IU/ml PREGNYL. A similar pattern was observed when analyzing IL-4 production (See, FIG. 5 of the incorporated International Patent Publication PCT/NL99/00313 and associated text). In addition, a marked inhibition of IL-10 and TNF-α production was observed in stimulated splenocytes from mice treated with 300–600 IU/ml PREGNYL, with a concomitant stimulation of IL-6 and IL-10 production (data not shown).

Furthermore, transfer experiments showed that total spleen cells of 20-wk-old NOD mice treated with F3–5 or 600 IU PREGNYL can delay or even prevent the onset of diabetes in NOD.scid as compared to reconstitution with PBS treated NOD cells (See, FIG. 7 of the incorporated International Patent Publication PCT/NL99/00313 and associated text). However, no significant effect was observed with F 1–2 (80–70 KDa) on the onset of diabetes in NOD.scid mice. In order to test whether PREGNYL also has an effect on Th2 type mice, we treated BALB/c mice (n=5) with 300 IU PREGNYL i.p. for four days and with PBS (n=5). After isolating CD4+ cells from spleens, we stimulated them with anti-CD3/IL-2 for 48 hours and the supernatants were collected for the determination of IFN-γ and IL-4 cytokines. We also treated CD4+ cells with different doses of PREGNYL. Subsequently, the supernatants were collected for cytokine analysis. There was a marked inhibition of IFN-γ and a concomitant stimulation of IL-4 found in CD4+ cells stimulated with anti-CD3/IL-2 only (Th1->Th2), while the inverse was seen in CD4+ cells treated in vitro with different doses of PREGNYL (Th2->Th1).

Anti-diabetic activity of IR-U/LMDF In order to test the anti-diabetic activity of IR-U/LMDF (<5Kda), we treated diabetogenic cells in vitro with this fraction and with PBS (control). Transferring of these cells into NOD.scid mice revealed that reconstituted NOD.scid mice with IR-U/

LMDF-treated cells had delayed onset of diabetes as compared to the control group (n=3).

To determine the effect of IR on the potential of CD4+ cells to differentiate into Th1 cytokine-producing effector cells, the Th polarization assay was performed in the presence or absence of IR. We also tested recombinant hCG (rhCG) and beta-hCG in this Th polarization assay. A strong inhibition of IFN-gamma was found with IR-P and IR-U/LMDF on CD4+ cells polarizing towards the Th1 phenotype (See, FIG. 28 of the incorporated International Patent Publication PCT/NL99/00313 and associated text). There was only a moderate inhibition of IFN-gamma production observed with recombinant beta-hCG and no effect was seen with recombinant hCG (See, FIG. 28 of the incorporated International Patent Publication PCT/NL99/00313 and associated text).

To determine whether IR-P3 needed an additional factor, such as hCG, to exert its full activity, we also treated NOD mice with IR-P, its fraction IR-P3, rhCG and IR-P3 in combination with rhCG and then Th1 polarization was performed. FIG. 64 of the incorporated International Patent Publication PCT/NL99/00313 and associated text show that IR-P inhibited the production of IFN-gamma in the Th1 polarization assay and thereby inhibited the outgrowth of Th1 cells under Th1 polarizing conditions. There was moderate inhibition of the Th1 polarization found with IR-P3 and rhCG alone, while the outgrowth of Th1 cells was completely blocked with the combination of rhCG and IR-P3 (See, FIG. 64 of the incorporated International Patent Publication PCT/NL99/00313 and associated text).

We also stimulated spleen cells from these IR treated mice with anti-CD3 and then at different time points, IFN-gamma and IL-10 production was measured. FIG. 36 of the incorporated International Patent Publication PCT/NL99/00313 and associated text show that in vivo treatment with IR-P, and its fractions IR-P1, IR-P2, inhibited the in vitro anti-CD3 stimulated IFN-gamma production, while a moderate increase in IFN-gamma production was found with rhCG and IR-P3. In addition, fraction IR-P3 in combination with rhCG was able to inhibit the production of IFN-gamma (See, FIG. 65 of the incorporated International Patent Publication PCT/NL99/00313 and associated text). We also measured anti-CD3 stimulated IL-10 production (t=48) in splenocyte cultures of these in vivo treated mice. FIG. 67 of the incorporated International Patent Publication PCT/NL99/00313 and associated text show that all fractions (IR-P, IR-P1, IR-P2, IR-P3) were able to increase the production of IL-10.

Since IR and its fraction promote anti-CD3 proliferation of splenocytes in vitro, and in order to know the effect of in vivo treatment with IR on anti-CD3 stimulated proliferation in vitro, we also measured the anti-CD3 stimulated proliferation of splenocytes obtained from these IR treated mice at different time points (t=12, 24, 48 h). Anti-CD3 stimulated splenocytes from NOD mice treated with IR-P, and IR-P1 have a smaller capacity to proliferate in vitro. Furthermore, splenocytes from IR-P3 and rhCG treated mice showed a higher capacity to proliferate as compared to the PBS treated control mice (CTL), while IR-P3, in combination with rhCG, caused the same decrease in proliferation as IR-P. Moderate effect was found in the anti-CD3 stimulated proliferation of splenocytes from IR-P2 treated NOD mice.

As mentioned above, dominant Th1 polarization causes a B-cell switch from IgM to IgG2a production under the influence of massive production of IFN-gamma. Therefore, we also measured IgG2a production in LPS stimulated splenocytes obtained from IR treated NOD mice. FIG. 68 of the incorporated International Patent Publication PCT/NL99/00313 and associated text show that LPS stimulated splenocytes from IR-P, IR-P1 and IR-P3 treated produced in vitro less IgG2a, while moderate inhibition of IgG2a was found with IR-P2. Furthermore, rhCG treatment was not able to decrease the production of IgG2a while, in combination with IR-P3, it did (See, FIG. 68 of the incorporated International Patent Publication PCT/NL99/00313 and associated text).

GM-CSF STIMULATED NOD BONE MARROW CELLS: In order to determine the effect of IR on the maturation of dendritic cells (DC) from the bone marrow, we cultured bone marrow cells from 8-wk-old NOD mice for 7 days in the presence of GM-CSF. Under these conditions, the outgrowth of DC from bone marrow is more then 90%. When we co-cultured DC in the presence of GM-CSF and IR-P for 7 days, we observed that all DC treated with IR were less mature than control DC treated with GM-CSF only. This was concluded from the decrease in cell surface markers CD1d, ER-MP58, F4/80, CD14, and the increase in CD43, CD95, CD31 and E-cad. Moreover, no change was observed in cell surface markers ER-MP20/LY6C, MHC I and II.

In contrast, when DC were cultured with GM-CSF for 6 days and at day 7 co-cultured with 300 IU/ml IR-P or 100 mg/ml of IR-U/LMDF for an additional 24 hrs, the DC became more mature and could function better as APC. This was concluded from the increase in CD1d, CD40, CD80, CD86, CD95, F4/80, CD11c and MHC II cell surface markers.

BALB/c polarization assay: In order to test whether IR also has an effect on Th2 phenotype mice, we tested IR-P and IR-U/LMDF in BALB/c mice. After the IR treatment, we isolated CD4+ T-cells in the polarization assay. Polarization assays revealed that CD4+ T-cells from IR-P and IR-U/LMDF treated mice have less ability to produce IFN-gamma (See, FIG. 32 of The incorporated International Patent Publication PCT/NL99/00313 and associated text), while these cells produced more IL-4 as compared to cells from PBS-treated mice (See, FIG. 34 of the incorporated International Patent Publication PCT/NL99/00313 and associated text). This suggests that due to the in vivo treatment with IR, T-cells are shifted more towards Th2 phenotype. CD4+ T-cells from PBS treated and IR-P mice treated with different doses of IR-P showed an increase in IFN-gamma (See, FIG. 36 of the incorporated International Patent Publication PCT/NL99/00313 and associated text) and a decrease in IL-4 (See, FIG. 37 of the incorporated International Patent Publication PCT/NL99/00313 and associated text) production, which suggests a shift towards the Th1 phenotype. In order to determine whether a shift of CD4+ T-cells towards the Th2 phenotype is IL-10 or TGF-beta dependent, we also added anti-IL-10 and anti-TGF-beta in the polarization assays of CD4+ T-cells from IR-P treated mice. This caused an increase of IFN-gamma production under Th1 polarization conditions of IR-P treated mice cells and of IL-4 production under Th2 polarization conditions supported by anti-IL-10 addition (See, FIG. 38 of the incorporated International Patent Publication PCT/NL99/00313 and associated text) which suggests an involvement of IL-10 in Th1/Th2 polarization with IR-P. Furthermore, no big differences were seen of IL-4 and IFN-gamma production in Th2 and Th1 polarization conditions with anti-TGF-beta in vitro treatment (See, FIGS. 15 and 16 of the incorporated International Patent Publication PCT/NL99/00313 and associated text) between the control and IR-P treated group. This proves that due to the IR treatment, IL-10 and TGF-beta are involved. Moreover, purified CD4+ cell from IR-U/LMDF produce more TGF-beta then the cells from control mice (See, FIG. 43 of the incorporated International Patent Publication PCT/NL99/00313 and associated text). When anti-IL-10 or anti-IL-6 was added in both cultures, CD4+ cells from control group mice produce more TGF-beta than IR-U/LMDF treated group. This suggests an involvement of IL-6 and IL-10 in TGF-beta production. This is consistent with our data which shows that LPS stimulated spleen cells from IR treated mice produce a high level of IL-6 as compared to control mice.

Spleen cells from mice irradiated with UVB also produced more IL-10 and induced suppression of Th1 cytokines. LPS and anti-CD3 stimulation of spleen cells from these mice revealed they are less capable to proliferate. We also compared the LPS and anti-CD3 stimulated proliferation of spleen cells from UVB and IR treated BALB/c mice. Reduction in LPS and anti-CD3 induced proliferation was observed after culture of splenocytes from UVB treated BALB/c mice (See, FIGS. 46 and 47 of the incorporated International Patent Publication PCT/NL99/00313 and associated text), while IR or combined treatment by IR and UVB-irradiation treatment increased the LPS and anti-CD3 stimulated proliferation (See, FIGS. 46 and 47 of the incorporated International Patent Publication PCT/NL99/00313 and associated text).

IL-10 Knockout Mice Results: In order to determine whether this change in LPS and anti-CD3 stimulated proliferation is IL-10 dependent, we treated IL-10 knockout mice with IR-P or UVB. No change in proliferation pattern was seen in anti-CD3 stimulated spleen cells when UVB-irradiated and IR-P treated BALB/c mice were compared (See, FIG. 47 of the incorporated International Patent Publication PCT/NL99/00313 and associated text), while the inverse pattern in proliferation was observed in anti-CD3 stimulated lymph node cells as compare to UVB-irradiated BALB/c of both groups (See, FIG. 49 of the incorporated International Patent Publication PCT/NL99/00313 and associated text). This shows that the decrease in anti-CD3 stimulated proliferation after UVB treatment or increase in proliferation after IR-P treatment of spleen cells is not completely IL-10 dependent, while this is true for anti-CD3 stimulated lymph node cells. When the LPS stimulated proliferation of spleen cells was evaluated at 48 hours, we observed an increase of proliferation in the UVB and IR-P treated groups as compared to the control group (See, FIG. 51 of the incorporated International Patent Publication PCT/NL99/00313 and associated text), while a decrease in proliferation was observed in both groups at 72 hours of proliferation (See, FIG. 50 of the incorporated International Patent Publication PCT/NL99/00313 and associated text).

In order to determine the influence of in vivo UVB or IR-P-treatment on the percentage of positive cells for CD4, CD8, B220, M5/114 cell surface markers, we performed flow cytometry analysis on lymph node cells and spleen cells. Reduction in B220 and M5/114 positive cells, and an increase in CD4 and CD8 positive cells was observed in the lymph nodes of IR-P-treated IL-10 knockout mice (See, FIG. 52 of the incorporated International Patent Publication PCT/NL99/00313 and associated text), while an increase in CD4, CD8, B220 and M5/114 positive cells was observed in the spleen (FIG. 24). In the UVB treated group, an increase in CD8 positive cells and a decrease in CD4, B220, and M5/114 positive cells was seen in lymph nodes (See, FIG. 52 of the incorporated International Patent Publication PCT/NL99/00313 and associated text), while no change in cell markers was observed among spleen cells, except for a moderate increase in CD8 positive cells (See, FIG. 53 of the incorporated International Patent Publication PCT/NL99/00313 and associated text).

GM-CSF STIMULATED BONE MARROW CELLS Results: In order to determine the effect of IR on the maturity of dendritic cells (DC) of the bone marrow, we cultured bone marrow cells from BALB/c mice for 7 days in the presence of GM-CSF. In this way, the outgrowth of DC from bone marrow is more than 90%. When we co-cultured these DC in the presence of GM-CSF and IR (IR-P, IR-U, IR-U3–5, IR-U/LMDF) for 7 days, we observed that all DC treated with IR were less mature than control DC treated with GM-CSF only. This was concluded from the decrease in cell surface markers CD1d, CD40, CD80, CD86, ER-MP58, F4/80, E-cad and MHC II. Moreover, a moderate increase in CD95 was observed. In contrast, when DC were cultured with GM-CSF for 6 days and on day 7 the culture was supplemented with 300 IU/ml IR-P or 100 mg/ml IR-U (IR-U, IR-U3–5, or IR-U/LMDF) for an additional 24 hrs, they became more mature and could function better as APC. This was concluded from the increase in CD1d, CD14, CD40, CD80, CD86, CD95, ER-MP58, F4/80, RB68C5, E-cad and MHC II cell surface markers.

ALLO-MLR Results: In order to test the immunosuppressive activity of IR for instance, for transplantation purposes, we also performed allo-MLR with BM cells from 9-wk-old female BALB/c as mentioned above and cultured with GM-CSF (20 ng/ml) and IR (IR-P, 300 IU/ml; IR-U, 300 mg/ml; IR-U3–5, 300 mg/ml; IR-U/LMDF, 300 mg/ml) for 7 days. After 7 days these DC were irradiated (2,000 rad) and co-cultured in various ratios with splenic $CD3^+$ cells isolated from 9-wk-old female C57BL6/Ly. T-cell proliferation was measured via [$^3$H] TdR incorporation during the last 16 hrs in culture. Proliferation data shows that IR treated DC in all DC versus T-cell ratios tested are able to suppress proliferation (See, FIG. 56 of the incorporated International Patent Publication PCT/NL99/00313 and associated text).

Anti-shock activity of IR-U/LMDF, IR-P3, IR-A3: Lower molecular weight fraction of IR obtained by purification method 2 (IR-U/LMDF) had also anti-shock activity and mice treated with this fraction remained alive. We also tested all three fractions obtained from Superdex®peptide, IR-P3, and IR-A3 for anti-shock activity. The method for this activity screening is mentioned elsewhere in this document. Our results showed that all three fractions from the Superdex®peptide column and IR-P3 had anti-shock activity, while IR-A3 had low to moderate activity (data not shown).

Method 3 Purification: Three selected areas were fractionated, IR-P1 which elutes apparently with molecular weight of >10 kDa, IR-P2 which elutes apparently with molecular weight between the 10 kDa-1 kDa, and IR-P3 which elutes apparently with molecular weight <1 kDa. All these activities were tested for at least anti-shock activity and they all had anti-shock activity (shown elsewhere in this document). A macrosphere GPC 60 Å chromatogram of IR-P and IR-A sample was also performed (500 IU of each sample was injected with a same injection volume). The results revealed that IR-A contains large amount of IR-A3 fraction as compared to IR-P3 fraction in the IR-P sample. We have tested the same amount of IR-A and IR-P for their anti-shock activity. The results revealed that IR-A had low to moderate anti-shock activity compared to IR-P (results not shown).

Method 4 Purification: Pooled urine was obtained from pregnant women during the first trimester of their pregnancy. After desalting on a FDC column in an FPLC system and employing 50 mM ammonium bicarbonate as the running buffer, the pooled low molecular weight fractions (LMDF; <5 kDa) were lyophilized. The LMDF sample (13–17 mg) was suspended and applied on a Bio-Gel P-2 column using water for the elution. The elution profile was segregated into 8 different peaks and the poled fractions were tested for bioactivity in the LPS-induced septic shock (method mentioned elsewhere in document). Based on the inhibition of LPS shock, the activity was located in fractions Ic ("?"), II, III, VI, and VII. These peaks comprised elution volumes between 40–45 ml (peak Ic "?"), 45–50 ml (peak III), 60–65 ml (peak VI) and 65–70 ml (peak VII).

A sample of IR-P (PREGNYL) was applied on the Macrosphere GPC 60 Å column and eluted with ammonium bicarbonate. The third peak fraction(IR-P3) was pooled and applied on the Bio-Gel P-2 column and eluted with water into various peaks. Testing for activity in the LPS shock model revealed that the activity was located in the fractions located between the elution time of 7 and 9 hours.

A sample of IR-A (APL) was applied on the Macrosphere GPC 60 Å column and eluted with ammonium bicarbonate. The third peak fraction (IR-A3) was pooled and applied on the Bio-Gel P-2 column and eluted with water. Testing for activity in the LPS shock model revealed that the activity was located in the peaks 2, 3 and 7. These peaks comprised elution volumes between 105–115 ml (peak 2), 115–120 ml (peak 3) and 160–180 ml (peak 7).

In vivo Anti-Sepsis or Septic Shock Effect of IR

Survival Curve: The most striking results from this experiment are the black and white differences between those animals treated with IR-P prior to TSST-1 and D-Gal treatment versus those that were not (See, FIG. 20 of the incorporated International Patent Publication PCT/NL99/00313 and associated text). This is evident in the survival curve obtained from this experiment. While a 4 $\mu$g dose of TSST-1 coupled with D-Galactosamine sensitization was 100% lethal by 32 hours; animals pre-treated with IR prior to TSST-1 exposure did not succumb to the effects of lethal toxic shock.

LPS-treated BALB/c mice and SJL mice revealed different sensitivity to LPS. 600 $\mu$g LPS was 100% lethal by 48 hours and 36 hours in BALB/c and SJL, respectively, while IR pre-treated BALB/c and SJL mice remained alive. We also pre-treated BALB/c mice with IR-U fractions, namely, IR-U1, IR-U2 and IR-U3–5[pooled] and then treated with LPS. These experiments showed that IR-U1 and IR-U2 pre-treated mice were very sick by 48 hours and were killed along with LPS group. However, mice treated with IR-U3–5 remained alive.

A group of BALB/c mice were treated twice with 700 IU IR-P after the injection of LPS. The control group mice (only LPS) were killed at 48 hours time point because of their severe sickness. Mice treated with IR-P remained alive, except two (2/6) mice were killed at 60 hours time point.

Illness Kinetics: Visible signs of sickness were apparent in all of the experimental animals, but the kinetics, and obviously the severity of this sickness were significantly different. IR-P pre-treated BALB/c mice group did not exceed the sickness level 2 in TSST-1 exotoxin model (See, FIG. 21 of the incorporated International Patent Publication PCT/NL99/00313 and associated text) and also in LPS endotoxin model in addition to IR-U3–5 pre-treated mice. IR-P pre-treated SJL mice and IR-P post-treated BALB/c mice in LPS model did not exceed the sickness level 3. All mice in both models were killed when they exceeded the sickness level 5.

Shock Induced Weight Loss in TSST-1: IR pretreatment also resulted in significantly reduced weight loss of survivors of toxic shock. Weight loss data from this experiment was combined with that from another experiment which followed identical illness kinetics (data not shown), but resulted in two survivors of the 4ug TSST-1 &D-Gal without IR pre-treatment group.

When this weight loss data was statistically analyzed using a 2-sample T-test (using Minitab statistical software, version 11.21), significant differences (P(HO: $\mu 1=\mu 2$)<0.05) in weight loss were observable at 32 and 48 hours despite low n numbers, indicating an even higher possible significance if n were increased:

Two Sample T-Test and Confidence Interval
Two sample T for weight loss at 32 hours
(group 1=TSST1&D-Gal; group 2=T&D with IR pre-treatment)

| group | N | Mean | StDev | E Mean |
|---|---|---|---|---|
| 1 | 4 | 4.75 | 1.790 | 0.89 |
| 2 | 6 | 1.28 | 2.22 | 0.91 |

95% CI for $\mu 1-\mu 2$: (0.45, 6.48)
T-Test $\mu 1 = \mu 2$ (vs not =): T = 2.72 P = 0.030 DF = 7

Two sample T for weight loss at 48 hrs
(group 1=TSST1&D-Gal; group 2=T&D with IR pretreatment)

| group | N | Mean | StDev | SE Mean |
|---|---|---|---|---|
| 1 | 3 | 10.05 | 2.25 | 1.3 |
| 2 | 6 | 3.49 | 4.41 | 1.8 |

95% CI for $\mu 1-\mu 2$: (1.1, 12.0)
T-Test $\mu 1 = \mu 2$ (vs not =): T = 2.95 P = 0.026 DF = 6

WBC and Platelets Counts: White blood cell levels in blood were significantly higher in TSST- and D-Gal treatment alone versus WBC counts in regular mice and IR-P pre-treated mice. This indicates, as expected, a higher level of immune activation in the mice suffering from lethal toxic shock. There is still a normal level of WBC in the IR-P group. Such a finding also fits our other results, as this group did not show severe visible signs of illness. Blood platelet counts were also reduced in TSST-1 D-Gal treated mice. Elevated platelet counts were seen in IR-P treated mice.

Transplantation Results:

A major goal of transplantation research is the development of strategies to inhibit allograft rejection and, even better, to induce allo-specific tolerance. For this purpose, animal models have been widely used and it has become clear that skin allograft rejection may be one of the most difficult to prevent.

MHC-disparate graft loss is inevitable if allo reactivity is not suppressed by immunosuppressive agents. Currently, immunosuppressive protocols are based upon the combined use of multiple immunosuppressive agents which may potentially interfere with distinct steps of the rejection process, including antigen recognition, T-cell cytokine production, cytokine activity and T-cell proliferation, macrophages, NK cells and cytotoxic T-cell. In experimental settings, many drugs and monoclonal antibodies (mAb) have been and are being evaluated for their immunosuppressive capacity. Among these are mizorbine, RS-61443,15-deoxyspergualin, brequinar sodium and mAb against LFA-1, ICAM-1, CD3, CD4 and IL-2R. Cytokines produced by many cell types, such as T-cells, macrophages and NK cells, may influence the rejection process. Because of their central role in graft rejection, CD4+ T-cells and the cytokines they produce have been widely studied in rejection and acceptance of allografts. CD4+ T-lymphocytes can be subdivided into at least two subsets, Th1 and Th2 cells, based on their cytokine production pattern. Th1 cells, which produce IL2, TNF-gamma and TNF-beta, play a role in delayed type hypersensitivity (DTH) reactions and cellular cytotoxicity, whereas Th2 cells, which produce IL-4, IL5, IL-6 and IL-10, are effective stimulators of B-cell differentiation and antibody production. These two Th subsets can regulate each other's proliferation and function. While IFN-gamma inhibits Th2 cell proliferation and antagonizes IL-4 effects, IL-10 inhibits Th1 cytokine production. There are indications for the existence of regulatory T-cells which can also regulate these two subsets. Graft rejection is thought to be mediated by Th1 cells that may stimulate DTH and CTL activity. On the other hand, suppression of alloreactive Th1 cells may lead to graft acceptance.

Immunosuppression may be achieved by neutralizing pro-inflammatory cytokines by administration of anti-cytokine mAb or soluble cytokine receptors. Alternatively, "skewing" of T-cell differentiation towards one of the Th subsets can be achieved by varying the cytokine environment. For example, IFN-gamma (Th1, NK cells) and IL-12 (macrophages, B-cells) promote Th1 cell differentiation, whereas IL-4 (Th2) enhances Th2 cell development. Changing the in vivo cytokine environment by anti-cytokine mAb or cytokines, may have a similar effect. Moreover, induction of regulatory cells like Th3 and Th1 and like DC1 and DC2, also reduce transplant rejection and induce tolerance for graft.

Results: Treatment of BALB/c recipients with IR-P prolonged C57BL/6 skin graft survival as compared to the untreated control group. The control recipients rejected skin graft within 12 days while IR-P treated recipients were able to prolonged the graft until 22 days after transplantation.

EAE Results: Mice treated with PBS only lost weight during the first three weeks. These mice all had clinical signs of EAE of at least 2 and longer duration of the disease, except for one mouse which remained resistant to disease during the whole experiment. In the IR treated mice group there was less weight loss observed during the experiment and two mice were free of disease during the experiment. Sick mice in this group had maximum clinical scores of 2, had short duration of the disease, and recovered faster from EAE symptoms then the PBS treated group.

Results on shock: IR treated mice are resistant to LBS-induced shock: To determine the effect of high-dose LPS treatment in IR treated mice, BALB/c mice (n=30) were injected intraperitoneally with LPS (150 mg/kg) and survival was assessed daily for 5 days. PBS-treated BALB/c mice succumbed to shock between days 1 and 2 after high-dose LPS injection, with only 10% of mice alive on day 5 (See, FIG. 58 of the incorporated International Patent Publication PCT/NL99/00313 and associated text). In contrast, 100% of IR-P, or its fractions IR-P1 or IR-P3, treated mice were alive on day 5 (P<0.001) (See, FIG. 58 of the incorporated International Patent Publication PCT/NL99/00313 and associated text), while groups of IR-P2, IR-A and Dexamethasone treated mice demonstrated around 70% of survivors (See, FIG. 58 of the incorporated International Patent Publication PCT/NL99/00313 and associated text).

Blood test: Major manifestations of systemic response on LPS in shock is severe inflammation in organs, leading to organ failure or organ system dysfunction, initially in the liver. Therefore, we measured enzymes like ALAT, ASAT, LDH1 as well as WBC and platelets. FIG. 59 of the incorporated International Patent Publication PCT/NL99/00313 and associated text show that IR-A, IR-P and its fraction IR-P1, IR-P3 have all platelets counts within normal range (100–300×10$^9$/ml., while control, IR-P2 and Dexamethasone treated mice have platelets counts below normal range. FIGS. 60–62 of the incorporated International Patent Publication PCT/NL99/00313 and associated text show that mice treated with IR-A, IR-P and its fraction IR-P1, IR-P2 or IR-P3 had relatively low levels of ALAT, LDH1 and ASAT enzymes in the plasma as compared to control and dexamethasone treated mice. These enzymes were present in higher concentrations in blood during shock due to organ damage. These results are consistent with our surviving results (See, FIG. 58 of the incorporated International Patent Publication PCT/NL99/00313 and associated text). In addition, during shock, low numbers of WBC were found in blood because of their migration to the sites of inflammation. Our results in FIG. 63 of the incorporated International Patent Publication PCT/NL99/00313 and associated text show that mice treated with IR-A, IR-P and its fractions have moderate to normal levels of WBC at t=48 hours than control and dexamethasone treated mice, suggesting weaker inflammatory responses in IR treated mice.

Ex vivo NOD/LTJ Results: FIG. 64 of the incorporated International Patent Publication PCT/NL99/00313 and associated text show inhibition of IFN-gamma production in Th1 polarization assay with CD4+ cells isolated from NOD mice treated with IR-P or IR-P3 in combination with rhCG, while moderate inhibition was found in Th1 polarization by rhCG and IR-P3 alone. This shows that treatment with IP-P3 in combination with rhCG gives massive inhibition of Th1 outgrowth in NOD mice. This suggests that IR-P3 fraction needs rhCG for its maximum inhibition of the Th1 subset.

FIG. 65 of the incorporated International Patent Publication PCT/NL99/00313 and associated text show inhibition of IFN-gamma production in anti-CD3 stimulated spleen cells obtained from NOD mice treated with IR-P, IR-P1, IR-P2 or with IP-P3 in combination with rhCG as compared to PBS treated mice. rhCG and IR-P3 separately did not have the same effect as in combination. This suggests again that IR-P3 fraction needs rhCG for its IFN-gamma inhibition.

Anti-CD3 stimulated proliferation at different time points (t=12, 24, 48 h) of spleen cells obtained from NOD mice treated with IR-P, its fractions, rhCG, or IR-P3 in combination with rhCG. Again, the results are consistent with the previous IFN-gamma inhibition (See, FIG. 65 of the incorporated International Patent Publication PCT/NL99/00313 and associated text). Here, the IR-23 fraction is also needed rhCG for its inhibitory effect on anti-CD3 induced proliferation of spleen cells from in vivo treated NOD mice.

FIG. 67 of the incorporated International Patent Publication PCT/NL99/00313 and associated text show that IR-P and its fractions promote IL-10 production of anti-CD3 stimulated spleen cells from treated NOD mice as compared to PBS treated mice. FIG. 68 of the incorporated International Patent Publication PCT/NL99/003131 and associated text show that IgG2a production is not inhibited by in vivo treatment of NOD mice with IR-P2 or rhCG, while IR-P, IR-P1, IR-P3 and IR-P3 in combination with rhCG did inhibit the IgG2a production.

Since, IR-P3 in combination with rhCG has the same characteristics as IR-P, it is thinkable that this combination can also be used for the induction of pregnancy, IVF, prevention of abortions or related problems.

STZ Model The determining event in the pathogenesis of diabetes I is the destruction of insulin-producing pancreatic beta cells. There is strong evidence that the progressive reduction of the beta-cell mass is the result of a chronic auto-immune reaction. During this process, islet-infiltrating immune cells, islet capillary endothelial cells and the beta cell itself are able to release cytotoxic mediators. Cytokines, and in particular NO, are potent beta-cell toxic effector molecules. The reactive radical NO mediates its deleterious effect mainly through the induction of widespread DNA strand breaks. This initial damage presumably triggers a chain of events terminating in the death of the beta cell.

Diabetes induced in rodents by the beta-cell toxin streptozotocin (SZ) has been used extensively as an animal model to study the mechanisms involved in the destruction of pancreatic beta cells. SZ is taken up by the pancreatic beta cell through the glucose transporter GLUT-2. This substance decomposes intracellularly, and causes damage to DNA either by alkylation or by the generation of NO. The appearance of DNA strand breaks leads to the activation of the abundant nuclear enzyme poly(ADP-ribose) polymerase (PARP), which synthesizes large amounts of the (ADP-ribose) polymer, using NAD+ as a substrate. As a consequence of PARP activation, the cellular concentration of NAD+ may then decrease to very low levels, which is thought to abrogate the ability of the cell to generate sufficient energy and, finally, to lead to cell death.

Reactive radicals also play an important role in the pathogenesis of many diseases like nephropathy, obstructive nephropathy, acute and chronic renal allograft rejection, auto-immune diseases (like SLE, rheumatoid arthritis, diabetes, MS), AIDS, diseases related to angiogenesis, atherosclerosis, thrombosis and type II diabetes mellitus. For instance, recently increased oxidative damage to DNA bases has been shown in patients with type II diabetes mellitus which contribute to the pathogenesis and complications of diabetes. We tested whether IR also has the capacity to delay the induction of STZ-induced diabetes and thus also has an effect on cellular reactive radical forming and protection.

In HD-STZ models, the induction of diabetes is due to direct effect on beta cells of pancreatic tissue by inducing activation of PARP. Consequently, decrease of NAD+ and abrogation of the ability of the cell to generate sufficient energy finally leads to the cell death. This suggests that there is not any immunological component involved in this process. In contrast, in the MD-STZ model, strong immunological components are present. FIGS. 69 and 70 of The incorporated International Patent Publication PCT/NL99/003131 and associated text show that IR-P treatment is able to delay the induction of diabetes in both models. The mechanism behind this delay is probably of a different nature.

Human Studies

The immune system has a remarkable capacity to maintain a state of equilibrium even as it responds to a diverse array of microbes and despite its constant exposure to self-antigens. After a productive response to a foreign antigen, the immune system is returned to a state of rest, so that the numbers and functional status of lymphocytes are reset at roughly the pre-immunization level. This process is called homeostasis, and it allows the immune system to respond effectively to a new antigenic challenge. The size and the repertoire of the preimmune lymphocyte subpopulations are also closely regulated, as new emigrants from the generative lymphoid organs compete for "space" with resident cells. Lymphocytes with receptors capable of recognizing self-antigens are generated constantly, yet normal individuals maintain a state of unresponsiveness to their own antigens, called self-tolerance.

In auto-immune diseases, the immune system inappropriately recognizes "self," which leads to a pathologic humoral and/or cell-mediated immune reaction. In a normal, non-auto-immune state, self-reactive lymphocytes are deleted or made unresponsive to peripheral self ligands. Populations of potentially autoreactive cells can be demonstrated, yet appear not to give rise to apathogenic auto-immune reactions to their ligands. A picture of auto-immune disease is emerging wherein these autoreactive cells are activated through molecular mimicry, given that T-cell receptor (TCR) interactions can be degenerated and T-cells can be activated by a diversity of ligands (1, 2). There is evidence that under appropriate conditions, activation of autoreactive T-cells is facilitated by the induction of cytokines and the up-regulation of particular co-stimulatory molecules (e.g., CD80/CD86 and CD40), leading to autoimmunity.

When the immune system mistakes self tissues for nonself and mounts an inappropriate attack, the result is an auto-immune disease. There are many different auto-immune diseases. Some examples are Wegener's granulomatosis, multiple sclerosis, type 1 diabetes mellitus, and rheumatoid arthritis. Moreover, infection can also induce immune responses that lead to the induction of immune diseases, while the infection itself is not dangerous to the host. For example, the role of Tubercle bacilli in Tuberculosis, in which the immune system reacts top aggressively on Tubercle bacilli, resulting in inflammatory illness and tissue destruction due to its own immune response. The same is also true, for example, for lepta tuberculoid.

Auto-immune diseases can each affect the body in different ways. For instance, the auto-immune reaction is directed against the brain in multiple sclerosis and the gut in Crohn's disease. In other auto-immune diseases, such as Sjögren disease and systemic lupus erythematosus (lupus; SLE), affected tissues and organs may vary among individual with the same disease.

Many auto-immune diseases are rare. As a group, however, they afflict many people in Western societies. Many auto-immune diseases are more prevalent in women than in men. The sexual dimorphism covers a broad range of auto-immune disorders, ranging from organ-specific (such as Graves's disease) to generalized such as SLE. In MS, there is a female-to-male preponderance approaching 2:1 to 3:1. The reasons for the sex bias in MS and other auto-immune diseases are unclear but many include factors as sex-related differences in immune responsiveness to infection, sex steroid effects, and sex-linked genetic factors. It is recognized that MS, Sjögrens, SLE, and RA are different diseases and probably differ in etiology.

However, the common link is the overwhelming prevalence of these diseases in women. Considering that each of these diseases is auto-immune, the effects of sex hormones and gender may be similar, making a comparison of these diseases useful. Auto-immune diseases strike women, particularly during their working age and their childbearing years. However, the clinical course of these diseases are surprisingly less severe, or even remission is seen, during pregnancy.

During pregnancy, women undergo immunologic changes consistent with weakening of cell-mediated immunity (Th1 responses) and strengthening certain components of humoral immunity (Th2 responses). This Th2-biased like-response by the maternal system during pregnancy introduces a status of temporary immunosuppression or immunomodulation, which results in suppression of maternal rejection responses against the fetus but maintain, or even increase, her resistance to infection. In addition, decreased susceptibility to some auto-immune diseases, especially Th1-cell-mediated immune disorders have also been observed. For instance, approximately 77% of women with rheumatoid arthritis (predominantly a Th1-cell-mediated auto-immune disorder) experience a temporary remission of their symptoms during gestation, which are apparent from the first trimester in the majority of cases. Hence, clinical improvement during gestation in Th1-cell mediated auto-immune diseases should probably be related to physiologic immune changes during the early pregnancy.

Since our IR is able to inhibit the development of auto-immune disease in animal models such as NOD and EAE, we treated few patients with immune diseases. All patients were treated because of refractory disease and after informed consent.

PATIENT 1: Wegener's Granulomatosis

Wegener's granulomatosis is an auto-immune vascular disease that can affect both men and women and although it is more common in persons in their middle age, it can affect persons of any age. The initial manifestations generally involve the upper and lower respiratory tract, with a chronic, progressive inflammation. The inflammation may form lumps or granulomas in the tissues or in the skin. It may progress into generalized inflammation of the blood vessels (vasculitis) and kidneys (glomerulonephritis). A restricted form of the disease that does not involve the kidneys may occur.

The vasculitis is the result of an auto-immune reaction in the wall of small and medium-sized blood vessels. Chronic vasculitis causes a narrowing of the inside of the blood vessel and can result in obstruction of the flow of blood to the tissues. This situation may cause damage to the tissues (necrosis).

Auto-immune diseases occur when these reactions inexplicably take place against the body's own cells and tissues by producing self-reactive antibodies. In Wegener's granulomatosis, an autoantibody is directed toward components in the cytoplasm of certain white cells. The cause of Wegener's granulomatosis remains unknown. Though the disease resembles an infectious process, no causative agent has been isolated. Anti-Neutrophilic Cytoplasmic Antibody (ANCA) is found in the majority of patients, and its level appears to correlate with the disease activity. Wegener's granulomatosis is a quite rare disease, especially in Europe and in non-caucasians (Africans, South Americans, and Asians). The exact number of patients is not known, but a rough estimate is two new cases per million Americans per year, or about 500 new cases diagnosed every year in the United States. The disease can occur at any age; however, it has its peak in the 4th or 5th decade of life. It affects males and females equally. 85% of the patients are above age 19. The mean age of patients is 41 (current age range is 5–91). 97% of all patients are Caucasian, 2% Black and 1% are of another race.

The symptoms of Wegener's granulomatosis and the severity of these symptoms vary from one patient to another, although most patients first notice symptoms in the upper respiratory tract. A common manifestation of the disease is a persistent rhinorrhea ("runny nose") or other cold-like symptoms that do not respond to standard treatment, and that become progressively worse. Rhinorrhea can result from sinus drainage and can cause upper respiratory obstruction and pain. Complaints include discharge from the nose, sinusitis, nasal membrane ulcerations and crusting, inflammation of the ear with hearing problems, cough, coughing of blood and pleuritis (inflammation of the lining of the lung). Other initial symptoms include fever, fatigue, malaise (feeling ill), loss of appetite, weight loss, joint pain, night sweats, changes in the color of urine, weakness. Most Wegener's patients do not experience all of the above symptoms, and the severity of the disease is different with each patient. Fever is often present, sometimes resulting from bacterial infection in the sinuses. One third of the patients may be without, symptoms at the onset of the disease.

Laboratory tests are not specific for Wegener's granulomatosis and only suggest that the patient has an inflammatory disease. Blood tests often show anemia (low red blood cell count) and other changes in the blood. Chest X-rays and kidney biopsy are important tools used in diagnosing Wegener's granulomatosis. For effective treatment, early diagnosis is critical. Asymptomatic patients can be diagnosed by ANCA blood tests and CT scans of sinuses and lungs. It takes 5–15 months, on average, to make a diagnosis of Wegener's granulomatosis. 40% of all diagnoses are made within less than 3 months, 10% within 5–15 years.

Other diagnostic tools include erythrocyte sedimentation rate is generally elevated, complete blood count often shows anemia, elevated white counts, elevated platelet counts, urinalysis is often considered as a screening test for kidney involvement, 24-hour urine collection is used in certain patients to assess kidney function, and c-ANCA is characteristic, measuring Proteinase-3 antibodies.

Our initial results of treatment of patient 1 with IR-P. The patient was treated because of refractory disease and after informed consent.

Diagnosis: Wegener's granulomatosis based on sinal histopathology and cANCA test. Case: A 34 year old male patient known with relapsing Wegener's granulomatosis for 5 years. This patient was treated with high dosage steroids, cyclosporine (5 mg/kg) and cyclophosphamide (1–2 mg/kg). Because of progressive disease in July 1998 he was treated with IR (PREGNYL), 5000 I.U, s.c. daily.

Before IR treatment the patient was immuno-compromised due to the high doses of steroids. After IR treatment, the levels of T-lymphocytes (CD4, CD8) were increased and within normal range, except for B-cells. We also measured cytokines in LPS and PMA/Ca stimulated PBMC obtained from patient during the IR treatment. We observed that LPS stimulated PBMC produced more TNF-alpha, IL-10 and IL-12 during treatment (See, FIG. 82a of the incorporated International Patent Publication PCT/NL99/00313 and associated text), while PMA/Ca stimulated PBMC produced less IFN-gamma (See, FIG. 82b of the incorporated International Patent Publication PCT/NL99/00313 and associated text). Accordingly, we show that IR treatment increases the production of anti-inflammatory cytokines (IL-10, TNF) while it decreases the production of inflammatory cytokine (IFN-gamma). This is consistent with our clinical observation that during 3 months of treatment, no further progression was observed as measured by sinal inflammation activity. These results suggest a beneficial effect of IR-P.

PATIENT 2: Polymyositis: Definition: A systemic connective tissue disease, which occurs through T-cell mediated inflammation causing destruction of muscle fibers. Other possible causes of these syndromes include complement activation, infection, drugs, stress, vaccines. It can affect people at any age, but most commonly occurs in those between 50 to 70 years old, or in children between 5 to 15 years old. It affects women twice as often as men. Muscle weakness may appear suddenly or occur slowly over weeks or months. There may be difficulty with raising the arms over the head, rising from a sitting position, or climbing stairs. The voice may be affected by weakness of the larynx. Joint pain, inflammation of the heart, and pulmonary (lung) disease may occur. A similar condition, called dermatomyositis, is evident when a dusky, red rash appears over the face, neck, shoulders, upper chest, and back. A malignancy may be associated with this disorder. The incidence of polymyositis is 5 out of 10,000 people.

Patient 2: Diagnosis: Systemic sclerosis/polymyositis overlap (based on histopathology). Case: A 50 year old woman who suffered for two years from systemic sclerosis with an active polymyositis component. She was treated with DAPSONE, steroids, methotrexate and cylosporine. Because of refractory myositis as measured by the creatin phosphate level, she was treated for three months with a combination of prednisone, zyrtec and PREGNYL 5000 I.U., s.c. During treatment, the CPK level dropped from 1100 to 750. This reflects a decrease in disease activity.

FIG. 83 of the incorporated International Patent Publication PCT/NL99/00313 and associated text show that due to the IR-P treatment the number of lymphocytes, T-cells (CD4, CD8) and B-cells were decreased which indicates the down-regulation of the hyperactive immune system due to the treatment. This is also consistent with our cytokine data (See, FIG. 86 of the incorporated International Patent Publication PCT/NL99/00313 and associated text) which shows inhibition of LPS stimulated IL-12 and TNF-alpha by PBMC. Moreover, there was an increase in IL-10 production during the treatment, which is an anti-inflammatory cytokine (See, FIG. 86 of the incorporated International Patent Publication PCT/NL99/00313 and associated text). In addition, the elevated CPK and liver enzymes (ASAT, ALAT) were also decreased (See, FIGS. 84 & 85 of the incorporated International Patent Publication PCT/NL99/00313 and associated text). This all reflects a decrease in the disease activity.

Diabetes mellitus is a chronic disorder characterized by impaired metabolism of glucose and other energy-yielding fuels, as well as the late development of vascular and neuropathic complications. Diabetes mellitus consists of a group of disorders involving distinct pathogenic mechanisms with hyperglycemia as the common denominator. Regardless of cause, the disease is associated with insulin deficiency, which may be total, partial, or relative when viewed in the context of co-existing insulin resistance. Lack of insulin plays a primary role in the metabolic derangements linked to diabetes and hyperglycemia, in turn, plays a key role in the complications of the disease. In the United States, diabetes mellitus is the fourth most common reason for patient contact with a physician and is a major cause of premature disability and mortality. It is the leading cause of blindness among working-age people, of end-stage renal disease, and of nontraumatic limb amputations. It increases the risk of cardiac, cerebral, and peripheral morbidity and mortality. On the bright side, recent data indicate that most of the debilitating complications of the disease can be prevented or delayed by prospective treatment of hyperglycemia and cardiovascular risk factors.

Insulin-dependent diabetes mellitus (IDDM) is one of the clinically defined types of diabetes and develops predominantly in children and young adults, but may appear in all age groups. The major genetic susceptibility to IDDM is linked to the HLA complex on chromosome 6. These genetic backgrounds interact with environmental factors (possibly certain viruses, foods and climate) to initiate the immune-mediated process that leads to beta cell destruction. While non-insulin dependent diabetes ("NIDDM"), which is another clinically defined type of diabetes, is the most common form of diabetes, the prevalence of NIDDM varies enormously from population to population. The greatest rates have been found in the Pima Indians. The major environmental factors identified as contributing to this form of diabetes are obesity and reduced physical activity. NIDDM shows strong familial aggregation in all populations and is clearly the result of an interaction between genetic susceptibility and environmental factors. Before NIDDM develops, insulin concentrations are high for the degree of glycemia and of obesity, reflecting the presence of insulin resistance. As insulin resistance worsens, glucose levels increase, with the appearance of glucose intolerance and, finally, of NIDDM, when insulin response cannot compensate for insulin resistance.

Since our preliminary mice data shows that IR has the ability to shift Th1 phenotype cytokines towards Th2 phenotype and IR is also able to inhibit diabetes in NOD mice, we postulated that it should also have positive clinical effects in human immune diseases like diabetes.

Patient 3: Diagnosis: Diabetes mellitus type I Case: Patient is a 21 year old male suffering from diabetes mellitus since 3 months. He was treated with insulin (ACTRAPID and INSULATARD). High level of anti-islet cell antibodies was in his blood. He was treated with PREGNYL 5000 I.U. s.c. for three months. During his treatment, the insulin needed to maintain euglycemia decreased. After withdrawal of PREGNYL, his insulin need raised again. In this patient with the new onset of diabetes mellitus, the insulin need dropped significantly during treatment with IR-P and also improvement of glucose control was found, supported by a decrease in glycosylated HbAlc level during IR-P treatment and a decrease in inflammatory cytokines (IL 12, TNF-alpha, IFN-gamma) produced by LPS stimulated PBMC (FIG. 65 of The incorporated International Patent Publication PCT/NL99/003131 and associated text). Furthermore, increase in IL-10 (anti-inflammatory cytokine) was also observed during the treatment (FIG. 65 of The incorporated International Patent Publication PCT/NL99/00313 and associated text). Accordingly, this suggests an improvement of the islet cell function and, eventually, also better glucose regulation.

Multiple Sclerosis and Related Conditions (in vitro Data)

Multiple Sclerosis (MS) is a disorder of unknown cause, defined clinically by characteristic symptoms, signs and progression, and pathologically by scattered areas of inflammation and demyelination affecting the brain, optic nerves, and spinal cord. The first symptoms of MS most commonly occur between the ages of 15 and 50.

The cause of MS is unknown, but it is now widely believed that the pathogenesis involves immune-mediated inflammatory demyelination. Pathologic examination of the MS brain shows the hallmarks of an immunopathologic process-perivascular infiltration by lymphocytes and monocytes, class II MHC antigen expression by cells in the lesions, lymphokines and monokines secreted by activated immune cells, and the absence of overt evidence for infection. Additional evidence for an auto-immune pathogenesis includes (1) immunologic abnormalities in blood and cerebrospinal fluid (CSF) of MS patients, notably selective intrathecal humoral immune activation, lymphocyte subset abnormalities, and a high frequency of activated lymphocytes in blood and CSF; (2) an association between MS and certain MHC class II allotypes, (3) the clinical response of MS patients to immunomodulation tends to improve with immunosuppressive drugs and worsens with interferon-gamma treatment, which stimulates the immune response; and (4) striking similarities between MS and experimental auto-immune encephalomyelitis (EAE)—an animal model in which recurrent episodes of inflammatory demyelination can be induced by inoculating susceptible animals with myelin basic protein or proteolipid protein.

Epidemiologic studies suggest environmental and genetic factors in the etiopathogenesis of MS. The uneven geographic distribution of the disease and the occurrence of several point-source epidemics have suggested environmental factors; however, intense study over the past 30 years has failed to establish an infectious cause. Migration studies have shown that exposure to undefined environmental factors prior to adolescence as required for subsequent development of MS. A genetic influence is well-established by excess concordance in monozygotic compared with dizygotic twins, clustering of MS in families, racial variability in risk, and association with class II MHC allotypes. In Caucasians, the HLA class II haplotype DR15, DQ6, Dw2 appears strongly and consistently associated with an increased risk of MS.

The evidence—immunologic, epidemiologic, and genetic—supports the concept that exposure of genetically susceptible individuals to an environmental factor(s) during childhood (perhaps any one of many common viruses) may lead eventually to immune-mediated inflammatory demyelination. The precise interplay between genetic, environmental and immunologic factors and the nature of the environmental trigger(s) remains to be elucidated. We isolated PBMC from MS patients and stimulated these with LPS or PMA/Ca. After 24 hours of culture, supernatants were collected for cytokine analysis (TGF-beta, IL-10, IFN-gamma).

MS patient 1 (in vitro): there was an increase in production of TGF-beta and IL-10 in LPS stimulated PBMC treated with IR-P. No differences were observed in TGF-beta and IL-10 production in cultures stimulated with PMA/Ca and treated with IR-P, while IR-P inhibited the production of IFN-gamma in PMA/Ca stimulated PBMC.

MS patient 2 (in vitro): PBMC obtained from patient 2 showed a decreased production of TGF-beta and IFN-gamma in cultures treated with IR-P as compared to TPA/Ca stimulation alone, while IR-P treatment increased LPS stimulated TGF-beta production. IL-10 production was inhibited with IR-P in both LPS and TPA/Ca stimulated cultures.

The stimulating effect of IR-P on the production of anti-inflammatory cytokines by PBMC from MS patients in vitro and the inhibitory effects on the production of inflammatory cytokines correlated with the beneficial clinical effects of IR-P treatment of SJL mice in which EAE was induced.

Human Bronchial Epithelial Cell Line BEAS 2B (Asthma in vitro Data):

Diseases characterized by airway inflammation affect a substantial proportion of the population. These diseases include asthma and chronic obstructive pulmonary disease ("COPD"). In the European Union, COPD and asthma, together with pneumonia, are the third most common cause of death. The production of cytokines and growth factors in response to irritants, infectious agents and inflammatory mediators play an important role in the initiation, perpetuation and inhibition of acute and chronic airway inflammation.

Airway inflammation is associated with excessive production and activity of several mediators and cytokines released by inflammatory and resident cells in the airways. Now it is clear that the epithelium is not only an important target for the action of mediators of inflammation, but also an active participant in the inflammatory process itself. Bronchial epithelial cells are able to recruit inflammatory cells to the airways through the release of chemoattractants, to direct inflammatory cell migration across the epithelium through the expression of cell adhesion molecules, and to regulate the inflammatory activity of other cells through the release of mediators, like cytokines, chemokines, arachidonic acid metabolites and relaxant and contractile factors.

Bronchial epithelial cells not only form a passive barrier but also play an active role in the immune response. They are able to produce a variety of mediators that may act either pro- or anti-inflammatory. In addition, bronchial epithelial cells may express adhesion molecules for many different-cell types, thereby contributing to their recruitment.

TNF-alpha produced by inflammatory cells present in the air ways can trigger other inflammatory cytokines and chemokines like RANTES and IL-6. It can also down regulate the production of anti-inflammatory cytokines and thereby damage the barrier function of epithial cells. Glucocorticoids inhibit the transcription of most cytokines and chemokines that are relevant in asthma, including IL-6, RANTES, IL-4. This inhibition is at least partially responsible for the therapeutic effects of glucocorticoids.

Our results (See, FIGS. 71–73 of the incorporated International Patent Publication PCT/NL99/003131 and associated text) are consistent with these findings, and show that Dexamethasone is able to inhibit TNF-alpha induced IL-6 and RANTES production in the BEAS 2B-cell line. IR-P is also able to inhibit the production of TNF-alpha induced inflammatory cytokines. Moreover, dexamethasone was able to restore TNF-alpha induced down-regulation of anti-inflammatory TGF-beta cytokine, while IR-P not only restores TGF-beta production but also promotes this anti-inflammatory cytokine further (See, FIG. 73 of the incorporated International Patent Publication PCT/NL99/003131 and associated text). In addition, Dexamethasone and IR-P were both able to inhibit IFN-gamma induced production of RANTES (See, FIG. 74 of the incorporated International Patent Publication PCT/NL99/00313 and associated text).

TNF-alpha can also induce cell adhesion markers, such as HLA-DR and ICAM-1 on the surface of epithelial cells which then recruit inflammatory cells. In this way epithelial cells can also function as antigen presenting cells (APC). Our results show that Dexamethasone and IR-P both were able to down-regulate the TNF-alpha induced expression of HLA-DR and ICAM-1 (See, FIG. 75 and 76 of the incorporated International Patent Publication PCT/NL99/00313 and associated text).

These results show that IR-P also has the ability to affect the clinical course of diseases characterized by Th2-type cytokine phenotype-like allergy, asthma and particular parasitic diseases.

Discussion: Nonobese diabetic (NOD) mice naturally develop an insulin-dependent diabetes (IDDM) with remarkable similarity in immunopathology and clinical symptoms to human IDDM patients. As a result, NOD mice have become a valuable tool for studying the underlying immunobiology of IDDM and the complex genetics that control it. Through their study, we now know that diabetes is caused by an imbalance in the ratio of the Th1/Th2 subsets and consequently, the destruction of insulin producing β-cells. This destruction is coordinated by β-cell antigen-specific CD4+ T-cells that produce proinflammatory cytokines like IFN-γ, TNF-α/β, and IL-1. A growing number of studies has now correlated diabetes (in mice and in humans) with a preferential development of Th1-like cells.

In contrast, pregnancy is thought to be a selective Th2 phenomenon, and surprisingly during pregnancy the severity of many immune-mediated diseases has been seen to reduce. In contrast, Gallo et al. have shown that hCG mediated factor(s) (HAF) present in the urine of first trimester pregnancy have an anti-tumor (and anti-viral) effect, which is possibly achieved by a direct cytotoxic effect on tumor cells and, according to these authors, not by an immune-mediated response.

Here, we show an immunoregulator obtainable, for example, from urine of first trimester pregnancy not only affects the above mentioned immune deviation during pregnancy, but also affects the development of diabetes in NOD mice.

Our results show that, for example, PREGNYL, a partially purified hCG preparation from urine of first trimester pregnancy, can delay the onset of diabetes, for example in 15-wk-old NOD when treated for only 3 times a week during four weeks. In addition, spleen cells isolated from these treated mice upon transfer have also the potential to delay the onset of diabetes in immuno—compromised NOD.scid mice. We fractionated a PREGNYL preparation to assess whether this anti-diabetic activity resides in hCG itself, its subunits, β-core (natural break-down product of β-hCG) or in unidentified factors (HAF). It is worth knowing that PREGNYL is one of the most purified hCG preparations available and it contains only low amounts of β-core fragments. We found that most of the anti-diabetic activity resided in a fraction without hCG. Furthermore, we showed that human recombinant α-hCG and β-hCG also had no effect. However, we do not exclude the possibility that hCG can synergize with other factors in diabetes and other immune-mediated diseases.

Immunohistological analysis of the presence of insulin and infiltration in the pancreas of NOD mice showed that NOD mice treated with 600 IU PREGNYL did not reveal a significant infiltrate. Moreover, new insulin islets were seen in the pancreas, which shows a possible regeneration process induced by this treatment. As mentioned before, normally at the age of 9 weeks, infiltrating cells penetrate into the islets and the islets become swollen with lymphocytes. In our experiments, the NOD mice were 15-wk-old and the PBS treated control mice had many infiltrating cells and almost no insulin-producing cells at that time in their pancreas. In addition, PBS treated mice had also an elevated ratio of CD8/CD4 in their spleen and many T-cells in their pancreas. Since our treated mice had a normal CD8/CD4 ratio in their spleen and no infiltration was found in their pancreas, the elevated CD8/CD4 ratio was due to selective recruitment of CD4+ cells into the pancreas. IFN-γ and TNF-A are involved in the recruitment of T-lymphocytes (Rosenberg et al. 1998).

Our results show that treatment of NOD mice with 600 IU PREGNYL for four weeks had dramatic effects on the morphology and function of their otherwise inflamed pancreas. Furthermore, our 300 IU PREGNYL NOD mice were kept alive until the age of 28 weeks without treatment and remained non-diabetic. The 600 IU PREGNYL NOD mice were also examined for symptoms of generalized autoimmune diseases, like Sjögren's disease, which were not found. Our in vitro experiments with total spleen cells and purified CD4+ cells of NOD are consistent with the in vivo data. There was marked inhibition of IFN-γ, IL-1 and TNF-A release by spleen cells (data not shown) from NOD mice treated in vitro with PREGNYL, F3–5, and to a lesser extent with human recombinant β-hCG. Increase in IL-4 production was also observed implying a shift of Th1 to Th2 type response with the treatment. However, doses above 800 IU PREGNYL caused opposite results and may be due to the presence of a high amount of hCG itself.

The immune system is clearly involved in the onset of diabetes. Treatment with PREGNYL affects the immune system and thereby can reduce the disease activity in NOD mice. In order to separate the immune-modulating activity of PREGNYL from its beneficial clinical effect, we treated healthy BALB/c mice. This strain is generally considered to react upon stimulation with a Th2 driven immune response. Our results suggest that purified OD4+ T-cells obtained from PREGNYL-treated BALB/c mice display a further Th2 skewing. The same cells, when restimulated with PREGNYL in vitro, showed an enhancement of IFN-γ production and a decrease in IL-4 production. This implies that PREGNYL affects different regulatory T-cell subsets upon treatment in vivo versus in vitro. We suggest that treatment in vivo stimulates the outgrowth of a population of presumably CD4+ Tr1 cells, characterized by selective production of TGF-13 and a lower or no production of IL-10. These CD4+ Tr1 cells have been shown (O'Garra et al. 1997) in different models of Th1 driven diseases including diabetes and MS, to selectively inhibit the activity of Th1 cells, thereby also decreasing the disease severity. Similarly CD4+ T-cells from PREGNYL treated BALB/c mice restimulated in vitro with PREGNYL showed an increase of Th1 cells concomitant with a decrease of Th2 cells. This is consistent with a preferential stimulation of the CD4+ Th3 cells characterized by a high production of IL-10 and a low production of TGF-β. These regulatory cells are inhibitors of IFN-γ production by Th1 cells as well as the outgrowth of Th2 type cells. It has also been shown that in NOD.scid mice a steady increase of Th2 cells is responsible for the less severe hyperglycemia and the different nature of the infiltrates in the pancreatic islets.

Our results of the 300 IU PREGNYL treated NOD and our reconstituted NOD.scid mice showed a similar slow increase in blood glucose, particularly in NOD.scid, and a different nature of the infiltrates as compared to PBS-treated NOD. In NOD mice, the activity of PREGNYL might well be mediated with the induction of Th3 cells inhibiting both Th1 and Th2 cells. These Th3 cells may suppress the disease activity for prolonged periods of time at the very least. In NOD.scid mice, having no functional T-cells, reconstitution with PREGNYL-treated spleen cells is mediated with selective induction of Th1 cells, thereby inhibiting the Th1 subset only. After prolonged periods, the steady outgrowth of diabetogenic Th2 cells is responsible for the late onset of a less severe form of diabetes. Similarly, our F3–5, but not F1–2, displays the above-discussed phenomenon, arguing that hCG cannot be responsible for the observed affects. This F3–5 is principally pointing towards a decisive effect on the immune response in the onset of auto-immune diabetes and is an active component for immunotherapy of this disease and other immune-mediated disorders.

In addition, PREGNYL and immunoregulators functionally equivalent thereto, is effective in Noninsulin-diabetes mellitus (NIDDM). The essential problem in NIDDM patients is the insulin resistance and obesity. It has been shown that TNF-(alpha) is the cause of the insulin resistance and obesity of NIDDM (Miles et al. 1997, Solomon et al. 1997, Pfeiffer et al. 1997, Hotamisligil et al. 1994), Argiles et al. 1994). This insulin resistance induced by TNF-alpha can be reversed by recently developed medicines like Pioglitazone and Metformin, and with engineered human anti-TNF-alpha antibody (CDP571) (Solomon et al. 1997, Ofei et al. 1996), which possibly achieved their beneficial action by lowering the TNF-alpha-induced free fatty acid (FFA) concentration of the blood and/or by stimulating glucose uptake at an intracellular point distal to the insulin receptor autophosphorylation in the muscle. Furthermore, the presence of retinopathy (Pfeiffer et al. 1997) (one of the late complications of diabetes) has been mediated with significantly elevated plasma TNF-alpha and is sex-dependent (Pfeiffer et al. 1997). The increased TNF-alpha occurs in male but not in female NIDDM and may participate in the development of retinopathy and other complications like neuropathy, nephropathy or macroangiopathy (Pfeiffer et al. 1997). Since PREGNYL and fraction 3–5 have immune modulating potential and, in particular, inhibit TNF-alpha directly or indirectly, PREGNYL and its fraction 3–5 also have beneficial effects in NIDDM patients. Lower incidence of diabetes complications among females could implicate the involvement of female hormones. A key pathogenic cytokine indicated in sepsis or septic shock is the immunological mediator TNFα which occupies a key role in the pathophysiology associated with diverse inflammatory states and other serious illnesses including sepsis or septic shock and cachexia. When TNF is produced by T-cells (for example, by T-cell activation through superantigen [exotoxin] or by macrophages through endotoxin), it mediates an inflammatory response that may alienate and repel the attacking organisms. When the infection spreads, the subsequent release of large quantities of TNF into the circulation is catastrophic, damaging the organ system and triggering a state of lethal shock. These toxic effects occur by direct action of TNF on host cells and by the interaction with cascades of other endogenous immunological mediators including IL-1, IFN-gamma.

This has been shown by induction of shock-like symptoms in mice sensitized with D-Galactosamine and treated with TNFα as well as inhibition of both lethality and visible signs of disease after concurrent infusion of anti-TNFα mAbs following TSST-1 and D-Galactosamine treatment. In the low dose endotoxin model and in the exotoxin model, D-Galactosamine treatment is necessary to inhibit the transcription of acute phase proteins that allow the liver to detoxify the high levels of TNFα present following shock induction. The lack of these acute phase proteins leads to increased susceptibility of murine hepatocytes to TNFα mediated apoptosis induction. This apoptosis, and inability to neutralize the inflammatory effects of TNFα eventually lead to death.

We have shown that factors (IR) with or without hCG present in, for example, the urine of the first trimester of pregnancy (IR-U) and in commercial hCG preparations (IR-P) have immune regulatory effects. In particular, they have the potential to inhibit auto-immune and inflammatory diseases. Since TNF and IFN-gamma are pathologically involved in sepsis or septic shock and also in auto-immune and inflammatory diseases, IR also has the ability to inhibit TNF and IFN-gamma in acute inflammatory states like shock. Our results show that IR inhibits sepsis or septic shock in BALB/c or SJL, treated with LPS (endotoxin model) or with TSST-1 (exotoxin model). IR not only has the potency to inhibit chronic inflammatory diseases, but it can also suppress acute inflammatory diseases like shock. Moreover, we also show that even post-treatment with IR inhibits the shock. Furthermore, our IR fraction data show that most of the anti-shock activity resides in fractions IR-(U/P)3–5 [pooled] which contain mostly individual chains of hCG, homodimers of these chains or beta-core residual chains, breakdown products of these chains and other molecules (>30 kDa). We have also shown that the same fractions IR-U/P3–5 have anti-diabetic effect in NOD mice models. Thus, the endotoxin and exotoxin model serves as a fast readout model for the determination of anti-diabetic activity in NOD mice and NOD.scid mice. With the help of endotoxin and exotoxin models, we can check for anti-diabetic activity in IR fractions within 48 hours.

Thus, IR such as PREGNYL and its fraction 3–5 have high potency to suppress auto-immune diabetes by modulating the immune system by effecting regulatory T-cell subsets. Our NOD and BALB/c data show that they have the potential to restore the T-cell subset balance (Th1–>Th2/Th2–>Th1). Therefore, PREGNYL and its fraction 3–5 are effective in modulating the severity of other immune-mediated diseases too, like diseases where Th1 cytokines are dominant such as Rheumatoid Arthritis (RA), Multiple Sclerosis (MS), NIDDM, Systemic lupus erythematosus (SLE), transplantation models and diseases like allergies and asthma where Th2 cytokines responses are dominant. Animal models of these diseases (like EAE model for MS, BB-rats for NIDDM, Fishe-rat and MLR-models for RA, OVA-model for allergies, MLR/lpr and BXSB-models for SLE), KK-Ay-mice, GK rats, wistar fatty rats, and fa/fa rats provide, amongst others, models of other immune-mediated diseases.

REFERENCES

Abbas, A. K., K. M. Murphy, and A. Sher. 1996. Functional diversity of helper T lymphocytes. *Nature* (Lond.). 383:787–793.

Argiles J. M., Lopez-Soriano J., Lopez-Soriano F. J. 1994. Cytokines and diabetes: the final step? Involvement of TNF-alpha in both type I and II diabetes mellitus. *Horm. Metab.Res.* 26:447–449.

Atkinson, M. A., and N. K. Maclaren. 1994. The Pathogenesis of insulin-dependent diabetes mellitus. *N. Engl. J. Med.* 331:1428–1436.

Bach, J. F. 1991. Insulin-dependent diabetes mellitus. *Curr. Opin. Immunol.* 3:902–905.

Buyon J. P.1998. The effects of pregnancy on auto-immune diseases. *J. Leukoc. Biol.* 63:281–287.

Elias D. 1994. The NOD mouse: a model for auto-immune insulin-dependent diabetes. (book) Auto-immune Models: A guidebook. 147–161.

Gill, P. S., Lunardi-Iskandar, Y. Gallo R. C. 1996. The effects of preparations of human chorionic gonadotropin on AIDS-related kaosi's Sarcoma. *New Eng. J. Med.* 335:1261–1269.

Grossman J. M., Brahn E. 1997. Rheumatoid arthritis: current clinical and research directions. *J. Womens Health.* 6:627–638.

Harada, M., and S. Makino. 1986. Suppression of overt diabetes in NOD mice by anti-thromobocyte serum or anti-Thy 1, 2 antibody. Jikken. Dobutsu. 35:501–504.

Hintzen R. Q. 1997. Th-cell modulation in multiple sclerosis. *Immunology Today* 18:507–508.

Hotamisligil G. S., Spiegelman B. M. 1994. Tumor necrosis factor alpha: a key component of the obesity-diabetes link. *Diabetes* 43:1271–1278.

Katz, J. D., C. Benoist and D. Mathis. 1995. T helper cell subsets in insulin-dependent diabetes. *Science (Wash. D.C.).* 268:1185–1188.

Liblau, R. S., S. M. Singer, and H. O. McDevitt. 1995. Th1 and Th2 CD4+ T-cells in the pathogenesis of organ-specific auto-immune diseases. *Immunol. Today.* 16:34–38.

Lunardi-Iskandar, . . . Gallo R. C. 1995. Tumorigenesis and metastasis of neoplastic Kaposi's sarcoma cell line in immunodeficient mice blocked by a human pregnancy hormone. *Nature* (Lond.). 375:64–68.

Lunardi-Iskandar, Y., Bryant, J. L. Blattner W. A., Hung C. L, Flamand L., Gill P., Hermans P., Birken S., and Gallo R. C. 1998. Effects of a urinary factor from women in early pregnancy on HIV-1, SIV and mediated disease. *Nature Med.* 4:428–434.

Makino, S., M. Harada, Y. Kishimoto, and Y. Hayashi. 1986. Absence of insulitis and overt diabetes in athymic nude mice with NOD genetic background. *Jikken. Dobutsu.* 35:495–498.

Miles P. D., Romeo O. M., Higo K., Cohen A., Rafaat K., Olefsky J. M. 1997. TNF-alpha-induced insulin resistance in vivo and its prevention by troglitazone. *Diabetes.* 46:1678–1683.

Miyazaki, A., T. Hanafusa, K. Yamada, J. Miyagawa, H. Fujino-Kurihara, H. Nakajima, K. Nonaka, and S. Tarui. 1985. Predominance of T-lymphocytes in pancreatic islets and spleen of pre-diabetic non-obese diabetic (NOD) mice: a longitudinal study. *Clin. Exp. Immunol.* 60:622–630.

Ofei F., Hurel S., Newkirk J., Sopwith M., Taylor R. 1996. Effects of an engineered human anti-TNF-alpha antibody (CDP571) on insulin sensitivity and glycemic control in patients with NIDDM. *Diabetes* 45:881–885.

O'Garra, A., Steinman, L, and Gijbels, K. 1997. CD4+ T-cell subsets in auto-immunity. *Curr. Opin. Immunol.* 9(6):872–883.

O'Reilly, L. A., P. R. Hutchings, P. R. Crocker, E. Simpson, T. Lund, D. Kiossis, F. Takei, J. Baird, and A. Cooke. 1991. Characterization of pancreatic isle T-cell infiltrates in NOD mice: effect of cell transfer and transgene expression. *Eur. J. Immunol.* 21:1171–1180.

Pakala, S. V., Kurrer, M. O. and Katz, J. D. 1997. T helper 2 (Th2) T-cells induce acute pancreatitis and diabetes in immune-compromised nonobese diabetic (NOD) mice. *J. Exp. Med.* 186:299–306.

Pfeiffer A., Janott J., Mohlig M., Ristow M., Rochlitz H., Busch K., Schatz H., Schifferdecker E. 1997. Circulating tumor necrosis factor alpha is elevated in male but not in female patients with type II diabetes mellitus. *Horm. Metab Res.* 29:111–114.

Raghupathy R.1997. Th1-type immunity is incompatible with successful pregnancy. *Immunology Today* 18:478–482.

Rosenberg, Y. J., Anderson, A. O., and Pabst, R. 1998. HIV-induced decline in blood CD4/CD8 ratios: viral killing or altered lymphocyte trafficking?. *Immunology Today* 19:10–16.

Russell A. S., Johnston C., Chew C., Maksymowych W. P. 1997. Evidence for reduced Th1 function in normal pregnancy: a hypothesis for the remission of rheumatoid arthritis. *J. Rheumatol.* 24:1045–1050.

Sempe, P., P. Bedossa, M. F. Richard, M. C. Villa, J. F. Bach, and C. Boitard. 1991. Anti-alpha/beta T-cell receptor monoclonal antibody provides an efficient therapy for autoimmune diabetes in nonobese diabetic (NOD) mice. *Eur. J. Immunol.* 21:1163–1169.

Solomon S. S., Mishra S. K., Cwik C., Rajanna B., Postlethwaite A. E. 1997. Pioglitazone and metformin reverse insulin resistance induced by tumor necrosis factor-alpha in liver cells. *Horm. Metab. Res.* 29:379–382.

Zhu X. P, Satoh J., MutoG., Muto Y., Sagara M., Takahashi K., Seino H., Hirai S., Masuda T., Tanaka S., Ishida H., Seino Y., Toyota T. 1996. Improvement of glucose tolerance with immunomodulators on type 2 diabetic animals. *Biotherapy* 9:189–197.

Bennett, J C and Plum, F. Cecil textbook of medicine. 20th edition, page 496–501.

Freudenberg, MA, Keppler, D, and Galanos, C. (1986) *Infect. Immun.* 51, 891–895.

Perkins, David et al. (1994). *Cellular Immunology.* 156, 310–321.

Huber, Pamer et al. (1993). Superantigens: a pathogens view of the immune system: Current communications in cell and molecular biology, vol. 7, Coldspring Harbor Laboratory.

Miekthke, Thomas et al. (1992) *J. Exp. Med.* 175, 91–98.

Gutierrez-Ramos, J C and Bluethmann, H. (1997) *Immunology Today.* 18, 329–334.

---

What is claimed is:

1. A method of treating sepsis in a subject comprising: administering, in a pharmaceutically acceptable manner, a pharmaceutically effective amount of two or more immunoregulators, immunoregulators peptides, functional fragments or functional analogues thereof to the subject, wherein said immunoregulators comprise peptide and recombinant hCG.

2. The method of claim 1 wherein the peptide is selected from the group consisting of SEQ ID NO: 1, SEQ ID NO: 2, SEQ ID NO: 3 and a functional fragment thereof.

3. A method of treating sepsis in a subject comprising: administering, in a pharmaceutically acceptable manner, a pharmaceutically effective amount of two or more immunoregulators to said subject, wherein at least one of said immunoregulators is a peptide, wherein said tide is obtainable from a mammalian chorionic gonadotropin preparation or a synthetic peptide analogue thereof.

4. The method according to claim 3 wherein the peptide is selected from the group consisting of SEQ ID NO: 1, SEQ ID NO: 2, SEQ ID NO: 3 and a functional fragment of any thereof.

5. The method according to claim 4 wherein both immunoregulators are selected from the group of immunoregulators consisting of SEQ ID NO: 1, SEQ ID NO: 2, and SEQ ID NO: 3 and a functional fragment of any thereof.

6. The method according to claim 3 wherein one of said immunoregulators is human chorionic gonadotropin.

7. The method according to claim 4 wherein the peptide is that of SEQ ID NO: 1.

8. The method according to claim 4 wherein the peptide is that of SEQ ID NO: 2.

9. The method according to claim 4 wherein the peptide is that of SEQ ID NO: 3.

* * * * *

UNITED STATES PATENT AND TRADEMARK OFFICE
CERTIFICATE OF CORRECTION

PATENT NO. : 6,844,315 B2
APPLICATION NO. : 09/821380
DATED : January 18, 2005
INVENTOR(S) : Nisar Ahmed Khan and Robbert Benner It is certified that error appears in the above-identified patent and that said Letters Patent is hereby corrected as shown below:

On the title page:
In ITEM (56) References Cited below "U.S. PATENT DOCUMENTS" add
--4,977,244  12/1990  Muchmore et al.--
--5,361,992  B1  3/2002  Szkudlinski et al.--
--5,677,275  10/1997  Lunardi-Iskandar et al.--
--5,851,997  12/1998  Harris--
--5,854,004  12/1998  Czernilofsky et al.--
--5,877,148  3/1999  Lunardi-Iskandar et al.--
--5,968,513  10/1999  Gallo et al.--
--5,997,871  12/1999  Gallo et al.--
--6,489,296  12/2002  Grinnell et al.--
--6,583,109  B1  6/2003  Gallo et al.--
--6,596,688  B1  7/2003  Gallo et al.--
--6,620,416  B1  9/2003  Gallo et al.--
--2002/0041871  4/2002  Brudnak--
--2002/0064501  A1  5/2002  Khan et al.--
--2003/0049273  A1  3/2003  Gallo et al.-- below "FOREIGN PATENT DOCUMENTS" add
--DE  3715662  11/1987--
--WO  96/04008  2/1996--
--WO  97/49373  12/1997--
--WO  97/49418  12/1997--
--WO  97/49432  12/1997--
--WO  98/35691  8/1998--

UNITED STATES PATENT AND TRADEMARK OFFICE
CERTIFICATE OF CORRECTION

| | |
|---|---|
| PATENT NO. | : 6,844,315 B2 |
| APPLICATION NO. | : 09/821380 |
| DATED | : January 18, 2005 |
| INVENTOR(S) | : Nisar Ahmed Khan and Robbert Benner |

It is certified that error appears in the above-identified patent and that said Letters Patent is hereby corrected as shown below:

On the title page (continued):
In ITEM (56) References Cited below "FOREIGN PATENT DOCUMENTS" add
--DE    19953339    5/2001--
--EP    1 138 692 A1    10/2001--
--WO    02/085117    0/2002--
--EP    1 300 418    4/2003-- below "OTHER PUBLICATIONS" add
--International Search Report, International Application No. PCT/NL02/00639, mailed August 4, 2003 (8 pages).--
--Christman et al., Nuclear factor kappaB: a pivotal role in the systemic inflammatory response syndrome and new target for therapy, Intens Care Med, 1998, pp. 1131-38, Vol. 24.--
--Jyonouchi et al., Proinflammatory and regulatory cytokine production associated with innate and adaptive immune responses in children with autism spectrum disorders and developmental regression, J Neuroim., 2001 pp. 170-79, Vol. 120.--
--Kanungo et al., Advanced Maturation of Heteropneustes Fossilis (Bloch) by Oral Administration of Human Chorionic Gonadotropin, J. Adv. Zool., 1999, pp. 1-5, Vol. 20.--

UNITED STATES PATENT AND TRADEMARK OFFICE
CERTIFICATE OF CORRECTION

| | |
|---|---|
| PATENT NO. | : 6,844,315 B2 |
| APPLICATION NO. | : 09/821380 |
| DATED | : January 18, 2005 |
| INVENTOR(S) | : Nisar Ahmed Khan and Robbert Benner |

It is certified that error appears in the above-identified patent and that said Letters Patent is hereby corrected as shown below:

On the title page (continued):

In ITEM (56) References Cited below "OTHER PUBLICATIONS" add
--Patil, A., et al., "The Study of the Effect of Human Chorionic Gonadotrophic (HCG) Hormone on the Survival of Adrenal Medulla Transplant in Brain. Preliminary Study," 87 ACTA NEUROCHIR (WIEN) 76-78 (1987).--
--Rohrig et al., Growth-stimulating Influence of Human Chorionic Gonadotropin (hCG) on Plasmodium falciparum in vitro, Zentralblatt Bakt, 1999, pp. 88-89, Vol. 289.--
--Slater, Lewis M., et al. "Decreased Mortality of Murine Graft-Versus-Host Disease by Human Chorionic Gonadatropin," 23(1) TRANSPLANTATION 103-104 (January 1997).--
--Tak et al., NF-kappaB: a key role in inflammatory diseases, J Clin Invest., 2001, pp. 7-11, Vol. 107.--
--Tan et al., The role of activation of nuclear factor-kappaB of rat brain in the pathogenesis of experimental allergic encephalomyelitis, Acta Physiol Sinica, 2003, pp. 58-64, Vol. 55.--
--Tovey et al., Mucosal Cytokine Therapy: Marked Antiviral and Antitumor Activity, J. Interferon Cytokine Res. 1999, pp. 911-21, Vol. 19.--

UNITED STATES PATENT AND TRADEMARK OFFICE
CERTIFICATE OF CORRECTION

| | |
|---|---|
| PATENT NO. | : 6,844,315 B2 |
| APPLICATION NO. | : 09/821380 |
| DATED | : January 18, 2005 |
| INVENTOR(S) | : Nisar Ahmed Khan and Robbert Benner |

It is certified that error appears in the above-identified patent and that said Letters Patent is hereby corrected as shown below:

On the title page (continued):

In ITEM (56) References Cited below "OTHER PUBLICATIONS" add
--Albini A., et al., "Old drugs as novel angiogenesis inhibitors: Preclinical studies with NAC, hCG, EGCG, and somatostatin," 17 CLINICAL & EXPERIMENTAL METASTASIS 739 (1999).--
--Blackwell, Timothy S., et al., The Role of Nuclear factor-kB in Cytokine Gene Regulation," 17 AM. J. RESPIR. Cell MOL. BIOL. 3-9 (1997).--
--Keller, S., et al., Human Chorionic Gonadotropin (hCG) Is a Potent Angiogenic Factor for Uterine Endothelial cells *in Vitro*," 20(5-6) PLACENTA, page A37 (July 1999).--
--Khan, Nisar A., et al., "Inhibition of Diabetes in NOD Mice by Human Pregnancy Factor," 62(12) HUMAN IMMUNOLOGY 1315-1323 (December 2001).--
--Khan, Nisar A., et al., "Inhibition of Septic Shock in Mice by an Oligopeptide From the β-chain of Human Chorionic Gonadotropin Hormone," 63(1) HUMAN IMMUNOLOGY 1-7 (January 2002).--

UNITED STATES PATENT AND TRADEMARK OFFICE
CERTIFICATE OF CORRECTION

| | | |
|---|---|---|
| PATENT NO. | : 6,844,315 B2 | |
| APPLICATION NO. | : 09/821380 | |
| DATED | : January 18, 2005 | |
| INVENTOR(S) | : Nisar Ahmed Khan and Robbert Benner | |

It is certified that error appears in the above-identified patent and that said Letters Patent is hereby corrected as shown below:

On the title page (continued):

In ITEM (56) References Cited below "OTHER PUBLICATIONS" add
--Muchmore et al., Immunoregulatory Properties of Fractions From Human Pregnancy Urine: Evidence that Human Chorionic Gonadotropin is not Responsible, The Journal of Immunology, March 1997, pp. 881-86, Vol. 118, No. 3.--
--Muchmore et al., Purification and Characterization of a Mannose-Containing Disaccharide Obtained From Human Pregnancy Urine, Journal of Experimental Medicine, December 1984, pp. 1672-85, Volume 160.--
--Wulczyn, F. Gregory, et al. "The NF-kB/Rel and IkB gene families: mediators of immune responses and inflammation," 74(12) J. MOL. MED. 749-769 (1996).--
--Yamamoto, Y., et al., "Role of the NF-kB Pathway in the Pathogenesis of Human Disease States," 1(3) CURRENT MOLECULAR MEDICINE 287-296 (July 2001).--

UNITED STATES PATENT AND TRADEMARK OFFICE
CERTIFICATE OF CORRECTION

| | |
|---|---|
| PATENT NO. | : 6,844,315 B2 |
| APPLICATION NO. | : 09/821380 |
| DATED | : January 18, 2005 |
| INVENTOR(S) | : Nisar Ahmed Khan and Robbert Benner |

It is certified that error appears in the above-identified patent and that said Letters Patent is hereby corrected as shown below:

In the specification:

| | | |
|---|---|---|
| COLUMN 2, | LINES 36,37, | change "Sj ögrens syndrome" to --Sjögrens syndrome-- |
| COLUMN 13, | LINES 12,13, | change "Sj ögrens syndrome" to --Sjögrens syndrome-- |
| COLUMN 29, | LINE 67, | change "(in vivolin vitro)" to --(in vivo/in vitro)-- |
| COLUMN 55, | LINES 48,49, | change "PCT/NL99/003131" to --PCT/NL99/00313-- |
| COLUMN 60, | LINE 37, | change "PCT/NL99/003131" to --PCT/NL99/00313-- |
| COLUMN 62, | LINE 26, | change "PCT/NL99/003131" to --PCT/NL99/00313-- |
| COLUMN 62, | LINE 36, | change "PCT/NL99/003131" to --PCT/NL99/00313-- |

In the claims:
CLAIM 3, COLUMN 71, LINE 65, change "tide" to --peptide--

Signed and Sealed this

Thirtieth Day of December, 2008

JON W. DUDAS
*Director of the United States Patent and Trademark Office*